(12) United States Patent
Vanotti et al.

(10) Patent No.: US 8,263,604 B2
(45) Date of Patent: Sep. 11, 2012

(54) PYRIDYL- AND PYRIMIDINYL-SUBSTITUTED PYRROLE-, THIOPHENE- AND FURANE-DERIVATIVES AS KINASE INHIBITORS

(75) Inventors: Ermes Vanotti, Milan (IT); Marina Caldarelli, Milan (IT); Alessandra Cirla, Varese (IT); Barbara Forte, Milan (IT); Antonella Ermoli, Buccinasco (IT); Maria Menichincheri, Milan (IT); Antonio Pillan, Milan (IT); Alessandra Scolaro, Bresso (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 989 days.

(21) Appl. No.: 12/293,951

(22) PCT Filed: Mar. 19, 2007

(86) PCT No.: PCT/EP2007/052587
§ 371 (c)(1),
(2), (4) Date: Sep. 22, 2008

(87) PCT Pub. No.: WO2007/110344
PCT Pub. Date: Oct. 4, 2007

(65) Prior Publication Data
US 2009/0099221 A1  Apr. 16, 2009

(30) Foreign Application Priority Data
Mar. 27, 2006  (EP) .................. 06111766

(51) Int. Cl.
A61K 31/505 (2006.01)
A61K 31/47 (2006.01)
A61K 31/44 (2006.01)
C07D 239/42 (2006.01)
C07D 401/04 (2006.01)
C07D 217/06 (2006.01)
C07D 211/68 (2006.01)
C07D 213/69 (2006.01)

(52) U.S. Cl. ........ 514/275; 514/256; 514/307; 514/343; 544/331; 544/333; 546/146; 546/193; 546/296; 546/276.4

(58) Field of Classification Search .................. 514/275, 514/256, 307, 343; 544/331, 333; 546/146, 546/193, 276
See application file for complete search history.

(56) References Cited

FOREIGN PATENT DOCUMENTS
EP  0 853 083 A1  7/1998
WO  WO 98/02430  1/1998
WO  WO 2005/095386 A1  10/2005

*Primary Examiner* — James O Wilson
*Assistant Examiner* — Ebenezer O Sackey
(74) *Attorney, Agent, or Firm* — Scully, Scott, Murphy & Presser, P.C.

(57) ABSTRACT

The present invention provides compounds of the formula (I), or the pharmaceutically acceptable salts thereof, wherein G, W, $R_2$, $R_3$, $R_4$, $R_5$ and $R_6$ are as defined in the specification. Further objects of the invention are processes and intermediates for the preparation of the compounds of the formula (I), pharmaceutical compositions comprising them and methods for treating cell proliferative disorders. As a matter of fact, the compounds of the formula (I) are useful, in therapy, in the treatment of diseases associated with a disregulated protein kinase activity, like cancer.

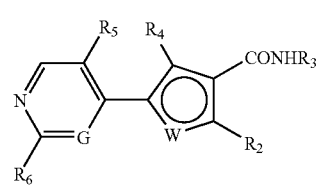

(I)

16 Claims, No Drawings

PYRIDYL- AND PYRIMIDINYL-SUBSTITUTED PYRROLE-, THIOPHENE- AND FURANE-DERIVATIVES AS KINASE INHIBITORS

The present invention relates to heteropentacycles, a process for their preparation, pharmaceutical compositions comprising them and their use as therapeutic agents, particularly in the treatment of cancer and cell proliferation disorders.

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases. For a general reference to PKs malfunctioning or disregulation see, for instance, Current Opinion in Chemical Biology 1999, 3, 459-465.

Among the several protein kinases known in the art as being implicated in the growth of cancer cells is Cdc7, an evolutionary conserved serine-threonine kinase which plays a pivotal role in linking cell cycle regulation to genome duplication, being essential for the firing of DNA replication origins (see Montagnoli A. et al., EMBO Journal, 2002, Vol. 21, No. 12, 3171; Montagnoli A. et al., Cancer Research 2004, Vol. 64, October 1, 7110).

Several heterocyclic compounds are known in the art as protein kinase inhibitors.

Among them are, for instance, pyrrolo-pyrazoles disclosed in WO2002/12242; tetrahydroindazoles disclosed in WO2000/69846; pyrrolo-pyridines disclosed in WO2001/98299; aminophthalazinones disclosed in WO2003/014090 and aminoindazoles disclosed in WO2003/028720. Pyrrole derivatives are disclosed in WO2001/001986, WO98/35944, thiazole derivatives are reported in WO2002/030358 and thiophenes are claimed to be kinase inhibitors in WO2005/095386. WO2006/012642 discloses pyrrole derivatives modulating the activity of one or more steroid nuclear receptors, and WO2003/068749 discloses furan derivatives modulating vanilloid receptors.

Pyridylfurans and pyridylthiophenes are described in EP853083 as inhibitors of TNFα biosynthesis and CAMs expression; pyridylpyrroles are disclosed in WO98/02430 as interleukin and tumor necrosis factor antagonists; pyrrole acids and esters are also therein disclosed. Piperazinylphenylcarboxamide derivatives containing a furane ring are disclosed in WO95/04729 as 5-HT1D receptor antagonists. In WO2005/100342 there are disclosed and claimed pyrimidine/pyridine substituted pyrroles having antiproliferative and Erk2 kinase inhibition activities. In WO2000/006085 there are disclosed and claimed heterocyclecarboxamides as CCR5 receptor modulators.

The present inventors have now discovered some compounds useful, in therapy, as agents against a host of diseases caused by and/or associated to a disregulated protein kinase activity and, more particularly, Cdc7 or Cdc7/Cdks activity.

It is another object of the present invention to provide compounds endowed with protein kinase inhibiting activity and, more particularly, Cdc7 or Cdc7/Cdks inhibiting activity.

In particular, the present invention provides heteropentacycles that are endowed with protein kinase inhibiting activity, especially Cdc7 or Cdc7/Cdks inhibiting activity.

More specifically, the compounds of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Due to the key role of PKs, and, in particular, of Cdc7 and Cdks like Cdk2 in the regulation of cellular proliferation, these heteropentacycles are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

The compounds of the invention can be also active as inhibitors of other protein kinases such as, for instance, protein kinase C in different isoforms, Met, PAK-4, PAK-5, ZC-1, STLK-2, DDR-2, Aurora 1, Aurora 2, Bub-1, PLK, Chk1, Chk2, HER2, raf1, MEK1, MAPK, EGF-R, PDGF-R, FGF-R, IGF-R, VEGF-R, PI3K, weel kinase, Src, Abl, Akt, ILK, MK-2, IKK-2, Nek, CK2, GSK3, SULU, PKA, PKC, PDK, RET, KIT, LCK, TRKA and thus be effective in the treatment of diseases associated with other protein kinases.

Accordingly, in a first embodiment, the present invention provides a compound of the formula (I):

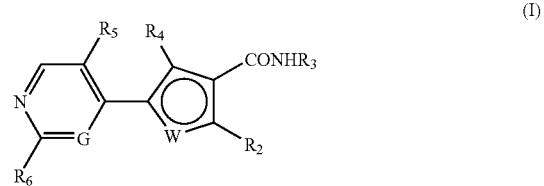

(I)

wherein
G is CH or nitrogen atom;
W is an oxygen atom, $NR_1$ or $S(O)_n$; n is 0, 1 or 2;
$R_1$ and $R_3$ independently represent hydrogen atom or an optionally substituted group selected from alkyl, cycloalkyl, alkenyl, alkynyl, heterocyclyl, heterocyclylalkyl, aryl, arylalkyl, heterocyclyloxy-alkyl and alkoxycarbonyl group;
$R_2$ is hydrogen or halogen atom, or an optionally substituted group selected from aryl, cycloalkyl and heterocyclyl group;
$R_4$ is hydrogen or halogen atom, or an optionally substituted alkyl or alkenyl group;
$R_5$ is hydrogen or halogen atom;
$R_6$ is hydrogen atom or $NHR_7$;
$R_7$ is hydrogen atom, an optionally substituted group selected from alkyl, aryl, cycloalkyl and heterocyclyl group or —CO—$R_1$ wherein $R_1$ is as defined above;
or a pharmaceutically acceptable salt thereof, with the proviso that the following compounds are excluded:
2,5-di(pyridin-4-yl)-thiophene-3-carboxylic acid amide,
2,5-di(pyridin-4-yl)-thiophene-3-carboxylic acid methylamide, 2,5-di(pyridin-4-yl)-4-methyl-pyrrole-3-carboxylic acid amide,
5-pyridin-4-yl-furan-3-carboxylic acid [4-methoxy-3-(4-methyl-piperazin-1-yl)-phenyl]-amide,
5-pyridin-4-yl-furan-3-carboxylic acid (1-methyl-1,2,3,4-tetrahydro-quinolin-7-yl)-amide and
N-[2-amino-1-(2,4-dichlorobenzyl)ethyl]-5-[2-(methylamino)pyrimidin-4-yl]thiophene-3-carboxamide.

The compounds of formula (I), object of the invention, are obtainable through a synthetic process comprising well known reactions carried out according to conventional techniques, as well as through an extremely versatile solid-phase and/or combinatorial process, being all comprised within the scope of the invention.

The present invention also provides a pharmaceutical composition comprising a compound of formula (I) as defined above and at least one pharmaceutically acceptable excipient, carrier or diluent.

Preferably, a compound of the formula (I) is characterized in that W is $NR_1$, $R_1$ and $R_3$ independently represent hydrogen atom or an optionally substituted alkyl group, and $R_6$ is $NHR_7$ wherein $R_7$ is hydrogen atom or an optionally substituted aryl group.

More preferably, a compound of the formula (I) is characterized in that W is $NR_1$; $R_1$ represent hydrogen atom or an optionally substituted alkyl group; $R_3$ and $R_4$ represent hydrogen atoms, $R_2$ is an optionally substituted aryl or heterocyclyl group; and $R_6$ is $NH_2$.

Even more preferred are the compounds of the formula (I) wherein W is NH or $R_3$ represents hydrogen atom. Specific, not limiting, preferred compounds of formula (I) of the invention, whenever appropriate in the form of pharmaceutically acceptable salts, are the following:

2-phenyl-5-pyridin-4-yl-1H-pyrrole-3-carboxylic acid amide (A1),
2-(2-fluoro-phenyl)-5-pyridin-4-yl-1H-pyrrole-3-carboxylic acid amide (A2),
2-(3-fluoro-phenyl)-5-pyridin-4-yl-1H-pyrrole-3-carboxylic acid amide (A3),
2-(4-fluoro-phenyl)-5-pyridin-4-yl-1H-pyrrole-3-carboxylic acid amide (A4),
5-pyridin-4-yl-2-o-tolyl-1H-pyrrole-3-carboxylic acid amide (A7),
5-pyridin-4-yl-2-m-tolyl-1H-pyrrole-3-carboxylic acid amide (A8),
5-pyridin-4-yl-2-p-tolyl-1H-pyrrole-3-carboxylic acid amide (A9),
2-(3-methoxy-phenyl)-5-pyridin-4-yl-1H-pyrrole-3-carboxylic acid amide (A11),
2-(4-methoxy-phenyl)-5-pyridin-4-yl-1H-pyrrole-3-carboxylic acid amide (A12),
2-(2-nitro-phenyl)-5-pyridin-4-yl-1H-pyrrole-3-carboxylic acid amide (A13),
2-(3-nitro-phenyl)-5-pyridin-4-yl-1H-pyrrole-3-carboxylic acid amide (A14),
2-(2,3-dimethyl-phenyl)-5-pyridin-4-yl-1H-pyrrole-3-carboxylic acid amide (A20),
5-pyridin-4-yl-2-thiophen-3-yl-1H-pyrrole-3-carboxylic acid amide (C1),
2-furan-3-yl-5-pyridin-4-yl-1H-pyrrole-3-carboxylic acid amide (C2),
5-(3-fluoro-pyridin-4-yl)-2-phenyl-1H-pyrrole-3-carboxylic acid amide (E1),
5-(3-fluoro-pyridin-4-yl)-2-o-tolyl-1H-pyrrole-3-carboxylic acid amide (E2),
5-(2-amino-pyrimidin-4-yl)-2-phenyl-1H-pyrrole-3-carboxylic acid amide (F1),
5-(2-amino-pyrimidin-4-yl)-2-o-tolyl-1H-pyrrole-3-carboxylic acid amide (F2),
5-(2-amino-pyrimidin-4-yl)-2-(2-fluoro-phenyl)-1H-pyrrole-3-carboxylic acid amide (F4),
5-(2-amino-pyrimidin-4-yl)-2-(4-fluoro-2-methyl-phenyl)-1H-pyrrole-3-carboxylic acid amide (F13),
5-(2-amino-pyrimidin-4-yl)-2-(5-fluoro-2-methyl-phenyl)-1H-pyrrole-3-carboxylic acid amide (F14),
5-(2-amino-pyrimidin-4-yl)-2-(2,3-dimethyl-phenyl)-1H-pyrrole-3-carboxylic acid amide (F15),
5-(2-amino-pyrimidin-4-yl)-2-(2,3-difluoro-phenyl)-1H-pyrrole-3-carboxylic acid amide (F16),
5-(2-amino-pyrimidin-4-yl)-2-(2,4-difluoro-phenyl)-1H-pyrrole-3-carboxylic acid amide (F17),
5-(2-amino-pyrimidin-4-yl)-2-(2,5-difluoro-phenyl)-1H-pyrrole-3-carboxylic acid amide (F18),
5-(2-amino-pyrimidin-4-yl)-2-(2-chloro-phenyl)-1H-pyrrole-3-carboxylic acid amide (F19),
5-(2-amino-pyrimidin-4-yl)-2-(2-chloro-4-fluoro-phenyl)-1H-pyrrole-3-carboxylic acid amide (F23),
5-(2-amino-pyrimidin-4-yl)-2-(2,4-dichloro-phenyl)-1H-pyrrole-3-carboxylic acid amide (F26),
5-(2-amino-pyrimidin-4-yl)-2-(2-fluoro-4-methyl-phenyl)-1H-pyrrole-3-carboxylic acid amide (F28),
5-(2-amino-pyrimidin-4-yl)-2-(2-fluoro-3-methyl-phenyl)-1H-pyrrole-3-carboxylic acid amide (F30),
5-(2-amino-pyrimidin-4-yl)-2-(2-chloro-5-fluoro-phenyl)-1H-pyrrole-3-carboxylic acid amide (F31),
5-(2-amino-pyrimidin-4-yl)-2-(3-chloro-2-fluoro-phenyl)-1H-pyrrole-3-carboxylic acid amide (F33),
5-(2-amino-pyrimidin-4-yl)-2-(2,3-dichloro-phenyl)-1H-pyrrole-3-carboxylic acid amide (F34),
5-(2-amino-pyrimidin-4-yl)-2-(2-fluoro-3-methoxy-phenyl)-1H-pyrrole-3-carboxylic acid amide (F35),
5-(2-amino-pyrimidin-4-yl)-2-(4-chloro-2-fluoro-phenyl)-1H-pyrrole-3-carboxylic acid amide (F36),
5-(2-amino-pyrimidin-4-yl)-2-(2-bromo-phenyl)-1H-pyrrole-3-carboxylic acid amide (F38),
5-(2-amino-pyrimidin-4-yl)-2-(2-chloro-3-methoxy-phenyl)-1H-pyrrole-3-carboxylic acid amide (F39),
5-(2-amino-pyrimidin-4-yl)-2-(3-methoxy-2-methyl-phenyl)-1H-pyrrole-3-carboxylic acid amide (F40),
5-(2-amino-pyrimidin-4-yl)-2-(2-chloro-3-fluoro-phenyl)-1H-pyrrole-3-carboxylic acid amide (F41),
5-(2-amino-pyrimidin-4-yl)-2-(3-bromo-2-chloro-phenyl)-1H-pyrrole-3-carboxylic acid amide (F42),
5-(2-amino-pyrimidin-4-yl)-2-(2-bromo-3-chloro-phenyl)-1H-pyrrole-3-carboxylic acid amide (F43),
5-(2-amino-pyrimidin-4-yl)-2-(2,3-dibromo-phenyl)-1H-pyrrole-3-carboxylic acid amide (F44),
5-(2-amino-pyrimidin-4-yl)-2-(3-bromo-2-fluoro-phenyl)-1H-pyrrole-3-carboxylic acid amide (F45),
5-(2-amino-pyrimidin-4-yl)-2-(3-bromo-2-methyl-phenyl)-1H-pyrrole-3-carboxylic acid amide (F46),
5-(2-amino-pyrimidin-4-yl)-2-(2-bromo-3-methyl-phenyl)-1H-pyrrole-3-carboxylic acid amide (F47),
5-(2-amino-pyrimidin-4-yl)-2-(4-methoxy-3-methyl-phenyl)-1H-pyrrole-3-carboxylic acid amide (F48),
5-(2-amino-pyrimidin-4-yl)-2-(3,4-dimethoxy-phenyl)-1H-pyrrole-3-carboxylic acid amide (F49),
5-(2-amino-pyrimidin-4-yl)-2-(2-fluoro-4-methoxy-phenyl)-1H-pyrrole-3-carboxylic acid amide (F50),
5-(2-amino-pyrimidin-4-yl)-2-(2-chloro-4-methoxy-phenyl)-1H-pyrrole-3-carboxylic acid amide (F51),
5-(2-amino-pyrimidin-4-yl)-2-(2-bromo-4-fluoro-phenyl)-1H-pyrrole-3-carboxylic acid amide (F52), 5-(2-amino-pyrimidin-4-yl)-2-(4-methoxy-2-methyl-phenyl)-1H-pyrrole-3-carboxylic acid amide (F53),
5-(2-amino-pyrimidin-4-yl)-2-thiophen-3-yl-1H-pyrrole-3-carboxylic acid amide (G1),
5-(2-amino-pyrimidin-4-yl)-2-thiophen-2-yl-1H-pyrrole-3-carboxylic acid amide (G2),
5-(2-amino-pyrimidin-4-yl)-2-(5-methyl-thiophen-2-yl)-1H-pyrrole-3-carboxylic acid amide (G3),
5-(2-amino-pyrimidin-4-yl)-2-(5-chloro-thiophen-2-yl)-1H-pyrrole-3-carboxylic acid amide (G4),
5-(2-amino-5-chloro-pyrimidin-4-yl)-2-phenyl-1H-pyrrole-3-carboxylic acid amide (N1),
5-(2-amino-5-bromo-pyrimidin-4-yl)-2-phenyl-1H-pyrrole-3-carboxylic acid amide (N2),
5-(2-amino-pyrimidin-4-yl)-4-iodo-2-phenyl-1H-pyrrole-3-carboxylic acid amide (N3),
5-(2-amino-5-chloro-pyrimidin-4-yl)-2-(2-fluoro-phenyl)-1H-pyrrole-3-carboxylic acid amide (N7),
5-(2-amino-5-bromo-pyrimidin-4-yl)-2-(2-fluoro-phenyl)-1H-pyrrole-3-carboxylic acid amide (N8),
5-(2-amino-pyrimidin-4-yl)-2-phenyl-thiophene-3-carboxylic acid amide (S1),
5-(2-amino-5-fluoro-pyrimidin-4-yl)-2-phenyl-1H-pyrrole-3-carboxylic acid amide (V1) and
5-(2-amino-pyrimidin-4-yl)-4-chloro-2-phenyl-1H-pyrrole-3-carboxylic acid amide (Z1).

More preferred compounds according to the present inventions are:
5-(2-amino-pyrimidin-4-yl)-2-(2,3-dimethyl-phenyl)-1H-pyrrole-3-carboxylic acid amide (F15),
5-(2-amino-pyrimidin-4-yl)-2-(2,4-dichloro-phenyl)-1H-pyrrole-3-carboxylic acid amide (F26) and
5-(2-amino-pyrimidin-4-yl)-2-(4-chloro-2-fluoro-phenyl)-1H-pyrrole-3-carboxylic acid amide (F36), or their pharmaceutically acceptable salt thereof.

A method of treating cell proliferative disorders caused by and/or associated with an altered Cdc7 kinase activity by administering to a mammal in need thereof an effective amount of a compound of formula I as defined above is also provided.

In a preferred embodiment of the method described above, the cell proliferative disorder is cancer.

Specific types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratoxanthoma, thyroid follicular cancer, and Kaposi's sarcoma.

The bonds of the heteropentacycle are aromatic; the numbering of said heteropentacycle is as shown hereinbelow:

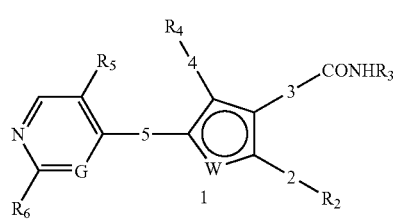

(I)

In the present description, unless otherwise specified, the following terms have the following meanings.

Aryl, cycloalkyl and heterocyclyl groups sometimes will be collectively defined as "cyclyl" for convenience.

The term "alkyl" or "Alk" refers to straight or branched monovalent saturated aliphatic hydrocarbyl groups having from 1 to 6 carbon atoms. This term is exemplified by groups such as methyl, ethyl, n-propyl, iso-propyl, n-butyl, isobutyl, sec-butyl, t-butyl, n-pentyl, n-hexyl, and the like. "Substituted alkyl" refers to an alkyl group having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogens, hydroxyl, nitro, carboxyl, carboxyl esters, cycloalkyl, substituted cycloalkyl, heterocyclyl, and substituted heterocyclyl.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclohexyl, cyclooctyl and the like.

"Substituted cycloalkyl" refers to a cycloalkyl, having from 1 to 5 substituents selected from the group consisting of oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heterocyclyl, and substituted heterocyclyl.

"Alkenyl" refers to alkenyl groups having from 2 to 6 carbon atoms. Such groups are exemplified by vinyl, allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heterocyclyl, and substituted heterocyclyl with the proviso that any hydroxyl substitution is not attached to a vinyl (unsaturated) carbon atom.

"Alkynyl" refers to alkynyl groups having from 2 to 6 carbon atoms. "Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heterocyclyl, and substituted heterocyclyl with the proviso that any hydroxyl substitution is not attached to an acetylene (unsaturated) carbon atom.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like. "Substituted alkoxy" refers to the group "substituted alkyl-O—".

"Acyl" refers to the groups H—C(O)—, alkyl-C(O)—, substituted alkyl-C(O)—, cycloalkyl-C(O)—, substituted cycloalkyl-C(O)—, aryl-C(O)—, substituted aryl-C(O)—, heterocyclyl-C(O)— and substituted heterocyclyl-C(O)—, wherein alkyl, substituted alkyl, cycloalkyl, substituted cycloalkyl, aryl, substituted aryl, heterocyclyl and substituted heterocyclyl are as defined herein.

"Acylamino" refers to the group —C(O)NR'R' where each R' is independently selected from the group consisting of hydrogen, alkyl, substituted alkyl, substituted aryl, cycloalkyl, substituted cycloalkyl, heteroaryl, substituted heteroaryl, heterocyclyl, substituted heterocyclyl and where each R' can be joined to form together with the nitrogen atom a heterocyclyl or substituted heterocyclyl ring and wherein alkyl, substituted alkyl, cycloalkyl, substituted cycloalkyl, aryl, substituted aryl, heterocyclyl and substituted heterocyclyl are as defined herein;

"Acyloxy" refers to the groups alkyl-C(O)O—, substituted alkyl-C(O)O—, aryl-C(O)O—, substituted aryl-C(O)O—, cycloalkyl-C(O)O—, substituted cycloalkyl-C(O)O—, heterocyclyl-C(O)O—, and substituted heterocyclyl-C(O)O— wherein alkyl, substituted alkyl, cycloalkyl, substituted cycloalkyl, aryl, substituted aryl, heterocyclyl and substituted heterocyclyl are as defined herein.

"Substituted amino" refers to the group —NR'R' wherein R' are as defined above provided that both R' are not hydrogen. When R' is hydrogen and the other R' is alkyl, the substituted amino group is sometimes referred to herein as alkylamino. When both of R' are alkyl, the substituted amino group is sometimes referred to herein as dialkylamino. When referring to a monosubstituted amino, it is meant that either R' is hydrogen but not both. When referring to a disubstituted amino, it is meant that neither R' is hydrogen.

"Aminoacyl" refers to the groups-NR'C(O)alkyl, —NR'C(O) substituted alkyl, —NR' C(O)cycloalkyl, —NR'C(O) substituted cycloalkyl, —NR'C(O)aryl, —NR'C(O) substituted aryl, —NR'C(O)heterocyclyl, and —NR'C(O) substituted heterocyclyl where R' is as defined above.

"Carboxyl" refers to —COOH or salts thereof.

"Carboxyl ester" refers to the groups —C(O)O-alkyl, —C(O)O— substituted alkyl, —C(O)O-aryl, and —C(O)O— substituted aryl wherein alkyl, substituted alkyl, aryl and substituted aryl are as deemed herein.

"Halo" or "halogen" or "X" refer to fluoro, chloro, bromo and iodo and preferably is fluoro, chloro or bromo.

"Aryl" or "Ar" refer to a monovalent aromatic carbocyclic group of from 6 to 14 carbon atoms having a single ring (e.g. phenyl) or multiple condensed rings (e.g. naphthyl or anthryl) which condensed rings may or may not be aromatic (e.g. 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl" refers to aryl groups which are substituted with from 1 to 3 substituents, selected from the group consisting of hydroxy, acyl, acylamino, acyloxy, alkyl, substituted alkyl, alkoxy, substituted alkoxy, amino, substituted amino, aminoacyl, aryl, substituted aryl, aryloxy, substituted aryloxy, carboxyl, carboxyl esters, cyano, cycloalkyl, substituted cycloalkyl, halo, nitro, heterocyclyl, substituted heterocyclyl, heterocyclyloxy, substituted heterocyclyloxy, amino sulfonyl ($NH_2$—$SO_2$—), and substituted aminosulfonyl.

"Aryloxy" refers to the group aryl-O— that includes, by way of example, phenoxy, naphthoxy, and the like.

"Substituted aryloxy" refers to substituted aryl-O— groups.

"Heterocyclyl" or "heterocyclic" refer to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the heterocyclic ring.

"Substituted heterocyclyl" refers to heterocyclyl groups that are substituted with from 1 to 3 of the same substituents as defined for substituted cycloalkyl.

Examples of heterocyclyls include, but are not limited to, pyridinyl, pyrrolyl, indolyl, thienyl, furyl, benzothienyl, benzofuranyl, imidazolyl, benzoimidazolyl, pyrazolyl, thiazolyl, benzothiazolyl, isothiazolyl, oxazolyl, isoxazolyl, pyrazinyl, pyrimidinyl, pyridazinyl, isoindolyl, purinyl, quinolyl, isoquinolyl, dihydroquinolinyl, 2,3-dihydro-1H-indolyl, quinoxalinyl, benzodioxolyl, indanyl, indenyl, triazolyl, azetidinyl, indolizinyl, dihydroindolyl, indazolyl, quinolizinyl, phthalazinyl, naphthylpyridinyl, quinazolinyl, cinnolinyl, pteridinyl, carbazolyl, carbolinyl, phenanthridinyl, acridinyl, phenanthrolinyl, phenazinyl, phenoxazinyl, phenothiazinyl, imidazolidinyl, imidazolinyl, piperidinyl, piperazinyl, indolinyl, phthalimidyl, 1,2,3,4-tetrahydro-isoquinolinyl, 4,5,6,7-tetrahydrobenzo[b]thiophenyl, thiazolidinyl, morpholinyl, thiomorpholinyl (also referred to as thiamorpholinyl), piperidinyl, pyrrolidinyl, pyrrolinyl, pyrazolinyl, pyrazolidinyl and tetrahydrofuranyl.

It should be noted that when referring to heterocyclyl and substituted heterocyclyl, any nitrogen or sulfur atoms that might be present may optionally be oxidized.

From all of the above, it is clear to the skilled man that any of the groups or substituents being defined, for instance, as haloalkyl, alkoxy, alkoxycarbonyl, aryloxy, heteroaryloxy, aminoalkyl, alkylamino, alkylaminoalkyl, dialkylaminoalkyl, and the like, have to be construed from the names of the groups from which they originate.

In this respect, as an example, any group which is identified as an arylalkyl or heterocycloalkyl has to be intended as an alkyl group which is further substituted by aryl or heterocycl, wherein aryl, heterocycl and alkyl are as above defined.

The compounds of formula (I) of the invention may have asymmetric carbon atoms and may therefore exist as individual optical isomers, as racemic admixtures or as any other admixture including a majority of one of the two optical isomers, which are all to be intended as comprised within the scope of the present invention.

In cases when compounds may exist in tautomeric forms, for instance keto-enol tautomers, each tautomeric form is contemplated as being included within this invention whether existing in equilibrium or predominantly in one form.

Likewise, the use as an antitumor agent of all the possible isomers and their admixtures and of both the metabolites and the pharmaceutically acceptable bio-precursors (otherwise referred to as pharmaceutically acceptable pro-drugs) of the compounds of formula (I) are also within the scope of the present invention.

As used herein, the term "pharmaceutically acceptable salts" refers to the nontoxic acid or alkaline earth metal salts of the compounds of formula I. These salts can be prepared in situ during the final isolation and purification of the compounds of formula I, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, malonate, methanesulfonate, nicotinate, 2-napthalenesulfonate, oxalate, palmoate, pectinate, persulfate, 3-phenylpropionate, picrate, pivalate, propionate, succinate, sulfate, tartrate, thiocyanate, p-toluenesulfonate and undecanoate. Also, the basic nitrogen-containing groups can be quaternized with such agents as alkyl halides, such as methyl, ethyl, propyl, and butyl chloride, bromides, and iodides, dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid, nitric acid, hydrobromic acid, perchloric acid and phosphoric acid and such organic acids as oxalic acid, maleic acid, methanesulfonic acid, succinic acid and citric acid, acetic acid, trifluoroacetic acid, propionic acid, glycolic acid, lactic acid, malonic acid, malic acid, tartaric acid, benzoic acid, cinnamic acid, mandelic acid, isethionic acid and salicylic acid.

Basic addition salts can be prepared in situ during the final isolation and purification of the compounds of formula I, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The terms "pharmaceutically acceptable prodrug" and "pharmaceutically acceptable bio-precursors" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the active parent drug, according to formula (I), in vivo, for example by hydrolysis in blood. A discussion is provided in T. Higuchi and V. Stella, Pro-drugs as Novel Delivery Systems, Vol. 14 of the A.C.S. Symposium Series, and in Edward B. Roche, ea., Bioreversible Carriers in Drug Design, American Pharmaceutical Association and Pergamon Press, 1987, both of which are incorporated herein by reference.

As formerly indicated, it is a further object of the invention a process for preparing the compounds of formula (I) as above defined and pharmaceutically acceptable salts thereof.

The compounds of this invention can be prepared from readily available starting materials using the following general methods and procedures. Unless otherwise indicated, the starting materials are known compounds or may be prepared from known compounds according to well known procedures. It will be appreciated that, where typical or preferred process conditions (i.e., reaction temperatures, times, mole ratios of reactants, solvents, pressures) are given, other process conditions can also be used unless otherwise stated. Optimum reaction conditions may vary with the particular reactants or solvent used, but such conditions can be determined by one skilled in the art by routine optimization procedures. Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Second Edition, Wiley, New York, 1991, and references cited therein.

In particular, the present invention provides a process comprising:

a) coupling a compound of formula 1E

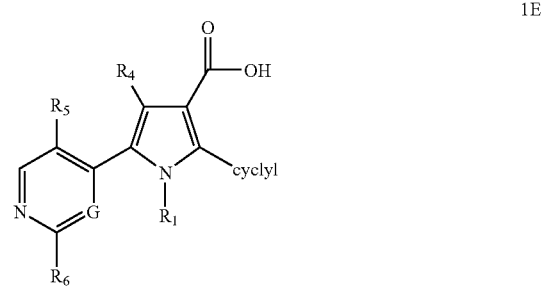

1E wherein $R_1$, $R_4$, $R_5$, $R_6$ and G are as defined above and cyclyl is an optionally substituted group selected form aryl, cycloalkyl and heterocyclyl group as defined above, either with an activated form of ammonia, optionally in the presence of a condensing agent, or with an amine of formula $R_3$—$NH_2$, wherein $R_3$ is as defined above, thus obtaining a compound of formula (I) as defined above wherein W is $NR_1$, wherein $R_1$ is as defined above, and $R_2$ is an optionally substituted group selected form aryl, cycloalkyl and heterocyclyl group;

b) optionally converting a compound of formula (I) into another different compound of formula (I), and, if desired, converting a compound of formula (I) into a pharmaceutically acceptable salt thereof or converting a salt into the free compound (I). The coupling for converting 1E into the desired compound of formula (I) may be carried out by well known primary amide-forming protocols [for example, 1-hydroxybenzotriazole ammonium salt (HOBT.$NH_3$) in the presence of either 1-(3-dimethylaminopropyl)-3-ethylcarbodiimide hydrochloride (EDCI) or O-benzotriazol-1-yl-N,N,N',N'-tetramethyluronium tetrafluoroborate (TBTU) or CDI and ammonium carbonate]; the conversion into secondary amides may be carried out by coupling with an amine of formula $R_3$—$NH_2$, wherein $R_3$ is as defined above, under a variety of well known amide-forming conditions.

Likewise, the salification of a compound of formula (I) or the conversion of its salt into the free compound (I), carried out according to well-known procedures in the art, are still within the scope of the invention.

The preparation of the compounds of formula 1E is depicted in the following Scheme 1.

Scheme 1

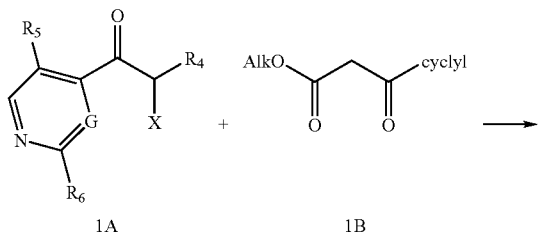

1A             1B

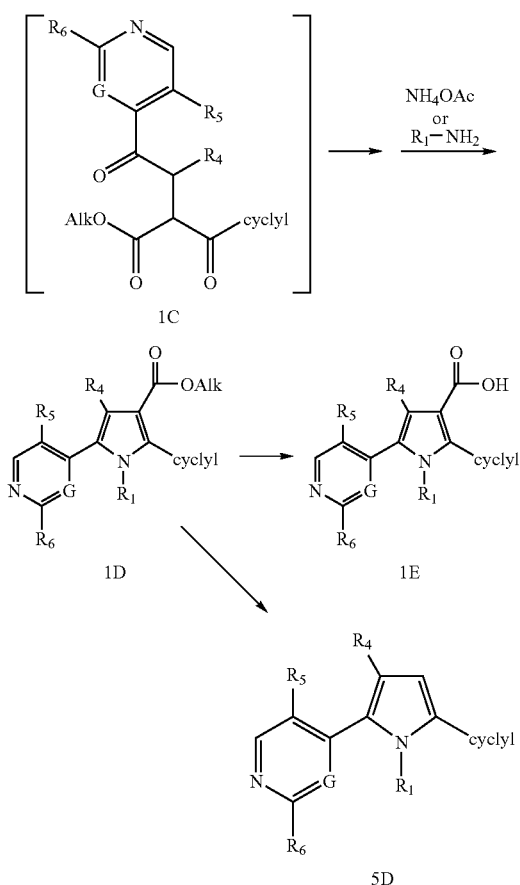

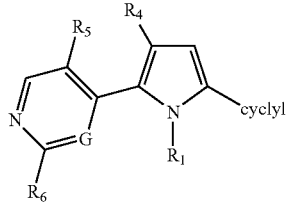

wherein $R_1$, $R_4$, $R_5$, $R_6$, G and cyclyl are as defined above, X is a halogen atom such as bromine or chlorine and Alk is a $C_1$-$C_5$ alkyl group.

Compound 1D may be formed by coupling haloketone 1A with beta-ketoester 1B in the presence of a suitable base, such as sodium hydride in a solvent like tetrahydrofuran (THF) or dimethylformamide (DMF) at temperatures ranging from −20° C. to 50° C. and then by exposing intermediate 1C to Hantzsch reaction conditions in the presence of ammonium acetate (when $R_1$=H) or of an amine of formula $R_1$—$NH_2$ in a suitable solvent such as ethanol or acetic acid or a mixture of the two, at temperatures ranging from rt to 150° C. for a period of time from about 10 min to 16 h, optionally inside a microwave cavity. Ester 1D may be then saponified in standard basic conditions to give the acid of formula 1E.

In some instances, when $R_4$ is different from hydrogen atom, ester hydrolysis of 1D may lead to the decarboxylated analog. Accordingly, another process for preparing a compound of formula I is provided which comprises the amidation of a compound formula 5D:

wherein $R_1$, $R_5$, $R_6$, G and cyclyl are as defined above and $R_4$ is not hydrogen atom, and b) optionally converting a compound of formula (I) into another different compound of formula (I), and, if desired, converting a compound of formula (I) into a pharmaceutically acceptable salt thereof or converting a salt into the free compound (I).

In this case amidation is accomplished as described, for example, in *Synthesis* 1978, 374, by exposing compound 5D to chlorosulfonylisocyanate in a suitable solvent, such as acetonitrile, dichloromethane or diethyl ether, and treating the obtained chlorosulfonylamide with alkali in order to achieve the corresponding sulfamic acid.

The sulfamic acid is then hydrolyzed to the desired compound of formula (I) in acidic medium, such as, for example, concentrated hydrochloric acid.

The compounds of formula 1A and 1B, as well as any other reactant of the process, are known and, if not commercially available per se, can be easily prepared according to known methods. The compounds of formula 1A may be prepared by halogenating, e.g. brominating or chlorinating, a suitable heteroaryl-ethanone derivative or an activated equivalent. The reaction occurs by working under conventional methods, for instance in the presence of bromine and in a suitable solvent such as aqueous hydrobromic acid or a mixture of acetic and hydrobromic acid, for a time varying between about 1 h and about 24 h. Alternatively, a suitably activated heteroaryl derivative, e.g. an alkylenolether or silylenolether, can be reacted with a halogen source, for instance N-bromo-succinimide (NBS), in a suitable solvent, such as tetrahydrofuran/water mixtures.

In particular, among the suitable haloderivatives of formula 1A, we consider 2-bromo-1-pyridin-4-yl-ethanone (commercial), 2-bromo-1-(3-fluoro-pyridin-4-yl)-ethanone (reported in WO2005013986), 2-bromo-1-pyridin-4-yl-propan-1-one (commercial), 2-bromo-1-pyrimidin-4-yl-ethanone (reported in WO2005014572), 1-(2-amino-pyrimidin-4-yl)-2-bromo-ethanone (commercial), 2-bromo-1-(2-chloro-pyridin-4-yl)-ethanone (reported in WO2004058762), 2-bromo-1-(2-methylsulfanyl-pyrimidin-4-yl)-ethanone (reported in WO2003011838), 1-(2-amino-5-fluoro-pyrimidin-4-yl)-2-bromo-ethanone 1'A (Scheme 2.1.) and 2-bromo-1-(2-phenylamino-pyrimidin-4-yl)-ethanone 1"A (Scheme 2.2.).

Among the suitable heteroaryl-ethanone derivatives subdued to halogenation we consider, for instance, 1-(3-fluoro-pyridin-4-yl)ethanone (commercial), 1-(2-chloropyridin-4-yl)ethanone (commercial), 1-(pyrimidin-4-yl)ethanone (commercial), 1-[2-(methylthio)pyrimidin-4-yl]ethanone (commercial) and 4-(1-ethoxy-vinyl)-5-fluoro-pyrimidin-2-ylamine iii (see Scheme 2.1.).

Intermediate 1-(2-amino-5-fluoro-pyrimidin-4-yl)-2-bromo-ethanone 1'A (1A, wherein $R_4$=H, $R_5$=F, G=N, $R_6$=$NH_2$, X=Br) can be obtained according to the following reaction sequence (Scheme 2.1.):

Scheme 2.1.

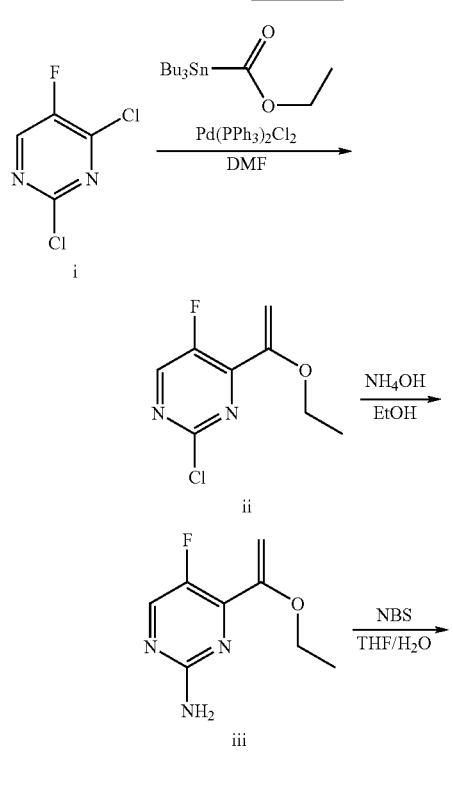

Commercially available 2,4-dichloro-5-fluoro-pyrimidine i is reacted with (1-ethoxyvinyl)-tributylstannane in standard conditions in the presence of a palladated catalyst (for example dichloroditriphenylphosphino palladium) in DMF, to afford the corresponding 4-vinyl ether ii. The amino group can be introduced at position 2 by direct treatment with aqueous concentrated ammonia in ethanol and heating with microwaves (iii), while bromination of the vinyl ether to the α-bromo-ketone (1'A) is achieved with NBS in aqueous solvents.

Among the silylenolethers subdued to halogenation, we consider, for instance, (tert-butyl-dimethyl-silanyl)-{4-[1-(tert-butyl-dimethyl-silanyloxy)-vinyl]-pyrimidin-2-yl}-phenyl-amine iv (reported in WO2005014572), from which bromoketone 1"A (1A, wherein $R_4=R_5=H$, G=N, $R_6$=NHAr, X=Br) can be obtained according to the reaction step shown in Scheme 2.2.

Scheme 2.2.

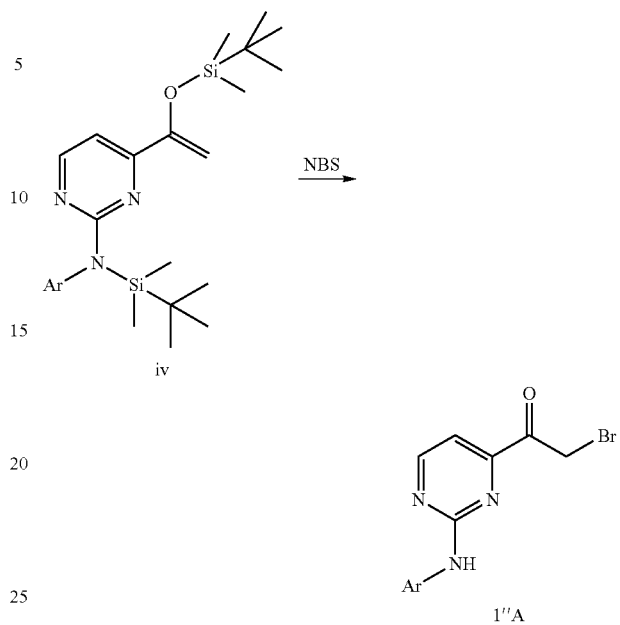

wherein Ar represents an aryl group as defined above.

Halogenation of the compound of formula (Iv) may be promptly obtained with N-bromo succinimide in aqueous tetrahydrofuran at rt for about 20 h. The compounds of formula 1B, when not commercially available, may be prepared with different methods according to references in the literature. For instance, acid homologation to beta-keto esters may be achieved from acyl chlorides or carboxylic acids by activation with 2,2-dimethyl-1,3-dioxane-4,6-dione (the Meldrum's acid) as described in *J. Med. Chem.* 2001, 44, 90, from acyl chlorides and ethyl hydrogenmalonate as reported in *J. Het. Chem.* 1990, 27, 1609, or from aryl ethanones with diethylcarbonate as shown in *Can. J. Chem.* 1992, 1323.

Alternatively, a compound of formula (I) as defined above, may be obtained by a') coupling a compound of formula 2D

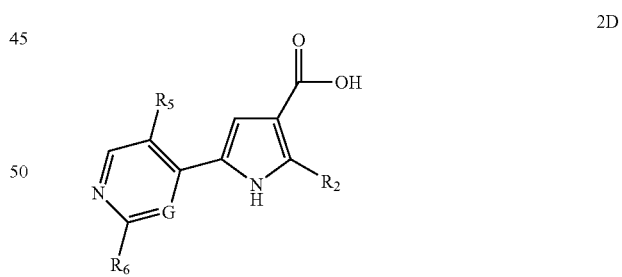

wherein $R_2$ is hydrogen or halogen atom, and $R_5$, $R_6$, and G are as defined above, either with an activated form of ammonia, optionally in the presence of a condensing agent, or with an amine of formula $R_3$—$NH_2$, wherein $R_3$ is as defined above, thus obtaining a compound of formula (I) as defined above wherein W is N, $R_1$ is hydrogen atom and $R_2$ is hydrogen atom or halogen atom;

$a'_1$) optionally converting the resultant compound of formula (I) wherein $R_2$ is halogen atom into another compound of formula (I) wherein $R_2$ is hydrogen atom or an optionally substituted group selected form aryl, cycloalkyl and heterocyclyl group as defined above; and/or a'$_2$) converting the resultant compound of formula (I) wherein R$_1$ is hydrogen atom into another compound of formula (I) wherein R$_1$ is an optionally substituted group selected from alkyl, cycloalkyl, alkenyl, alkynyl, heterocyclyl, aryl, heterocyclyloxy-alkyl and alkoxycarbonyl;

and, if desired, converting a compound of formula (I) into a pharmaceutically acceptable salt thereof or converting a salt into the free compound (I).

The starting material of formula 2D is prepared via a Pinner-like reaction as shown in the following Scheme 3, analogously or accordingly to methods reported in the literature (for instance *Il Farmaco* 1999, 54, 542 or *Tetrahedron Letters* 1994, 35, 5989).

Scheme 3

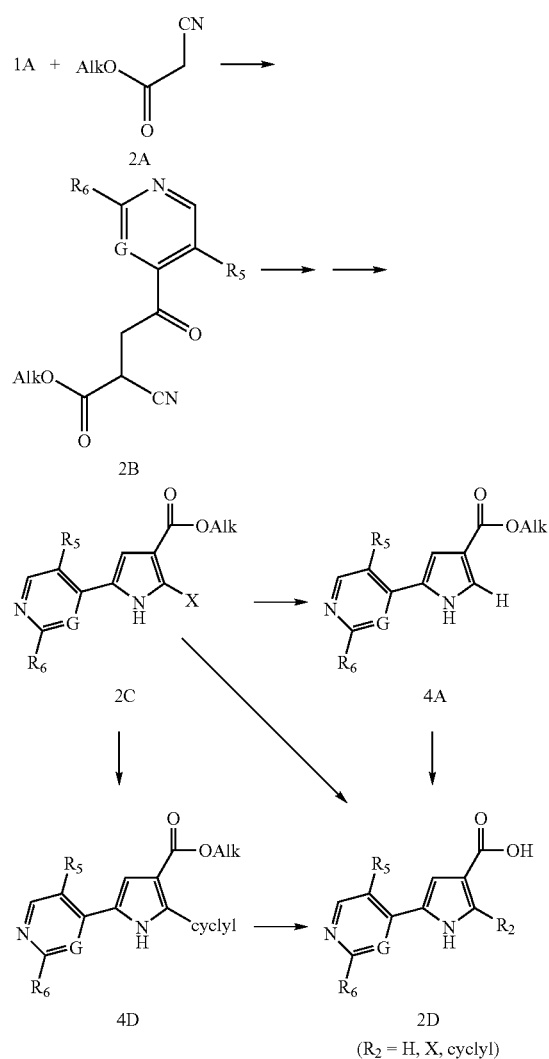

wherein R$_5$, R$_6$, X, G, cyclyl and Alk are as defined above.

Compound 2B may be formed by treating haloketone 1A, as defined above, with cyanoester 2A in the presence of a suitable base, such as sodium ethoxide in ethanol, at temperatures ranging from rt to reflux, for periods of time from about 1 h to 16 h.

Halopyrrole 2C may be obtained by exposing 2B to halohydric acids, such as hydrochloric acid in dioxane or hydrobromic acid in acetic acid, in a solvent like dichloromethane or diethylether or mixtures thereof at temperatures ranging from −20° C. to reflux, most frequently at rt. Access to 2-unsubstituted pyrroles can be achieved by dehalogenation of halopyrrole 2C that may be accomplished, for instance, by hydrogenolysis, to give 4A.

Alternatively, functionalization at position 2 may be accomplished on haloester 2C to yield ester 4D. Esters 2C, 4A and 4D may be then saponified in standard basic conditions to the corresponding acids 2D.

Alternatively, a compound of formula (I) as defined above, may be obtained by a') cleaving a compound of formula 3A or 3B

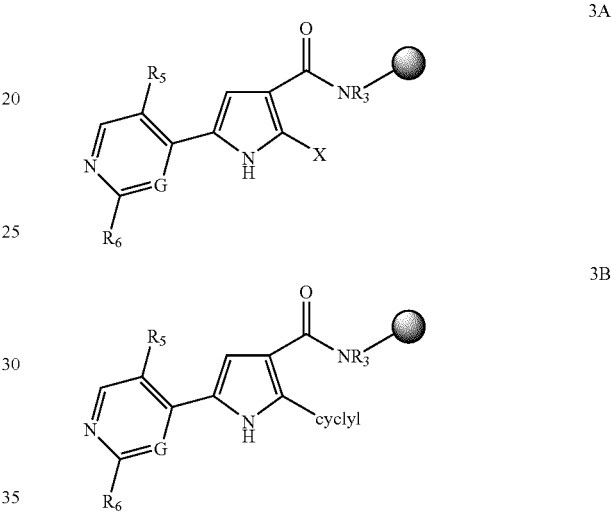

wherein R$_3$, R$_5$, R$_6$, cyclyl, X, G are as defined above and the symbol represents a solid support to which the chemical molecule is linked, and, if desired, converting the resultant compound of formula (I) wherein W is nitrogen atom and R$_2$ is halogen or an optionally substituted group selected form aryl, cycloalkyl and heterocyclyl group, into a pharmaceutically acceptable salt thereof or converting a salt into the free compound (I).

The cleavage is preferably accomplished with TFA/DCM.

The above preparation is aimed at avoiding the formation of unwanted by-products. The preparation of compounds 3A and 3B is displayed in Scheme 4. Acid 2D is loaded onto a solid support, such as a resin (for example a Rink amide MBHA resin, previously cleaved by shaking at rt in a 20% piperidine solution in DMF) by stirring at rt overnight in DMF in the presence of EDCI and HOBT to form amide 3A on which a carbon-carbon bond forming reaction, for instance the Suzuki reaction, is successfully applied to give the compound of formula 3B.

Scheme 4

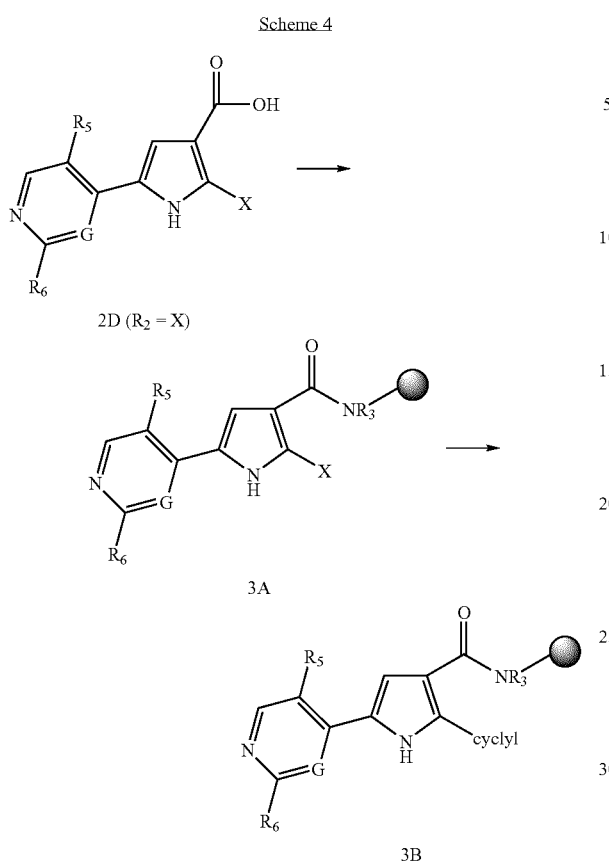

wherein $R_3$, $R_5$, $R_6$, X, G, and cyclyl are as defined above.

A particular compound of formula 1D, named 6D, wherein the cyclyl bears a substituent may be optionally converted into different compound of formula 1D, named 7D, as represented in Scheme 5.

Scheme 5

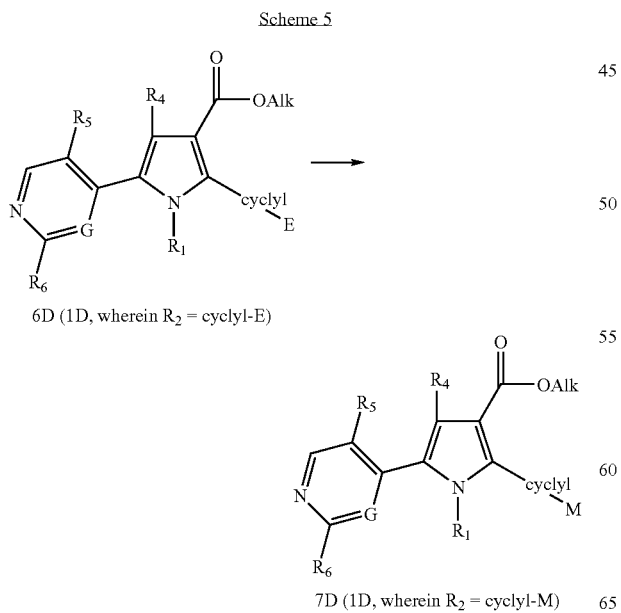

wherein $R_1$, $R_4$, $R_5$, $R_6$, G, cyclyl and Alk are as defined above, E is halogen, triflate, mesilate or tosylate group, and M is aryl, heteroaryl, heterocyclyl, alkenyl, alkynyl, or optionally substituted amino moieties.

A particular cyclyl moiety, namely a suitably substituted aryl or heterocyclyl ring, bearing a substituent E as above defined, may be subdued to carbon-carbon or carbon-nitrogen bond formation with an array of well known methods from the literature, for example the Suzuki, Stille, Sonogashira or Buchwald protocols, able to produce the desired outcome 7D, where the group M is as above defined.

Moreover, the present invention provides a process comprising:

a) coupling a compound of formula 7B

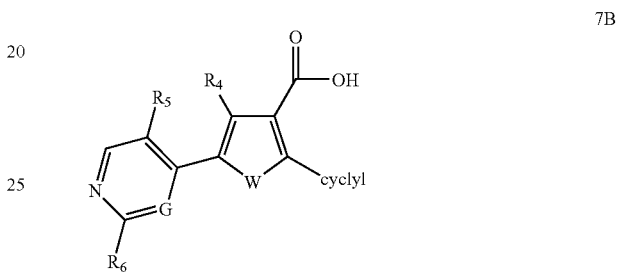

wherein W is an oxygen or sulphur atom, $R_4$, $R_5$, $R_6$ and G are as defined above and cyclyl is an optionally substituted group selected form aryl, cycloalkyl and heterocyclyl group as defined above, either with an activated form of ammonia, optionally in the presence of a condensing agent, or with an amine of formula $R_3$—$NH_2$, wherein $R_3$ is as defined above, thus obtaining a compound of formula (I) as defined above, wherein W is an oxygen or sulphur atom, and $R_2$ is an optionally substituted group selected form aryl, cycloalkyl and heterocyclyl group;

b) optionally converting a compound of formula (I) into another different compound of formula (I), and, if desired, converting a compound of formula (I) into a pharmaceutically acceptable salt thereof or converting a salt into the free compound (I).

Under optional step b), when W is sulphur atom, thiophene ring may be oxidized to the corresponding 1-oxo or 1,1-dioxo thiophenes by well known procedures from the literature.

The esters of general formula 7A, belonging to the thiophene and furan series, may be conveniently obtained in mixture from ketoesters 1C by cyclization, for instance with 2,4-bis(4-methoxyphenyl)-1,3-dithia-2,4-diphosphetane-2,4-disulfide (the Lawesson's reagent).

After chromatographic separation the two esters may be independently subdued to standard basic hydrolysis providing the desired acids 7B (Scheme 6).

Scheme 6

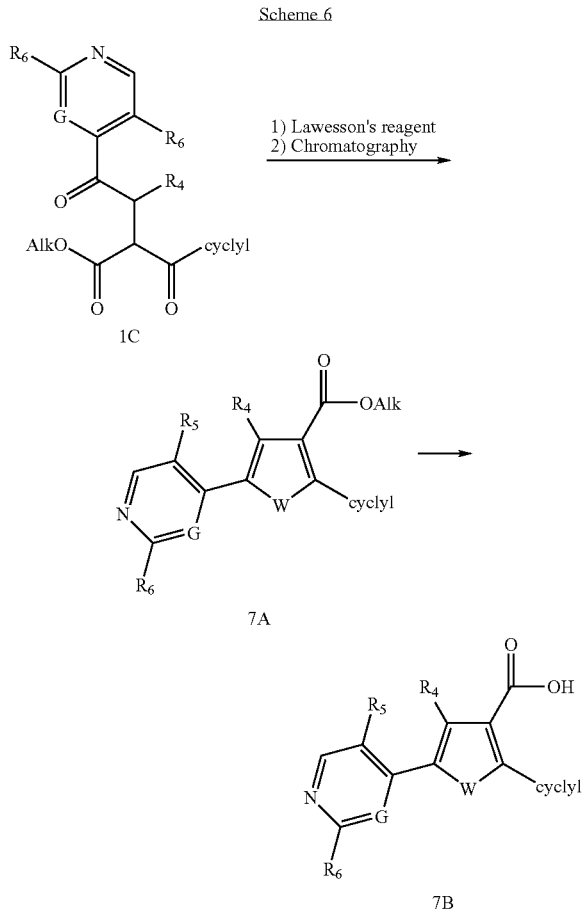

wherein $R_4$, $R_5$, $R_6$, G, W, cyclyl and Alk are as defined above.

As stated above, optionally the compounds of formula (I) may be directly modified at either of their heteroaromatic component generating another derivative of formula (I). For instance the pyrimidine ring of pyrrole 8A can be directly halogenated to yield amides 8B and 8C. This transformation is achieved respectively by treatment with NCS at about 100° C. or with NBS at room temperature in a suitable solvent, like, for example, THF or DMF. Alternatively, NIS in the same conditions transforms amide 8A into the corresponding amide 8D, halogenated at position 4 of pyrrole. The same amide 8A, if previously protected at the aminopyrimidine nucleus as Boc derivative, can be also transformed in chloro amide 8E by treatment with NCS at 100° C. in DMF and deprotection in standard acidic conditions. Both double sequential and double simultaneous halogenations can also be achieved, as shown in Scheme 7. Bromo amide 8C, when treated with NIS, affords amide 8F and the same result is obtained by treating iodo amide 8D with NBS. Amide 8A is simultaneously dihalogenated by two equivalents of halogenating agent to provide amides 8G and 8H, upon treatment with NBS and NIS respectively. Amide 8D can be transformed into the 4-vinyl derivative 8K by direct vinylation via the Stille cross-coupling reaction protocol, as described, for example, in *Tetr. Lett.* 1995, 36, 7043. The reaction occurs by treating 8D with vinyltributylstannane in the presence of a palladated catalyst, such as palladium tetrakis or dichloroditriphenylphosphino palladium, in solvents like dioxane, DMF or their mixtures, at temperatures ranging from 25 to 200° C.

Scheme 7

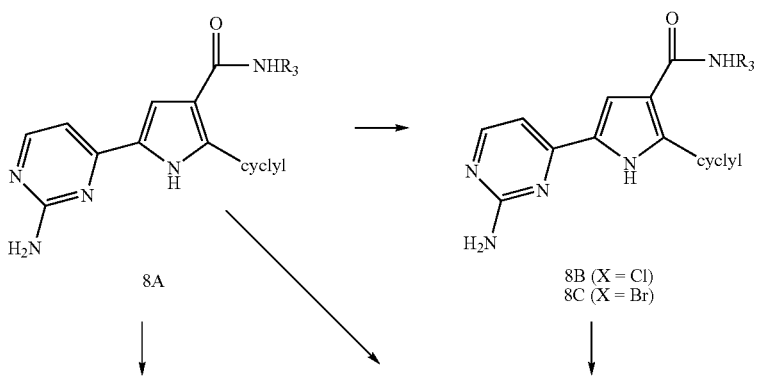

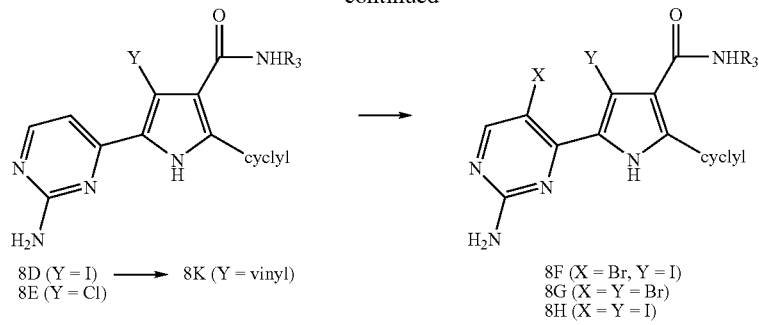

8D (Y = I) → 8K (Y = vinyl)
8E (Y = Cl)

8F (X = Br, Y = I)
8G (X = Y = Br)
8H (X = Y = I)

wherein $R_3$, $R_5$, $R_6$, X, G and cyclyl are as defined above.

Another process for preparing a compound of formula (I) comprises:

a) reacting a compound of formula 9

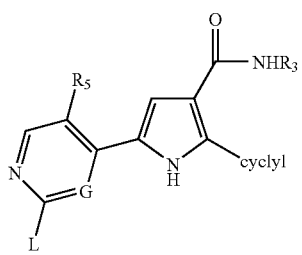

9 wherein L is a leaving group such as halogen, methansulphonyl or methansulfinyl and $R_3$, $R_5$, cyclyl and G are as defined above, either with an activated form of ammonia, like lithium bis(trimethylsilyl)amide, optionally in the presence of a condensing agent, or with hydrazine followed by reduction to amine, or with an amine of formula $R_7$—$NH_2$, wherein $R_7$ is as defined above, in a Pd-catalyzed coupling, thus obtaining a compound of formula (I) as defined above wherein W is $NR_1$, $R_1$ is hydrogen atom and $R_6$ is NH—$R_7$;

and, if desired, converting a compound of formula (I) into a pharmaceutically acceptable salt thereof or converting a salt into the free compound (I).

The starting compounds 9 of this process are shown in Scheme 8.

Halopyridine 9, wherein L is halogen (9A) may be obtained, for example, from 2-bromo-1-(2-chloro-pyridin-4-yl)-ethanone prepared by halogenation of 1-(2-chloropyridin-4-yl)ethanone, obtainable from 2-chloro-4-cyano pyridine, as described in J. Het. Chem., 1983, 20, 533. 1-[2-(Methylthio)pyrimidin-4-yl] derivative 9, wherein L is $CH_3$—S— (9B), obtainable from 2-bromo-1-(2-methylsulfanyl-pyrimidin-4-yl)-ethanone (described in WO03/011838), may be activated to the corresponding sulfoxide or sulfone 9, wherein L is $CH_3$—S(O)— or $CH_3$—S(O)$_2$— (9D), by oxidation, for example with oxone. Halopyrimidine derivative 9, wherein L is halogen and $R_5$ is fluorine (9C), may be instead prepared from 2-bromo-1-(2-chloro-5-fluoropyrimidin-4-yl) ethanone, obtained by halogenation of 1-(2-chloro-5-fluoropyrimidin-4-yl)ethanone, in turn prepared as described in WO04/058762.

Scheme 8

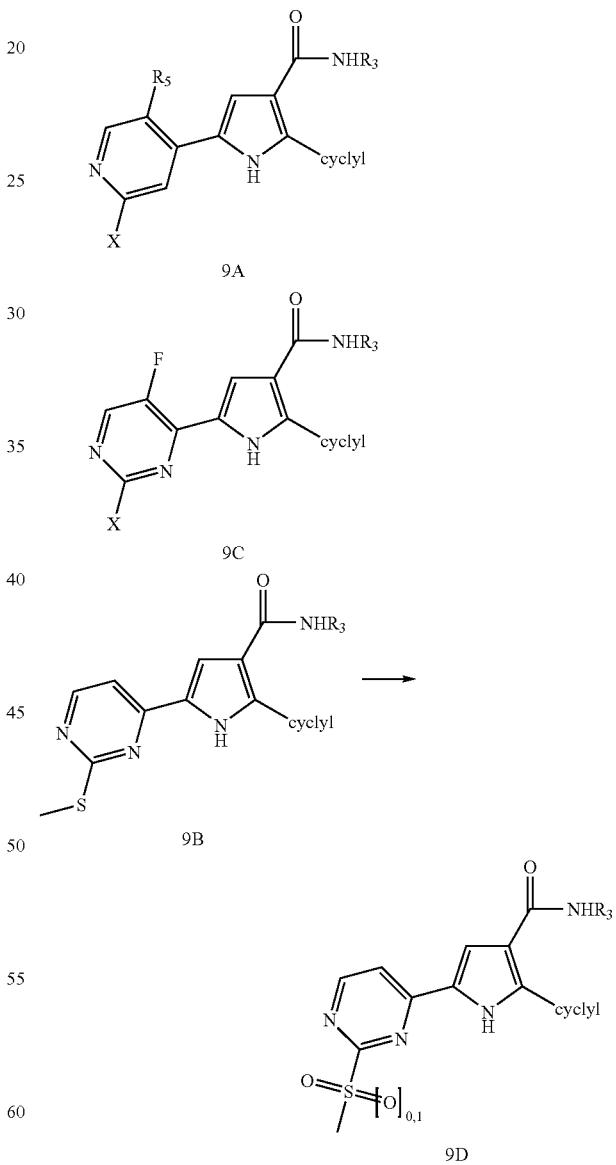

wherein $R_3$, $R_5$, X and cyclyl are as defined above.

It is a further object of the present invention an intermediate of the formula 1D or 1E:

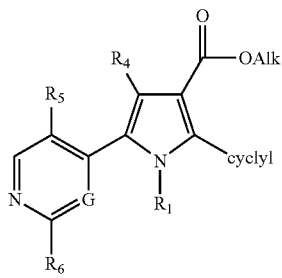

1D

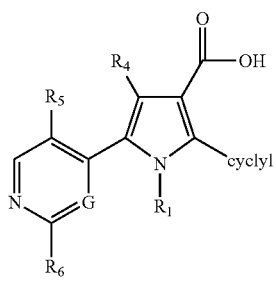

1E wherein G, Alk, cyclyl, $R_1$, $R_4$, $R_5$ and $R_6$ are as defined above, with the proviso that the following compounds are excluded:

1H-Pyrrole-3-carboxylic acid, 1-(methoxymethyl)-4-methyl-2,5-di-4-pyridinyl-, ethyl ester;

1H-pyrrole-3-carboxylic acid, 2,5-di-4-pyridinyl-, methyl ester, 1H-pyrrole-3-carboxylic acid, 4-methyl-2-phenyl-5-(4-pyridinyl)-, methyl ester, 1H-pyrrole-3-carboxylic acid, 4-methyl-2,5-di-4-pyridinyl-, compd. with morpholine (1:1), 1H-pyrrole-3-carboxylic acid, 4-methyl-2,5-di-4-pyridinyl, 1H-pyrrole-3-carboxylic acid, 4-(methoxymethyl)-2,5-di-4-pyridinyl-, methyl ester, 1H-pyrrole-3-carboxylic acid, 4-butyl-2,5-di-4-pyridinyl-, ethyl ester, 1H-pyrrole-3-carboxylic acid, 4-(1-methylethyl)-2,5-di-4-pyridinyl-, ethyl ester, 1H-pyrrole-3-carboxylic acid, 4-propyl-2,5-di-4-pyridinyl-, ethyl ester, 1H-pyrrole-3-carboxylic acid, 4-methyl-2,5-di-4-pyridinyl-, 2-methoxyethyl ester, 1H-pyrrole-3-carboxylic acid, 4-methyl-2,5-di-4-pyridinyl-, butyl ester, 1H-pyrrole-3-carboxylic acid, 4-methyl-2,5-di-4-pyridinyl-, propyl ester, 1H-pyrrole-3-carboxylic acid, 4-methyl-2,5-di-4-pyridinyl-, 1,1-dimethylethyl ester, 1H-pyrrole-3-carboxylic acid, 4-methyl-2,5-di-4-pyridinyl-, 1-methylethyl ester, 1H-pyrrole-3-carboxylic acid, 4-methyl-2,5-di-4-pyridinyl-, 2-propenyl ester, 1H-pyrrole-3-carboxylic acid, 4-methyl-2,5-di-4-pyridinyl-, phenylmethyl ester, 1H-pyrrole-3-carboxylic acid, 4-methyl-2,5-di-4-pyridinyl-, methyl ester, 1H-pyrrole-3-carboxylic acid, 4-methyl-2,5-di-4-pyridinyl-, ethyl ester and 1H-pyrrole-3-carboxylic acid, 4-ethyl-2,5-di-4-pyridinyl-, ethyl ester.

Pharmacology

The compounds of formula (I) are active as protein kinase inhibitors and are therefore useful, for instance, to restrict the unregulated proliferation of tumor cells.

In therapy, they may be used in the treatment of various tumors, such as those formerly reported, as well as in the treatment of other cell proliferative disorders such as psoriasis, vascular smooth cell proliferation associated with atherosclerosis and post-surgical stenosis and restenosis and in the treatment of Alzheimer's disease.

Inhibition Assay of Cdc7 Activity

The inhibiting activity of putative Cdc7 inhibitors and the potency of selected compounds is determined through a method of assay based on the use of Dowex resin capture technology.

The assay consists of the transfer of radioactivity labeled phosphate moiety by the kinase to an acceptor substrate. The resulting 33P-labeled product is separated from unreacted tracer, transferred into a scintillation cocktail and light emitted is measured in a scintillation counter.

The inhibition assay of Cdc7/Dbf4 activity is performed according to the following protocol.

The MCM2 substrate is trans-phosphorylated by the Cdc7/Dbf4 complex in the presence of ATP traced with $\gamma^{33}$-ATP. The reaction is stopped by addition of Dowex resin in the presence of formic acid. Dowex resin particles capture unreacted $\gamma^{33}$-ATP and drag it to the bottom of the well while $^{33}$P phosphorylated MCM2 substrate remains in solution. The supernatant is collected, transferred into Optiplate plates and the extent of substrate phosphorylation is evaluated by $\beta$ counting.

The inhibition assay of Cdc7/Dbf4 activity was performed in 96 wells plate according to the following protocol.

To each well of the plate were added:
- 10 µl test compound (10 increasing concentrations in the nM to uM range to generate a dose-response curve). The solvent for test compounds contained 3% DMSO. (final concentration 1%)
- 10 µl substrate MCM2 (6 µM final concentration), a mixture of cold ATP (2 µM final concentration) and radioactive ATP (1/5000 molar ratio with cold ATP).
- 10 µl enzyme (Cdc7/Dbf4, 2 nM final concentration) that started the reaction. The buffer of the reaction consisted in 50 mM HEPES pH 7.9 containing 15 mM $MgCl_2$, 2 mM DTT, 3 uM $NaVO_3$, 2 mM glycerophosphate and 0.2 mg/ml BSA.

After incubation for 60 minutes at room temperature, the reaction was stopped by adding to each well 150 µl of Dowex resin in the presence of 150 mM formic acid.

After another 60 min incubation, 50 µL of suspension were withdrawn and transferred into 96-well OPTIPLATEs containing 150 µl of MicroScint 40 (Packard); after 5-10 minutes shaking the plates were read for 1 min in a Packard TOP-Count radioactivity reader.

IC50 determination: inhibitors were tested at different concentrations ranging from 0.0005 to 10 µM. Experimental data were analyzed by the computer program Assay Explorer using the four parameter logistic equation:

$$y = \text{bottom} + (\text{top}-\text{bottom})/(1+10^{((\log IC50-x)*\text{slope})})$$

where x is the logarithm of the inhibitor concentration, y is the response; y starts at bottom and goes to top with a sigmoid shape.

The compounds of formula (I) of the present invention showed $IC_{50}$ values on Cdc7/Dbf4 between 1 and 1000 nM. In particular, the compounds coded A1, A2, A3, A4, A5, A6, A7, A8, A9, A10, A11, A12, A20, C1, C2, E1, F1, G1, H1, L1, M2, M3, M4, here below, showed $IC_{50}$ values on Cdc7/Dbf4 between 1 and 100 nM.

In addition the selected compounds have been characterized for specificity on a panel of many other kinases, among which Cdk2A, IGF1-R, Aurora-2, AKT1, PLK1, SULU1, ERK2, CK2, GSK3β, PKAα, PKCβ, VEGFR3, PDGFR.

Inhibition Assay of Cdk2/Cyclin A Activity

Kinase reaction: 1.5 µM histone H1 substrate, 25 µM ATP (0.2 µCi P33γ-ATP), 30 ng of baculovirus co-expressed Cdk2/Cyclin A, 10 µM inhibitor in a final volume of 100 µl buffer (TRIS HCl 10 mM pH 7.5, $MgCl_2$ 10 mM, 7.5 mM DTT) were added to each well of a 96 U bottom well plate. After 10 min at 37° C. incubation, reaction was stopped by 20 µl EDTA 120 mM.

Capture: 100 µl were transferred from each well to Multi-Screen plate, to allow substrate binding to phosphocellulose filter. Plates were then washed 3 times with 150 µl/well PBS $Ca^{++}/Mg^{++}$ free and filtered by MultiScreen filtration system.

Detection: filters were allowed to dry at 37° C., then 100 µl/well scintillant were added and 33P labeled histone H1 was detected by radioactivity counting in the Top-Count instrument.

Results: data were analyzed and expressed as % inhibition referred to total activity of enzyme (=100%).

All compounds showing inhibition ≧50% were further analyzed in order to study and define potency (IC50) as well as the kinetic-profile of inhibitor through Ki calculation.

IC50 determination: the protocol used was the same described above, where inhibitors were tested at different concentrations ranging from 0.0045 to 10 µM. Experimental data were analyzed by the computer program GraphPad Prizm using the four parameter logistic equation:

$$y = \text{bottom} + (\text{top} - \text{bottom})/(1 + 10^{((\log IC50 - x) \cdot \text{slope})})$$

where x is the logarithm of the inhibitor concentration, y is the response; y starts at bottom and goes to top with a sigmoid shape.

Ki calculation: either the concentration of ATP and histone H1 substrate were varied: 4, 8, 12, 24, 48 µM for ATP (containing proportionally diluted $P^{33}$γ-ATP) and 0.4, 0.8, 1.2, 2.4, 4.8 µM for histone were used in absence and presence of two different, properly chosen inhibitor concentrations.

Experimental data were analyzed by the computer program "SigmaPlot" for Ki determination, using a random bireactant system equation:

$$v = \frac{V\max \frac{(A)(B)}{aKAKB}}{1 + \frac{(A)}{KA} + \frac{(B)}{KB} + \frac{(A)(B)}{aKAKB}}$$

where A=ATP and B=histone H1.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 10 to about 1000 mg per dose, from 1 to 10 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim to better illustrate the present invention, without posing any limitation to it, the following examples are now given.

EXAMPLES

For a reference to any specific compound of formula (I) of the invention, optionally in the form of a pharmaceutically acceptable salt, see the experimental section and claims.

Referring to the examples that follow, compounds of the present invention were synthesized using the methods described herein, or other methods, which are well known in the art.

General Methods

Flash Chromatography was performed on silica gel (Merck grade 9395, 60A). Where specified, chromatographic separations have been performed on a Biotage Horizon system. Microwave-assisted reactions were performed using Biotage/PersonalChemistry SmithCreator™.

HPLC was performed on Waters X Terra RP 18 (4.6×50 mm, 3.5 µm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid/acetonitrile 95:5), and Mobile phase B was $H_2O$/acetonitrile (5:95). Gradient from 10 to 90% B in 8 minutes, hold 90% B 2 minutes. UV detection at 220 nm and 254 nm. Flow rate 1 m/min. Injection volume 10 µL. Full scan, mass range from 100 to 800 amu. Capillary voltage was 2.5 KV; source temp. was 120° C.; cone was 10 V. Retention times (HPLC r.t.) are given in minutes at 220 nm or at 254 nm. Mass are given as m/z ratio.

When necessary, compounds have been purified by preparative HPLC:
- on a Waters Symmetry C18 (19×50 mm, 5 µm) column using a Waters preparative HPLC 600 equipped with a 996 Waters PDA detector and a Micromass mod. ZMD single quadrupole mass spectrometer, electron spray ionization, positive mode. Mobile phase A was water 0.01% TFA, and Mobile phase B was acetonitrile. Gradient from 10 to 90% B in 8 min, hold 90% B 2 min. Flow rate 20 mL/min.
- on a Waters X Terra Prep RP18 (19×100 mm, 5 µm) column using a Waters FractionLynx System (FL2) equipped with a Waters 2996 PDA UV-VIS detector and a Waters ZQ single quadrupole mass spectrometer. Mobile phase A was 0.05% $NH_4OH$ in $H_2O$ pH10/Acetonitrile 95/5, and Mobile phase B was acetonitrile. Gradient from 0 to 80% B in 8 min, hold 100% B 2 min. Flow rate 20 mL/min.

Low-resolution mass spectral (MS) data were determined on a Finnigan MAT LCQ ion trap instrument, equipped with an electrospray (ESI) ion source. High-resolution mass spectra (HRMS) were obtained on a Waters Q-TOF Ultima instrument, equipped with an electrospray (ESI) ion source, and using Reserpine (MW 609.28065) for Lock Mass correction. Unless differently reported, $^1$H-NMR spectrometry was performed on a Mercury VX 400 operating at 400.45 MHz equipped with a 5 mm double resonance probe [1H (15N-31P) ID_PFG Varian]. Chemical shifts are expressed as δ (ppm).

In these examples and elsewhere, abbreviations have the following meanings:
AcOH=acetic acid
$AcONH_4$=ammonium acetate
aq=aqueous
Boc=tert-butoxycarbonyl
$^t$BuONa=sodium tert-butoxide
CDI=N,N'-carbonyldiimidazole
$CH_3CN$=acetonitrile
$ClSO_2NCO$=chlorosulfonyl isocyanate
conc=concentrated
$Cs_2CO_3$=cesium carbonate
DCM=dichloromethane
DIEA=diisopropylethylamine
DMAP=dimethylaminopyridine
DMF=N,N'-dimethylformamide
DMSO-D6=deuterated dimethylsulfoxide
EDCI=1-(3-dimethylaminopropyl)-3-ethylcarbodiimide hydrochloride
eq=equivalents
ESI=electrospray ionization
EtI=ethyl iodide
$EtNH_2$=ethylamine
EtOAc=ethyl acetate
EtOH=ethanol
$Et_2O$=diethylether
g=grams
h=hour(s)
HBr=hydrobromic acid
HCl=hydrochloric acid
HCOOH=88% formic acid
$HCOONH_4$=ammonium formate
HOBT=hydroxybenzotriazole
$HOBT.NH_3$=hydroxybenzotriazole ammonium salt
HPLC=high performance liquid chromatography
KOH=potassium hydroxide
Lawesson's reagent=2,4-bis(4-methoxyphenyl)-1,3-dithia-2,4-diphosphetane-2,4-disulfide
LiCl=lithium chloride
M=molar
MBHA resin=4-methylbenzhydrylamine-resin hydrochloride
Meldrum's acid=2,2-dimethyl-1,3-dioxane-4,6-dione
$MeNH_2$=methylamine
MeOH=methanol
mg=milligrams
min=minutes
mL=milliliters
mmol=millimoles
mol=moles
N=normal
$Na_2CO_3$=sodium carbonate
NaH=sodium hydride, 60% in mineral oil
$NaHCO_3$=sodium hydrogen carbonate
$NaH_2PO_4$=sodium dihydrogen phosphate
$NaNO_2$=sodium nitrite
NaOH=sodium hydroxyde
$Na_2SO_4$=anhydrous sodium sulphate
NBS=N-bromo-succinimide
NCS=N-chloro-succinimide
NIS=N-iodo-succinimide
$NH_3$=ammonia
$Pd(OAc)_2$=palladium acetate
$(Ph_3P)_2PdCl_2$=dichlorobis(triphenylphosphine)palladium (II)
rt=room temperature TBTU=O-benzotriazol-1-yl-N,N,N',N'-tetramethyluronium tetrafluoroborate
TEA=triethylamine
TFA=trifluoroacetic acid
THF=tetrahydrofuran
Xantphos=9,9-dimethyl-9H-xanthene-4,5-diyl)bis[diphenylphosphine]
μL=microliters Example 1

2-Phenyl-5-pyridin-4-yl-1H-pyrrole-3-carboxylic Acid Amide (A1)

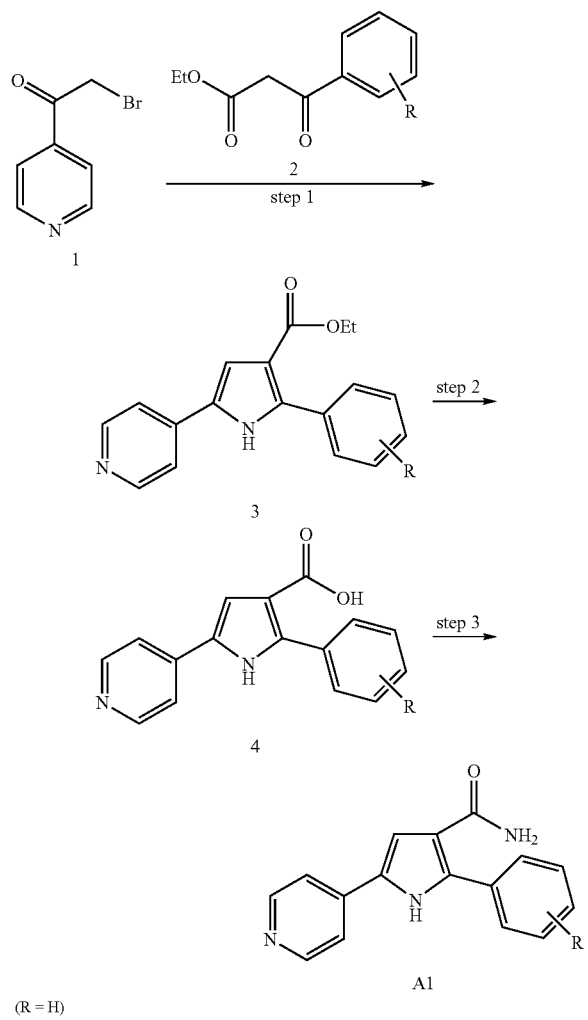

(R = H)

Step 1: Formation of Pyrrole Ring (3)

2-Bromo-1-pyridin-4-ylethanone hydrobromide 1 (1.7 g, 6.2 mmol) was added to a mixture of 3-oxo-3-phenyl-propionic acid ethyl ester 2 (R=H, 1 g, 5.2 mmol) in 100 mL of dry THF and NaH (0.5 g, 13.0 mmol) at 0° C. The solution was left at 0° C. for 1 h and then stirred at rt for 3 h. The solvent was removed and the residue was dissolved in 60 ml of EtOH, ammonium acetate (1.4 g, 18.7 mmol) was added and the reaction mixture was left overnight at rt. The crude material was purified by flash chromatography (DCM/MeOH 98:2) affording 920 mg (60%) of 2-phenyl-5-pyridin-4-yl-1H-pyrrole-3-carboxylic acid ethyl ester as a solid.

$^1$H NMR (DMSO-d$_6$/400 MHz) δ ppm 1.20 (t, J=7.08 Hz, 3H), 4.16 (q, J=7.08 Hz, 2H), 7.30 (d, J=2.81 Hz, 1H), 7.43 (m, 3H), 7.64 (m, 2H), 7.79 (m, 2H), 8.53 (m, 2H), 12.12 (s, 1H); ESI (+) MS: m/z 293 (MH$^+$).

Step 2: Saponification to Carboxylic Acids (4)

Ester 3 (440 mg, 1.5 mmol) in 3 mL of EtOH and 3 mL of 4M aq NaOH was heated at 100° C. for 3 h. The reaction mixture was cooled at 0° C. and acidified with conc HCl observing precipitation of the product which was filtered, washed with a little amount of water and acetone and dried leading to 400 mg (88%) of 2-phenyl-5-pyridin-4-yl-1H-pyrrole-3-carboxylic acid as a solid that was used in the next step without further purification.

$^1$H NMR (DMSO-d$_6$/400 MHz) δ ppm 7.51 (m, 3H), 7.68 (m, 2H), 7.75 (d, J=2.44 Hz, 1H), 8.28 (d, J=6.65 Hz, 2H), 8.74 (d, J=6.65 Hz, 2H), 12.51 (s, 1H); MS: m/z 263 [M-H].

Step 3: Condensation to Amides (A1)

Acid 4 (380 mg, 1.44 mmol) was dissolved in 10 mL of dry THF in the presence of DIEA (0.5 mL, 2.90 mmol). To the solution, cooled at 0° C., EDCI (414 mg, 2.16 mmol) and HOBT-NH$_3$ (330 mg, 2.16 mmol) were added. The reaction mixture was left overnight at rt. The solvent was removed, water was added and the slurry was extracted with DCM. The organic layer was dried (Na$_2$SO$_4$), the solvent was evaporated and the crude was purified by flash chromatography (DCM/MeOH 95:5) to give 150 mg (40%) of 2-phenyl-5-pyridin-4-yl-1H-pyrrole-3-carboxylic acid amide as a pale yellow solid.

$^1$H NMR (DMSO-d$_6$/400 MHz) δ ppm 6.90 (bs, 2H), 7.27 (d, J=2.56 Hz, 1H), 7.37 (m, 1H), 7.44 (m, 2H), 7.67-7.71 (m, 4H), 8.53 (m, 2H), 11.82 (s, 1H); ESI (+) MS: m/z 264 (MH$^+$).

The above procedure was employed to synthesize the following compounds:

Example 2

Step-1

2-(2-Fluoro-phenyl)-5-pyridin-4-yl-1H-pyrrole-3-carboxylic Acid Ethyl Ester $^1$H NMR (DMSO-d$_6$/400 MHz) δ ppm 1.11 (t, J=7.07 Hz, 3H) 4.09 (t, J=7.07 Hz, 2H) 7.28-7.34 (m, 5H) 7.75 (dd, J=1.46, 4.63 Hz, 2H) 8.52 (m, 2H) 12.31 (s, 1H); ESI (+) MS: m/z 311 (MH$^+$).

Example 2

Step-2

2-(2-Fluoro-phenyl)-5-pyridin-4-yl-1H-pyrrole-3-carboxylic Acid $^1$H NMR (DMSO-d$_6$/400 MHz) δ ppm 7.33 (m, 4H) 7.72 (d, J=2.56 Hz, 1H) 8.22 (d, J=6.40 Hz, 2H) 8.72 (m, 2H) 12.73 (s, 1H); MS: m/z 281 [M-H].

Example 2

Step-3

2-(2-Fluoro-phenyl)-5-pyridin-4-yl-1H-pyrrole-3-carboxylic Acid Amide Hydrochloride (A2)

$^1$H NMR (DMSO-$d_6$/400 MHz) δ ppm 7.00 (bs, 2H), 7.29-7.36 (m, 4H), 7.73 (d, J=2.43 Hz, 1H), 8.11 (d, J=6.59 Hz, 2H), 8.74 (d, J=6.59 Hz, 2H), 12.56 (s, 1H); ESI (+) MS: m/z 282 (MH$^+$).

Example 3

Step-1

2-(3-Fluoro-phenyl)-5-pyridin-4-yl-1H-pyrrole-3-carboxylic Acid Ethyl Ester

$^1$H NMR (DMSO-$d_6$/400 MHz) δ ppm 1.20 (t, J=7.10 Hz, 3H) 4.15 (q, J=7.10 Hz, 2H) 7.27 (m, 1H) 7.30 (d, J=2.81 Hz, 1H), 7.49-7.53 (m, 3H) 7.78 (m, 2H) 8.53 (d, J=5.13 Hz), 12.17 (s, 1H); ESI (+) MS: m/z 311 (MH$^+$).

Example 3

Step-2

2-(3-Fluoro-phenyl)-5-pyridin-4-yl-1H-pyrrole-3-carboxylic Acid

$^1$H NMR (DMSO-$d_6$/400 MHz) δ ppm 0.25 (m, 1H) 7.31 (d, J=2.9 Hz, 1H) 7.40 (m, 3H) 7.80 (m, 2H) 8.50 (m, 2H); MS: m/z 281 [M-H].

Example 3

Step-3

2-(3-Fluoro-phenyl)-5-pyridin-4-yl-1H-pyrrole-3-carboxylic Acid Amide (A3)

$^1$H NMR (DMSO-$d_6$/400 MHz) δ ppm 7.16 (bs, 2H), 7.29 (m, 2H), 7.52 (m, 2H), 7.74 (s, 1H), 8.23 (d, J=5.80 Hz, 2H), 8.78 (d, J=5.80 Hz, 2H), 12.42 (s, 1H); ESI (+) MS: m/z 282 (MH$^+$).

Example 4

Step-1

2-(4-Fluoro-phenyl)-5-pyridin-4-yl-1H-pyrrole-3-carboxylic Acid Ethyl Ester

$^1$H NMR (DMSO-$d_6$/400 MHz) δ ppm 1.21 (t, J=7.08 Hz, 3H) 4.16 (q, J=7.08 Hz, 2H) 7.29-7.34 (m, 3H) 7.69 (m, 2H) 7.78 (dd, J=1.60, 4.63 Hz, 2H) 8.53 (dd, J=1.60, 4.63 Hz, 2H) 12.13 (s, 1H); ESI (+) MS: m/z 311 (MH$^+$).

Example 4

Step-2

2-(4-Fluoro-phenyl)-5-pyridin-4-yl-1H-pyrrole-3-carboxylic Acid

$^1$H NMR (DMSO-$d_6$/400 MHz) δ ppm 7.62-7.76 (m, 5H) 8.30 (bd, J=5.61 Hz, 2H) 8.75 (d, J=6.71 Hz, 2H) 12.58 (bs, 1H); MS: m/z 281 [M-H].

Example 4

Step-3

2-(4-Fluoro-phenyl)-5-pyridin-4-yl-1H-pyrrole-3-carboxylic Acid Amide Hydrochloride (A4)

$^1$H NMR (DMSO-$d_6$/400 MHz) δ ppm 7.12 (bs, 2H), 7.32-7.39 (m, 4H), 7.70 (d, J=2.43 Hz, 1H), 8.15 (d, J=6.59 Hz, 2H), 8.72 (d, J=6.59 Hz, 2H), 12.52 (s, 1H); ESI (+) MS: m/z 282 (MH$^+$).

Example 5

Step-1

2-(3-Bromo-phenyl)-5-pyridin-4-yl-1H-pyrrole-3-carboxylic Acid Ethyl Ester

$^1$H NMR (DMSO-$d_6$/400 MHz) δ ppm 1.22 (t, J=7.07 Hz, 3H) 4.17 (q, J=7.11 Hz, 2H) 7.31 (d, J=2.80 Hz, 1H) 7.44 (t, J=7.86 Hz, 1H) 7.62-7.69 (m, 2H) 7.80 (d, J=6.22 Hz, 2H) 7.86 (t, J=1.77 Hz, 1H) 8.55 (d, J=6.22 Hz, 2H) 12.20 (s, 1H); ESI (+) MS: m/z 316 (MH$^+$).

Example 5

Step-2

2-(3-Bromo-phenyl)-5-pyridin-4-yl-1H-pyrrole-3-carboxylic Acid

$^1$H NMR (DMSO-$d_6$/400 MHz) δ ppm 7.46 (t, J=7.93 Hz, 1H) 7.65-7.74 (m, 3H) 7.90 (s, 1H) 8.26 (d, J=5.73 Hz, 2H) 8.75 (d, J=6.46 Hz, 2H) 12.29 (bs, 1H) 12.54 (bs, 1H); MS: m/z 342 [M-H]. ESI (+) MS: m/z 343 (MH$^+$).

Example 5

Step-3

2-(3-Bromo-phenyl)-5-pyridin-4-yl-1H-pyrrole-3-carboxylic Acid Amide Hydrochloride (A5)

$^1$H NMR (DMSO-$d_6$/400 MHz) δ ppm 7.14 (bs, 1H) 7.44 (t, J=7.93 Hz, 1H) 7.51 (bs, 1H) 7.60-7.65 (m, J=9.02 Hz, 1H) 7.69 (d, J=2.56 Hz, 1H) 7.71-7.75 (m, 1H) 7.93 (t, J=1.83 Hz, 1H) 8.18 (d, J=5.85 Hz, 2H) 8.76 (d, J=6.83 Hz, 2H) 12.38 (bs, 1H); ESI (+) MS: m/z 342 (MH$^+$).

Example 6

Step-1

2-(4-Bromo-phenyl)-5-pyridin-4-yl-1H-pyrrole-3-carboxylic Acid Ethyl Ester

$^1$H NMR (DMSO-$d_6$/400 MHz) δ ppm 1.22 (t, J=7.07 Hz, 3H) 4.16 (q, J=7.07 Hz, 2H) 7.30 (d, J=2.80 Hz, 1H) 7.61 (d, J=8.54 Hz, 2H) 7.68 (d, J=8.54 Hz, 2H) 7.79 (d, J=6.22 Hz, 2H) 8.55 (d, J=5.98 Hz, 2H) 12.17 (bs, 1H); ESI (+) MS: m/z 316 (MH$^+$).

Example 6

Step-2

2-(4-Bromo-phenyl)-5-pyridin-4-yl-1H-pyrrole-3-carboxylic Acid $^1$H NMR (DMSO-d$_6$/400 MHz) δ ppm 7.62-7.76 (m, 5H) 8.30 (bd, J=5.61 Hz, 2H) 8.75 (d, J=6.71 Hz, 2H) 12.58 (bs, 1H); MS: m/z 342 [M-H].

Example 6

Step-3

2-(4-Bromo-phenyl)-5-pyridin-4-yl-1H-pyrrole-3-carboxylic Acid Amide Hydrochloride (A6)

$^1$H NMR (DMSO-d$_6$/400 MHz) δ ppm 6.93 (bs, 1H) 7.28 (d, J=2.68 Hz, 1H) 7.37 (bs, 1H) 7.62-7.67 (m, 4H) 7.69 (d, J=6.22 Hz, 2H) 8.54 (d, J=6.22 Hz, 2H) 11.86 (s, 1H); ESI (+) MS: m/z 342 (MH$^+$).

Example 7

Step-1

7-(3-Ethoxycarbonyl-5-pyridin-4-yl-1H-pyrrol-2-yl)-3,4-dihydro-1H-isoquinoline-2-carboxylic Acid tert-butyl Ester $^1$H NMR (400 MHz, DMSO-d$_6$) δ ppm 1.20 (t, J=7.07 Hz, 3H) 1.44 (s, 9H) 2.84 (t, J=5.85 Hz, 2H) 3.60 (t, J=5.91 Hz, 2H) 4.14 (q, J=7.07 Hz, 2H) 4.56 (bs, 2H) 7.24 (d, 1H) 7.27 (d, 1H) 7.41-7.47 (m, 2H) 7.76 (d, J=6.22 Hz, 2H) 8.52 (d, J=6.10 Hz, 2H) 12.02 (bs, 1H); ESI (+) MS: m/z 448 (MH$^+$).

Example 7

Step-2

7-(3-Carboxy-5-pyridin-4-yl-1H-pyrrol-2-yl)-3,4-dihydro-1H-isoquinoline-2-carboxylic Acid tert-butyl Ester MS: m/z 418 [M-H].

Example 7

Step-3

7-(3-Carbamoyl-5-pyridin-4-yl-1H-pyrrol-2-yl)-3,4-dihydro-1H-isoquinoline-2-carboxylic Acid tert-butyl Ester (A27)

$^1$H NMR (DMSO-d$_6$/400 MHz) δ ppm 1.44 (s, 9H) 2.82 (t, J=5.79 Hz, 2H) 3.59 (t, J=5.85 Hz, 2H) 4.54 (bs, 2H) 6.86 (bs, 2H) 7.20 (d, J=7.93 Hz, 1H) 7.24 (d, J=2.68 Hz, 1H) 7.44 (m, 1H) 7.47 (m, 1H) 7.67 (d, J=6.22 Hz, 2H) 8.51 (d, J=6.10 Hz, 2H) 11.72 (bs, 1H); ESI (+) MS: m/z 419 (MH$^+$).

By treatment with acids (for instance trifluoroacetic acid at room temperature for 24 h) the corresponding deprotected analog was obtained:

Example 8

5-Pyridin-4-yl-2-(1,2,3,4-tetrahydro-isoquinolin-7-yl)-1H-pyrrole-3-carboxylic Acid Amide (A28)

$^1$H NMR (DMSO-d$_6$/400 MHz) δ ppm 3.07 (t, J=6.10 Hz, 2H) 3.38-3.45 (m, 2H) 4.30 (t, J=4.33 Hz, 2H) 7.05 (bs, 1H) 7.30 (d, J=7.93 Hz, 1H) 7.42 (bs, 1H) 7.58 (d, J=8.50 Hz, 1H) 7.57 (s, 1H) 7.69 (d, J=2.32 Hz, 1H) 8.18 (d, J=6.22 Hz, 2H) 8.73 (d, J=6.83 Hz, 2H) 9.38 (bs, 2H) 12.41 (bs, 1H); ESI (+) MS: m/z 319 (MH$^+$).

Example 9

2-(2-Methyl-1,2,3,4-tetrahydro-isoquinolin-7-yl)-5-pyridin-4-yl-1H-pyrrole-3-carboxylic Acid Amide (A29)

By reductive amination, performed with formaldehyde and sodium cyanoborohydride, on the tetrahydro-isoquinoline nucleus of compound A28, the title compound A29 was obtained.

$^1$H NMR (DMSO-d$_6$/400 MHz) δ ppm 2.94 (s, 3H) 3.09 (d, J=16.90 Hz, 1H) 3.69 (d, J=7.44 Hz, 1H) 4.31 (dd, J=14.90, 6.60 Hz, 1H) 4.50 (d, J=14.88 Hz, 1H) 7.05 (bs, 1H) 7.33 (d, J=8.05 Hz, 1H) 7.44 (bs, 1H) 7.54 (d, J=1.10 Hz, 1H) 7.61 (dd, J=7.93, 1.71 Hz, 1H) 7.69 (d, J=2.56 Hz, 1H) 8.17 (d, J=6.71 Hz, 2H) 8.73 (d, J=6.83 Hz, 2H) 10.77 (bs, 1H) 12.42 (s, 1H); ESI (+) MS: m/z 333 (MH$^+$).

Example 10

Step-1

2,5-Di-pyridin-4-yl-1H-pyrrole-3-carboxylic Acid Ethyl Ester $^1$H NMR (400 MHz, DMSO-d$_6$) δ ppm 1.23 (t, J=7.07 Hz, 3H) 4.18 (q, J=7.07 Hz, 2H) 7.33 (d, J=2.8 Hz, 1H) 7.65 (dd, J=1.60, 4.51 Hz, 2H) 7.80 (dd, J=1.71, 4.63 Hz, 2H) 8.55 (dd, J=1.60, 4.51 Hz, 2H) 8.65 (dd, J=1.71, 4.61 Hz, 2H) 12.30 (bs, 1H); ESI (+) MS: m/z 294 (MH+).

Example 10

Step-2

2,5-Di-pyridin-4-yl-1H-pyrrole-3-carboxylic Acid $^1$H NMR (400 MHz, DMSO-d$_6$) δ ppm 7.02 (bs, 1H) 7.73 (m, 2H) 8.01 (m, 2H) 8.47 (m, 4H) 11.40 (bs, 1H); MS: m/z 264 [M-H].

Example 10

Step-3

2,5-Di-pyridin-4-yl-1H-pyrrole-3-carboxylic Acid Amide (C3)

$^1$H NMR (DMSO-d$_6$/400 MHz) δ ppm 7.02 (bs, 2H), 7.29 (s, 1H), 7.71 (m, 4H), 8.56 (m, 4H), 12.01 (bs, 1H); ESI (+) MS: m/z 265 (MH+).

Example 11

2-Cyclohexyl-5-pyridin-4-yl-1H-pyrrole-3-carboxylic Acid Amide (Q1)

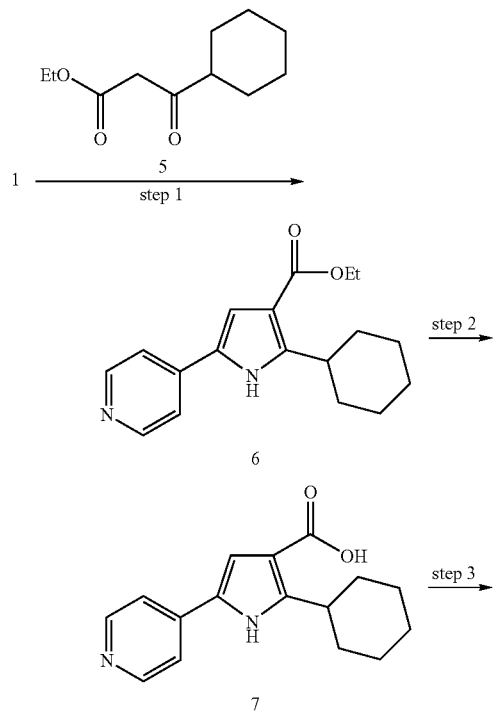

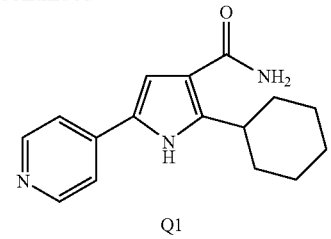

Step 1: Formation of Pyrrole Ring (6)

To a solution of 3-cyclohexyl-3-oxo-propionic acid ethyl ester 5 (1.6 g, 8.3 mmol) in anhydrous THF (200 mL), cooled at 0° C., NaH (900 mg, 21 mmol) was added. After 15 min 2-bromo-1-pyridin-4-yl-ethanone hydrobromide 1 (3 g, 10.8 mmol) was added and the mixture was stirred 5 h at 0° C. The solvent was removed and the residue was dissolved in EtOH (120 mL). Ammonium acetate (1.9 g, 25 mmol) was added and the solution was stirred overnight at rt. After solvent removal the residue was dissolved in EtOAc and the organic phase was washed with a saturated aqueous solution of Na$_2$CO$_3$, then with water, dried (Na$_2$SO$_4$) and concentrated. The crude material was purified by silica gel chromatography (eluant:EtOAc) to yield 2-cyclohexyl-5-pyridin-4-yl-1H-pyrrole-3-carboxylic acid ethyl ester as a white solid (1.1 g, 43%).

$^1$H NMR (DMSO-d$_6$/400 MHz) δ ppm 1.33 (m, 1H) 1.30 (t, J=7.13 Hz, 3H) 1.70-1.88 (m, 7H) 3.44-3.56 (m, 1H) 4.20 (q, J=7.15 Hz, 2H) 7.06 (d, J=2.68 Hz, 1H) 7.71 (d, J=6.22 Hz, 2H) 8.50 (d, J=6.22 Hz, 2H) 11.37 (bs, 1H); ESI (+) MS: m/z 299 (MH+).

Step 2: Saponification to Carboxylic Acid (7)

A solution of ester 6 (0.58 g, 1.95 mmol) in 4M aq NaOH and EtOH (1:1, 20 mL) was refluxed for 3 h, cooled in ice and acidified with 2N HCl. The precipitate was filtered, washed with little water and dried. 2-Cyclohexyl-5-pyridin-4-yl-1H-pyrrole-3-carboxylic acid hydrochloride was obtained as a white solid (0.55 g, 90%).

$^1$H NMR (DMSO-d$_6$/400 MHz) δ ppm 1.22-1.42 (m, 3H) 1.69-1.89 (m, 7H) 3.50-3.64 (m, 1H) 7.56 (d, J=2.56 Hz, 1H) 8.26 (d, J=6.71 Hz, 2H) 8.69 (d, J=6.71 Hz, 2H) 11.85 (s, 1H) 12.17 (bs, 1H); MS: m/z 269 [M-H].

Step 3: Condensation to Amide (Q1)

A solution of acid 7 (0.3 g, 1 mmol), HOBT-NH$_3$ (0.3 g, 2 mmol), TBTU (0.64 g, 2 mmol), DIEA (1 mL, 6 mmol) in DMF (4 mL) was stirred at rt for 6 h. The reaction mixture was poured into water and the aqueous phase was extracted (×3) with EtOAc. The organic phase was washed with 1N NaOH, then with water, brine, dried (Na$_2$SO$_4$) and concentrated. The crude material was purified by silica gel chromatography (DCM/MeOH 12:1) to yield 2-cyclohexyl-5-pyridin-4-yl-1H-pyrrole-3-carboxylic acid amide (0.12 g, 43%) as a white solid.

$^1$H NMR (DMSO-d$_6$/400 MHz) δ ppm 1.62-1.84 (m, 10H) 3.59-3.71 (m, 1H) 6.67 (bs, 1H) 7.13 (d, J=2.68 Hz, 1H) 7.21

(bs, 1H) 7.58 (d, J=6.22 Hz, 2H) 8.48 (d, J=6.10 Hz, 2H) 11.13 (bs, 1H); ESI (+) MS: m/z 270 (MH+).

Example 12

4-(3-Carbamoyl-5-pyridin-4-yl-1H-pyrrol-2-yl)-piperidine-1-carboxylic Acid tert-butyl Ester (Q3) and 2-piperidin-4-yl-5-pyridin-4-yl-1H-pyrrole-3-carboxylic Acid Amide (Q2)

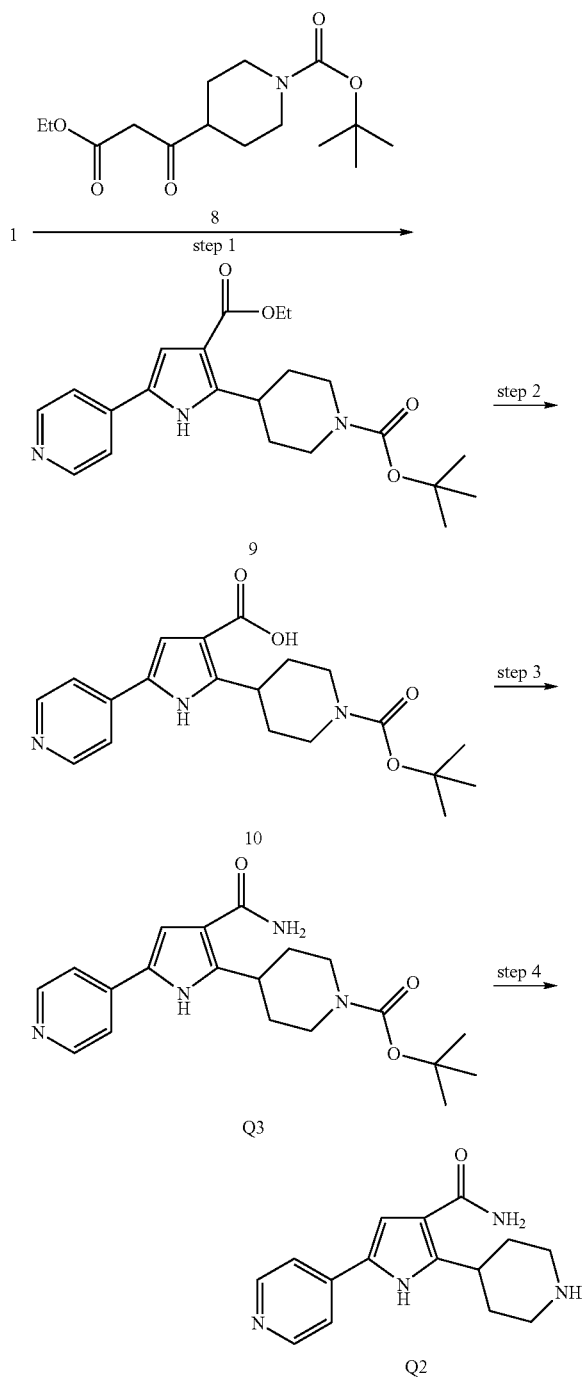

Step 1: Formation of Pyrrole Ring (9)

To a solution of 4-(2-ethoxycarbonyl-acetyl)-piperidine-1-carboxylic acid tert-butyl ester 8 (2.5 g, 8.3 mmol) in anhydrous THF (200 mL), cooled at 0° C., NaH (900 mg, 21 mmol) was added. After 15 min 2-bromo-1-pyridin-4-yl-ethanone hydrobromide 1 (3 g, 10.8 mmol) was added and the mixture was stirred 5 h at 0° C. The solvent was removed under reduced pressure and the residue was dissolved in EtOH (120 mL). Ammonium acetate (1.9 g, 25 mmol) was added and the solution was stirred overnight at rt. After solvent removal the residue was dissolved in EtOAc and the organic phase was washed with a saturated aq solution of $Na_2CO_3$, then with water, dried ($Na_2SO_4$) and concentrated. The crude material was purified by silica gel chromatography (eluant:EtOAc) to yield 4-(3-ethoxycarbonyl-5-pyridin-4-yl-1H-pyrrol-2-yl)-piperidine-1-carboxylic acid tert-butyl ester as a pink solid (1.55 g, 47%).

$^1$H NMR (DMSO-$d_6$/400 MHz) δ ppm 1.30 (t, J=7.07 Hz, 3H) 1.45 (s, 9H) 1.71 (bd, 2H) 1.80-1.92 (m, 2H) 2.79 (bs, 2H) 3.64-3.74 (m, 1H) 4.15 (bd, J=11.46 Hz, 2H) 4.21 (q, J=7.07 Hz, 2H) 7.08 (d, J=2.68 Hz, 1H) 7.71 (d, J=6.22 Hz, 2H) 8.50 (d, J=6.10 Hz, 2H) 11.45 (bs, 1H); ESI (+) MS: m/z 400 (MH+).

Step 2: Saponification to Carboxylic Acid (10)

A solution of ester 9 (0.8 g, 2 mmol) in 4M aq NaOH and EtOH (1:1, 20 mL) was refluxed for 2 h, cooled in ice and acidified with 2N HCl. The precipitate was filtered, washed with little water and dried. 4-(3-Carboxy-5-pyridin-4-yl-1H-pyrrol-2-yl)-piperidine-1-carboxylic acid tert-butyl ester hydrochloride was obtained as a white solid (0.54 g, 66%).

$^1$H NMR (DMSO-$d_6$/400 MHz) δ ppm 1.43 (s, 9H) 1.67-1.92 (m, 4H) 2.79 (bs, 2H) 3.68-3.79 (m, 1H) 4.13 (bd, J=11.58 Hz, 2H) 7.57 (d, J=2.56 Hz, 1H) 8.22 (d, J=6.83 Hz, 2H) 8.69 (d, J=6.83 Hz, 2H) 11.82 (bs, 1H); MS: m/z 370 [M-H].

Step 3: Condensation to Protected Amide (Q3)

A solution of acid 10 (0.53 g, 1.4 mmol), HOBT-$NH_3$ (0.43 g, 2.8 mmol), TBTU (0.9 g, 2.8 mmol), DIEA (1.4 mL) in DMF (4 mL) was stirred at rt for 15 h. The reaction mixture was poured into water and the aqueous phase was extracted (×3) with EtOAc. The organic phase was washed with 1N NaOH, then with water, brine, dried ($Na_2SO_4$) and concentrated. Upon solvent evaporation the crude material precipitated. It was filtered, washed with EtOAc, then with $Et_2O$. 4-(3-Carbamoyl-5-pyridin-4-yl-1H-pyrrol-2-yl)-piperidine-1-carboxylic acid tert-butyl ester was obtained as a white solid (0.25 g, 47%).

$^1$H NMR (DMSO-$d_6$/400 MHz) δ ppm 1.45 (s, 9H) 1.67 (bd, J=12.32 Hz, 2H) 1.76-1.89 (m, 2H) 2.71 (bs, 2H) 3.81-3.91 (m, 1H) 4.12 (bd, J=11.10 Hz, 2H) 6.76 (bs, 1H) 7.18 (d, J=2.56 Hz, 1H) 7.29 (bs, 1H) 7.59 (d, J=6.22 Hz, 2H) 8.50 (d, J=6.10 Hz, 2H) 11.22 (bs, 1H); ESI (+) MS: m/z 371 (MH+).

Step 4: Deprotection to Amide (Q2)

Amide Q3 (30 mg, 0.08 mmol) was dissolved in MeOH (5 mL), 2N HCl (1 mL) was added and the clear solution was warmed at 50° C. under stirring for 5 h. The precipitate was filtered and washed with MeOH. 2-Piperidin-4-yl-5-pyridin-4-yl-1H-pyrrole-3-carboxylic acid amide dihydrochloride was obtained as a white solid (25 mg, 90%).

$^1$H NMR (DMSO-d$_6$/400 MHz) δ ppm 1.96 (d, J=13.05 Hz, 2H) 2.09-2.24 (m, 2H) 2.92-3.07 (m, 2H) 3.74-3.87 (m, 1H) 7.01 (bs, 1H) 7.49 (bs, 1H) 7.66 (s, 1H) 8.10 (bs, 2H) 8.56 (bs, 1H) 8.71 (d, J=6.34 Hz, 2H) 8.83 (bs, 1H) 11.97 (bs, 1H); ESI (+) MS: m/z 271 (MH$^+$).

Example 13

5-(3-Fluoro-pyridin-4-yl)-2-phenyl-1H-pyrrole-3-carboxylic Acid Amide (E1)

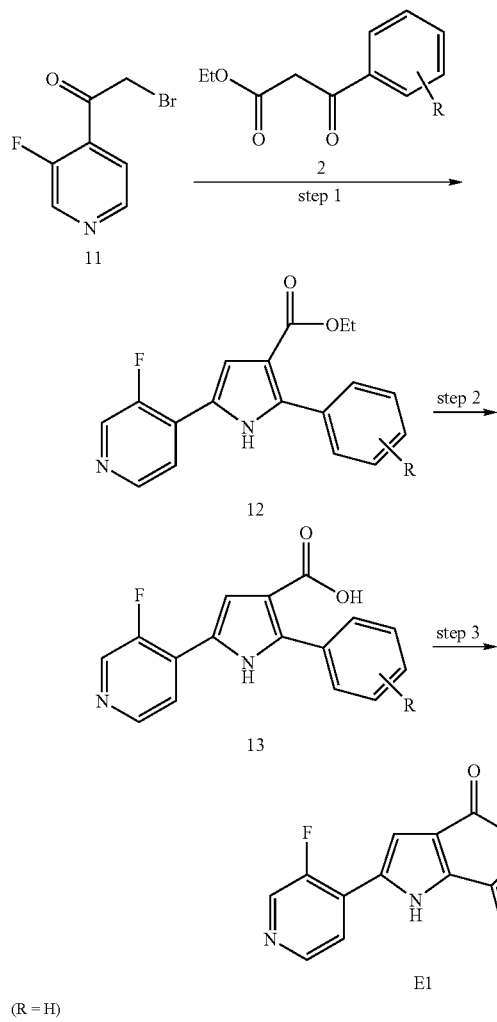

(R = H)

Step 1: Formation of Pyrrole Ring (12)

Bromoacetylfluoropyridine hydrobromide 11 (3.6 g, 12.0 mmol) was added to a mixture of 3-oxo-3-phenyl-propionic acid ethyl ester 2 (R═H, 2.0 g, 10.0 mmol) in 200 mL of anhydrous THF and NaH (0.5 g, 13.0 mmol) at 0° C. The solution was left at 0° C. for 1 h and then stirred to rt for 3 h. The solvent was removed and the residue was dissolved in 120 mL of EtOH, ammonium acetate (2.7 g, 36.0 mmol) was added, the reaction mixture was left overnight at rt and then warmed at 50° C. for 2 h. The crude material was purified by flash chromatography (DCM/MeOH 98:2) affording 1.88 g (60%) of 5-(3-fluoro-pyridin-4-yl)-2-phenyl-1H-pyrrole-3-carboxylic acid ethyl ester as a yellow solid.

$^1$H NMR (DMSO-d$_6$/400 MHz) δ ppm 1.25 (t, J=7.09 Hz, 3H), 4.23 (q, J=7.09 Hz, 2H), 7.30-7.60 (m, 7H), 8.40 (m, 1H), 8.53 (m, 1H), 11.80 (s, 1H); ESI (+) MS: m/z 311 (MH$^+$).

Step 2: Saponification to Carboxylic Acids (13)

Ester 12 (1.8 g, 5.8 mmol) in 10 mL of EtOH and 12 mL of 4M aq NaOH was heated at 100° C. for 4 h. The reaction mixture was cooled at 0° C. and acidified with conc HCl observing precipitation of the product which was filtered, washed with a little amount of water and acetone and dried, leading to 5-(3-fluoro-pyridin-4-yl)-2-phenyl-1H-pyrrole-3-carboxylic acid (1.7 g, 92%) as a solid that was used without further purification.

$^1$H NMR (DMSO-d$_6$/400 MHz) δ ppm 7.30-7.70 (m, 7H), 8.35 (m, 1H), 8.51 (m, 1H); MS: m/z 281 [M-H].

Step 3: Condensation to Amides (E1)

Acid 13 (1.0 g, 3.1 mmol) was dissolved in 40 mL of dry THF in the presence of DIEA (1.1 mL, 6.2 mmol). The solution was cooled at 0° C. and EDCI (0.9 g, 4.6 mmol) and HOBT.NH$_3$ (0.7 g, 4.6 mmol) were added. The reaction mixture was left overnight at rt. The solvent was removed, water was added and the mixture was extracted with DCM. The organic layer was dried (Na$_2$SO$_4$), the solvent was evaporated and the crude material was purified by flash chromatography (DCM/MeOH 95:5) to give 350 mg (40%) of 5-(3-fluoro-pyridin-4-yl)-2-phenyl-1H-pyrrole-3-carboxylic acid amide as a white solid.

$^1$H NMR (DMSO-d$_6$/400 MHz) δ ppm 6.86 (bs, 2H), 7.24 (t, J=3.05 Hz, 1H), 7.36-7.45 (m, 3H), 7.65 (m, 2H), 7.94 (m, 1H), 8.39 (d, J=5.12 Hz, 1H), 8.56 (d, J=3.41 Hz, 1H), 11.84 (s, 1H); ESI (+) MS: m/z 282 (MH$^+$).

Example 14

5-(2-Amino-pyrimidin-4-yl)-2-phenyl-1H-pyrrole-3-carboxylic Acid Amide (F1)

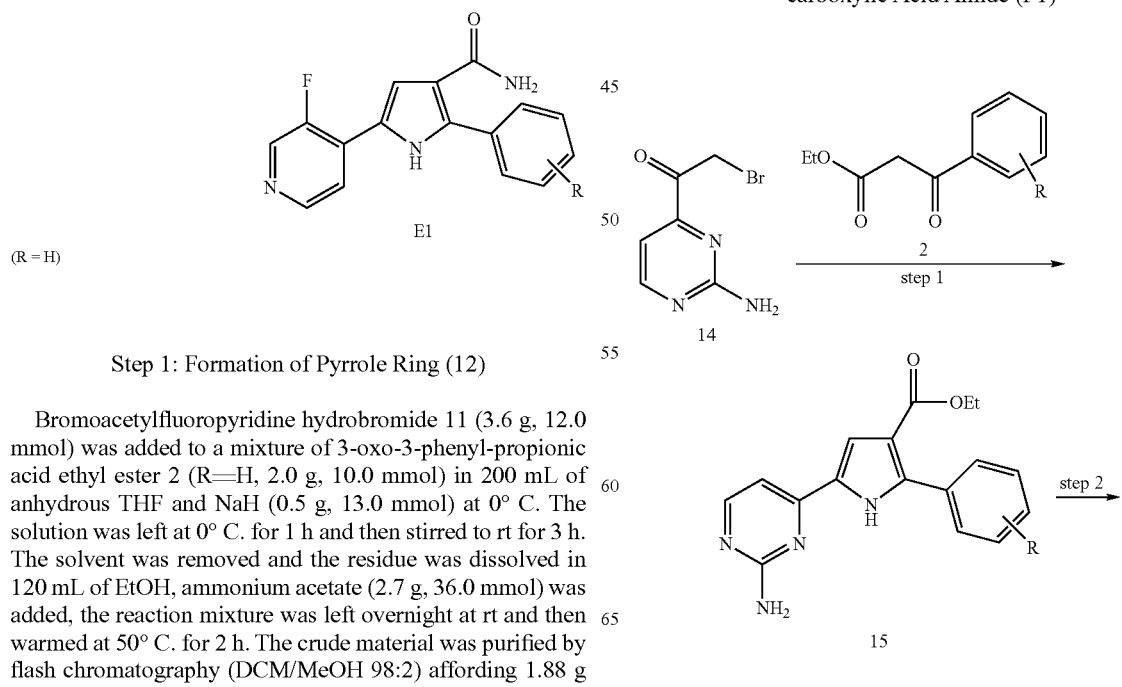

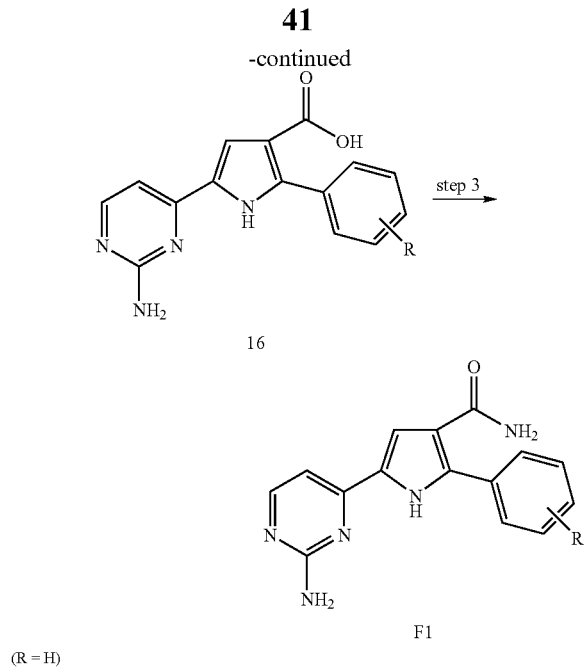

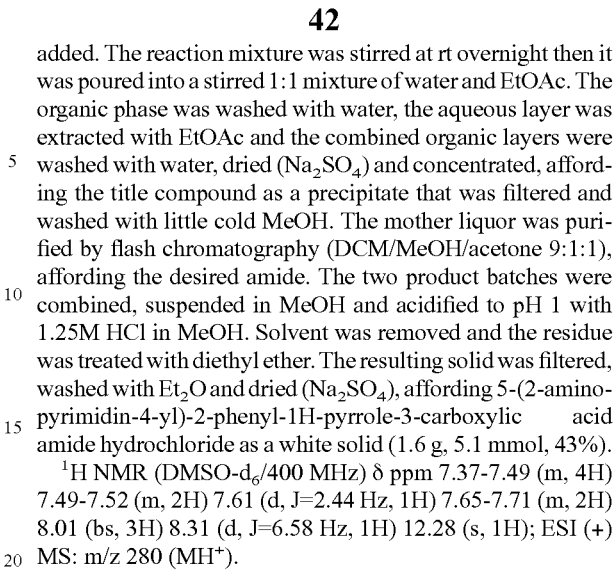

Step 1: Formation of Pyrrole Ring (15)

To a solution of ester 2 (R=H, 1.34 g, 7 mmol) in anhydrous THF (100 mL) at 0° C., NaH (0.7 g, 17.5 mmol) was added under argon with stirring. After 5 min bromoketone 14 (2.5 g, 8.4 mmol) was added and the mixture was stirred at rt for 3 h. Solvent was evaporated, the residue was dissolved in EtOH (65 mL), ammonium acetate (1.6 g, 21 mmol) was added and the solution was stirred at rt overnight. Solvent was evaporated to dryness and the residue was purified by flash chromatography (EtOAc/n-hexane 7:3). Obtained 5-(2-amino-pyrimidin-4-yl)-2-phenyl-1H-pyrrole-3-carboxylic acid ethyl ester (0.99 g, 3.2 mmol, 46%).

$^1$H NMR (DMSO-$d_6$/400 MHz) δ ppm 1.20 (t, J=7.13 Hz, 3H) 4.14 (q, J=7.07 Hz, 2H) 6.45 (s, 2H) 7.10 (d, J=5.24 Hz, 1H) 7.33 (d, J=2.56 Hz, 1H) 7.40-7.49 (m, 3H) 7.61-7.65 (m, 2H) 8.23 (d, J=5.24 Hz, 1H) 12.01 (bs, 1H); ESI (+) MS: m/z 309 (MH$^+$).

Step 2: Saponification to Carboxylic Acids (16)

To a suspension of ester 15 (3.65 g, 11.85 mmol) in 95% EtOH (45 mL), 4M aq NaOH (45 mL) was added and the mixture was refluxed for 5 h. Most solvent was evaporated and the residue, cooled in ice bath, was acidified to pH 5 with conc HCl, observing precipitation of the product. The precipitate was filtered, washed with little cold water, and dried. 5-(2-Amino-pyrimidin-4-yl)-2-phenyl-1H-pyrrole-3-carboxylic acid, obtained as a white solid (3.5 g), was used in the next step without further purifications.

$^1$H NMR (DMSO-$d_6$/400 MHz) δ ppm 7.35-7.69 (m, 6H) 7.76 (bs, 2H) 8.31 (d, J=5.73 Hz, 1H) 12.37 (bs, 1H); MS: m/z 279 [M-H].

Step 3: Condensation to Amides (F1)

To a suspension of acid 16 (4 g, 14.3 mmol) in anhydrous THF (80 mL), DIEA (5.5 g, 42.9 mmol) and anhydrous DMF (8 mL), cooled in ice bath and under stirring, HOBT-NH$_3$ (3.26 g, 21.4 mmol) and EDCI (4.1 g, 21.4 mmol) were added. The reaction mixture was stirred at rt overnight then it was poured into a stirred 1:1 mixture of water and EtOAc. The organic phase was washed with water, the aqueous layer was extracted with EtOAc and the combined organic layers were washed with water, dried (Na$_2$SO$_4$) and concentrated, affording the title compound as a precipitate that was filtered and washed with little cold MeOH. The mother liquor was purified by flash chromatography (DCM/MeOH/acetone 9:1:1), affording the desired amide. The two product batches were combined, suspended in MeOH and acidified to pH 1 with 1.25M HCl in MeOH. Solvent was removed and the residue was treated with diethyl ether. The resulting solid was filtered, washed with Et$_2$O and dried (Na$_2$SO$_4$), affording 5-(2-amino-pyrimidin-4-yl)-2-phenyl-1H-pyrrole-3-carboxylic acid amide hydrochloride as a white solid (1.6 g, 5.1 mmol, 43%).

$^1$H NMR (DMSO-$d_6$/400 MHz) δ ppm 7.37-7.49 (m, 4H) 7.49-7.52 (m, 2H) 7.61 (d, J=2.44 Hz, 1H) 7.65-7.71 (m, 2H) 8.01 (bs, 3H) 8.31 (d, J=6.58 Hz, 1H) 12.28 (s, 1H); ESI (+) MS: m/z 280 (MH$^+$).

The above procedure was employed to synthesize the following compounds:

Example 15

Step-1

5-(2-Amino-pyrimidin-4-yl)-2-o-tolyl-1H-pyrrole-3-carboxylic Acid Ethyl Ester $^1$H NMR (400 MHz, DMSO-$d_6$) δ ppm 1.07 (t, J=7.07 Hz, 3H) 2.14 (s, 3H) 4.02 (q, J=7.07 Hz, 2H) 6.54 (bs, 2H) 7.04 (d, J=5.37 Hz, 1H) 7.22-7.37 (m, 5H) 8.20 (d, J=5.37 Hz, 1H) 12.12 (bs, 1H); ESI (+) MS: m/z 323 (MH$^+$).

Example 15

Step-2

5-(2-Amino-pyrimidin-4-yl)-2-o-tolyl-1H-pyrrole-3-carboxylic Acid $^1$H NMR (400 MHz, DMSO-$d_6$) δ ppm 6.34 (bs, 2H) 6.98 (d, J=5.24 Hz, 1H) 7.18-7.33 (m, 5H) 8.15 (d, J=5.24 Hz, 1H) 11.75 (bs, 1H); MS: m/z 293 [M-H].

Example 15

Step-3

5-(2-Amino-pyrimidin-4-yl)-2-o-tolyl-1H-pyrrole-3-carboxylic Acid Amide (F2)

$^1$H NMR (DMSO-$d_6$/400 MHz) δ ppm 2.16 (s, 3H), 6.87 (bs, 2H), 7.21-7.34 (m, 5H), 7.62 (s, 1H), 7.74 (bs, 2H), 8.25 (d, J=6.47 Hz, 1H), 12.20 (bs, 1H); ESI (+) MS: m/z 294 (MH$^+$).

Example 16

Step-1

5-(2-Amino-pyrimidin-4-yl)-2-(2-fluoro-phenyl)-1H-pyrrole-3-carboxylic Acid Ethyl Ester $^1$H NMR (400 MHz, DMSO-$d_6$) δ ppm 1.11 (t, J=7.07 Hz, 3H) 4.06 (q, J=7.07 Hz, 2H) 6.43 (bs, 2H) 7.03 (d, J=5.24 Hz, 1H) 7.28 (m, 3H) 7.50 (m, 2H) 8.21 (d, J=5.24 Hz, 1H) 12.23 (bs, 1H); ESI (+) MS: m/z 327 (MH⁺).

Example 16

Step-2

5-(2-Amino-pyrimidin-4-yl)-2-(2-fluoro-phenyl)-1H-pyrrole-3-carboxylic Acid $^1$H NMR (400 MHz, DMSO-$d_6$) δ ppm 6.36 (bs, 2H) 6.97 (d, J=5.24 Hz, 1H) 7.23 (m, 3H) 7.39 (m, 1H) 7.58 (m, 1H) 8.17 (d, J=5.24 Hz, 1H) 11.69 (bs, 1H); MS: m/z 297 [M-H].

Example 16

Step-3

5-(2-Amino-pyrimidin-4-yl)-2-(2-fluoro-phenyl)-1H-pyrrole-3-carboxylic Acid Amide (F4)

$^1$H NMR (DMSO-$d_6$/400 MHz) δ ppm 6.92 (bs, 2H), 7.27 (m, 3H), 7.45-7.54 (m, 2H), 7.62 (bs, 1H), 7.84 (bs, 2H), 8.28 (d, J=6.58 Hz, 1H), 12.41 (bs, 1H); ESI (+) MS: m/z 298 (MH⁺).

Example 17

Step-1

5-(2-Amino-pyrimidin-4-yl)-2-(2,3-dimethyl-phenyl)-1H-pyrrole-3-carboxylic Acid Ethyl Ester $^1$H NMR (400 MHz, DMSO-$d_6$) δ ppm 1.06 (t, J=7.07 Hz, 3H) 2.02 (s, 3H) 2.29 (s, 3H) 4.01 (q, J=7.07 Hz, 2H) 6.40 (bs, 2H) 7.01 (d, J=5.24 Hz, 1H) 7.07-7.16 (m, 2H) 7.23 (d, J=6.83 Hz, 1H) 7.29 (d, J=2.68 Hz, 1H) 8.18 (d, J=5.24 Hz, 1H) 12.03 (bs, 1H); ESI (+) MS: m/z 337 (MH⁺).

Example 17

Step-2

5-(2-Amino-pyrimidin-4-yl)-2-(2,3-dimethyl-phenyl)-1H-pyrrole-3-carboxylic Acid $^1$H NMR (400 MHz, DMSO-$d_6$) δ ppm 2.04 (s, 3H) 2.30 (s, 3H) 6.37 (bs, 2H) 7.00 (d, J=5.24 Hz, 1H) 7.08-7.17 (m, 2H) 7.23 (d, J=6.71 Hz, 1H) 7.27 (d, J=2.68 Hz, 1H) 8.18 (d, J=5.24 Hz, 1H) 11.64 (bs, 1H) 11.89 (bs, 1H); MS: m/z 307 [M-H].

Example 17

Step-3

5-(2-Amino-pyrimidin-4-yl)-2-(2,3-dimethyl-phenyl)-1H-pyrrole-3-carboxylic Acid Amide (F15)

$^1$H NMR (DMSO-$d_6$/400 MHz) δ ppm 2.03 (s, 3H), 2.29 (s, 3H), 6.31 (bs, 2H), 6.69 (bs, 2H), 6.94 (d, J=5.24 Hz, 1H), 7.08-7.17 (m, 2H), 7.23 (d, J=6.95 Hz, 1H), 7.31 (d, J=2.68 Hz, 1H), 8.16 (d, J=5.24 Hz, 1H), 10.70 (bs, 1H); ESI (+) MS: m/z 308 (MH⁺).

Example 18

Step-1

5-(2-Amino-pyrimidin-4-yl)-2-(2-chloro-4-fluoro-phenyl)-1H-pyrrole-3-carboxylic Acid Ethyl Ester $^1$H NMR (400 MHz, DMSO-$d_6$) δ ppm 1.07 (t, J=7.07 Hz, 3H) 4.03 (q, J=7.07 Hz, 2H) 6.41 (bs, 2H) 7.00 (d, J=5.24 Hz, 1H) 7.25-7.34 (m, 2H) 7.48-7.59 (m, 2H) 8.21 (d, J=5.24 Hz, 1H) 12.27 (bs, 1H); ESI (+) MS: m/z 361 (MH⁺).

Example 18

Step-2

5-(2-Amino-pyrimidin-4-yl)-2-(2-chloro-4-fluoro-phenyl)-1H-pyrrole-3-carboxylic Acid $^1$H NMR (400 MHz, DMSO-$d_6$) δ ppm 6.38 (bs, 2H) 6.99 (d, J=5.24 Hz, 1H) 7.22-7.30 (m, 2H) 7.50-7.57 (m, 2H) 8.20 (d, J=5.24 Hz, 1H) 11.49 (bs, 1H) 12.10 (bs, 1H); MS: m/z 331 [M-H].

Example 18

Step-3

5-(2-Amino-pyrimidin-4-yl)-2-(2-chloro-4-fluoro-phenyl)-1H-pyrrole-3-carboxylic Acid Amide (F23)

$^1$H NMR (DMSO-$d_6$/400 MHz) δ ppm 6.38 (bs, 2H), 6.72 (bs, 1H), 6.92 (d, J=5.24 Hz, 1H), 7.22-7.33 (m, 2H), 7.35 (d, J=2.56 Hz, 1H), 7.45-7.54 (m, 2H), 8.22 (d, J=5.24 Hz, 1H), 11.95 (bs, 1H); ESI (+) MS: m/z 332 (MH⁺).

Example 19

Step-1

5-(2-Amino-pyrimidin-4-yl)-2-(2,4-dichloro-phenyl)-1H-pyrrole-3-carboxylic Acid Ethyl Ester $^1$H NMR (DMSO-$d_6$/400 MHz) δ ppm 1.08 (t, J=7.07 Hz, 3H) 4.04 (q, J=7.07 Hz, 2H) 6.42 (bs, 2H) 7.01 (d, J=5.24 Hz, 1H) 7.29 (d, J=2.19 Hz, 1H) 7.49 (m, 2H) 7.73 (t, J=1.22 Hz, 1H) 8.22 (d, J=5.24 Hz, 1H) 12.30 (bs, 1H); ESI (+) MS: m/z 377 (MH⁺).

Example 19

Step-2

5-(2-Amino-pyrimidin-4-yl)-2-(2,4-dichloro-phenyl)-1H-pyrrole-3-carboxylic Acid

MS: m/z 347 [M-H].

Example 19

Step-3

5-(2-Amino-pyrimidin-4-yl)-2-(2,4-dichloro-phenyl)-1H-pyrrole-3-carboxylic Acid Amide (F26)

$^1$H NMR (DMSO-$d_6$/400 MHz) δ ppm 6.81 (bs, 1H) 6.95 (bs, 2H) 7.01 (d, J=5.73 Hz, 1H) 7.37 (bs, 1H) 7.46 (d, J=2.68 Hz, 1H) 7.68 (dd, J=1.77, 0.55 Hz, 1H) 8.23 (d, J=5.73 Hz, 1H) 12.17 (bs, 1H); ESI (+) MS: m/z 348 (MH$^+$).

Example 20

Step-1

5-(2-Amino-pyrimidin-4-yl)-2-(2-fluoro-4-methyl-phenyl)-1H-pyrrole-3-carboxylic Acid Ethyl Ester $^1$H NMR (DMSO-$d_6$/400 MHz) δ ppm 1.13 (t, J=7.07 Hz, 3H) 2.38 (s, 3H) 4.07 (q, J=7.07 Hz, 2H) 6.43 (bs, 2H) 7.03 (d, J=5.24 Hz, 1H) 7.06-7.15 (m, 2H) 7.29 (d, J=2.44 Hz, 1H) 7.38 (t, J=8.17 Hz, 1H) 8.22 (d, J=5.24 Hz, 1H) 12.15 (bs, 1H); ESI (+) MS: m/z 341 (MH$^+$).

Example 20

Step-2

5-(2-Amino-pyrimidin-4-yl)-2-(2-fluoro-4-methyl-phenyl)-1H-pyrrole-3-carboxylic Acid $^1$H NMR (DMSO-$d_6$/400 MHz) δ ppm 2.58 (s, 3H) 6.39 (bs, 2H) 7.00 (d, J=5.24 Hz, 1H) 7.04-7.13 (m, 2H) 7.26 (d, J=2.44 Hz, 1H) 7.37 (t, J=8.17 Hz, 1H) 8.21 (d, J=5.24 Hz, 1H) 11.78 (bs, 1H) 12.03 (bs, 1H); MS: m/z 311 [M-H].

Example 20

Step-3

5-(2-Amino-pyrimidin-4-yl)-2-(2-fluoro-4-methyl-phenyl)-1H-pyrrole-3-carboxylic Acid Amide (F28)

$^1$H NMR (DMSO-$d_6$/400 MHz) δ ppm 2.37 (s, 3H), 6.37 (bs, 2H), 6.73 (bs, 1H), 6.95 (d, J=5.24 Hz, 1H), 7.02-7.09 (m, 2H), 7.26 (bs, 1H), 7.30 (d, J=2.56 Hz, 1H), 7.37 (t, J=7.90 Hz, 1H), 8.20 (d, J=5.24 Hz, 1H), 11.78 (bs, 1H); ESI (+) MS: m/z 312 (MH$^+$).

Example 21

Step-1

5-(2-Amino-pyrimidin-4-yl)-2-(2-chloro-5-fluoro-phenyl)-1H-pyrrole-3-carboxylic Acid Ethyl Ester $^1$H NMR (DMSO-$d_6$/400 MHz) δ ppm 1.07 (t, J=7.07 Hz, 3H) 4.05 (q, J=7.07 Hz, 2H) 6.42 (bs, 2H) 7.01 (d, J=5.24 Hz, 1H) 7.30 (d, J=2.44 Hz, 1H) 7.32-7.39 (m, 1H) 7.41 (dd, J=8.90, 3.05 Hz, 1H) 8.60 (dd, J=8.90, 5.24 Hz, 1H) 8.23 (d, J=5.24 Hz, 1H) 12.32 (bs, 1H); ESI (+) MS: m/z 361 (MH$^+$).

Example 21

Step-2

5-(2-Amino-pyrimidin-4-yl)-2-(2-chloro-5-fluoro-phenyl)-1H-pyrrole-3-carboxylic Acid $^1$H NMR (DMSO-$d_6$/400 MHz) δ ppm 6.40 (bs, 2H) 7.00 (d, J=5.24 Hz, 1H) 7.26 (d, J=2.32 Hz, 1H) 7.30-7.37 (m, 1H) 7.40 (dd, J=8.90, 3.05 Hz, 1H) 8.59 (dd, J=8.90, 5.24 Hz, 1H) 8.22 (d, J=5.24 Hz, 1H) 11.85 (bs, 1H) 12.20 (bs, 1H); MS: m/z 331 [M-H].

Example 21

Step-3

5-(2-Amino-pyrimidin-4-yl)-2-(2-chloro-5-fluoro-phenyl)-1H-pyrrole-3-carboxylic Acid Amide (F31)

$^1$H NMR (DMSO-$d_6$/400 MHz) δ ppm 6.35 (bs, 2H), 6.75 (bs, 1H), 6.92 (d, J=5.24 Hz, 1H), 7.26-7.34 (m, 3H), 7.35 (d, J=2.56 Hz, 1H), 7.55 (dd, J=8.72, 5.30 Hz, 1H), 8.22 (d, J=5.24 Hz, 1H), 11.98 (bs, 1H); ESI (+) MS: m/z 332 (MH$^+$).

Example 22

Step-1

5-(2-Amino-pyrimidin-4-yl)-2-(4-chloro-2-fluoro-phenyl)-1H-pyrrole-3-carboxylic Acid Ethyl Ester $^1$H NMR (DMSO-$d_6$/400 MHz) δ ppm 4.10 (q, J=7.07 Hz, 2H) 6.48 (bs, 2H) 7.04 (d, J=5.24 Hz, 1H) 7.32 (bs, 1H) 7.38 (m, 1H) 7.54 (m, 2H) 8.24 (d, J=5.24 Hz, 1H) 12.32 (bs, 1H); ESI (+) MS: m/z 361 (MH$^+$).

Example 22

Step-2

5-(2-Amino-pyrimidin-4-yl)-2-(4-chloro-2-fluoro-phenyl)-1H-pyrrole-3-carboxylic Acid $^1$H NMR (DMSO-$d_6$/400 MHz) δ ppm 6.32 (bs, 2H) 6.93 (d, J=5.24 Hz, 1H) 7.14 (s, 1H) 7.25 (m, 2H) 7.65 (t, J=8.17 Hz, 1H) 8.15 (d, J=5.25 Hz, 1H) 12.20 (bs, 1H); MS: m/z 331 [M-H].

Example 22

Step-3

5-(2-Amino-pyrimidin-4-yl)-2-(4-chloro-2-fluoro-phenyl)-1H-pyrrole-3-carboxylic Acid Amide (F36)

$^1$H NMR (DMSO-$d_6$/400 MHz) δ ppm 6.37 (bs, 2H), 6.80 (bs, 1H), 6.93 (d, J=5.24 Hz, 1H), 7.31-7.37 (m, 2H), 7.41 (bs, 1H), 7.46 (dd, J=9.76, 1.95 Hz, 1H), 7.49-7.56 (m, 1H), 8.23 (d, J=5.24, 1H), 11.95 (bs, 1H); ESI (+) MS: m/z 332 (MH⁺).

Example 23

Step-1

5-(2-Amino-pyrimidin-4-yl)-2-(2,6-difluoro-phenyl)-1H-pyrrole-3-carboxylic Acid Ethyl Ester ¹H NMR (DMSO-d₆/400 MHz) δ ppm 1.09 (t, J=7.07 Hz, 3H) 4.06 (q, J=7.07 Hz, 2H) 6.46 (bs, 2H) 7.01 (d, J=5.24 Hz, 1H) 7.14-7.26 (m, 2H) 7.34 (d, J=2.32 Hz, 1H) 7.49-7.60 (m, 1H) 8.24 (d, J=5.24 Hz, 1H) 12.44 (bs, 1H); ESI (+) MS: m/z 345 (MH⁺).

Example 23

Step-2

5-(2-Amino-pyrimidin-4-yl)-2-(2,6-difluoro-phenyl)-1H-pyrrole-3-carboxylic Acid

¹H NMR (DMSO-d₆/400 MHz) δ ppm 6.42 (bs, 2H) 6.99 (d, J=5.24 Hz, 1H) 7.12-7.23 (m, 2H) 7.30 (d, J=1.95 Hz, 1H) 7.48-7.56 (m, 1H) 8.22 (d, J=5.24 Hz, 1H) 11.92 (bs, 1H) 12.32 (bs, 1H); MS: m/z 315 [M-H].

Example 23

Step-3

5-(2-Amino-pyrimidin-4-yl)-2-(2,6-difluoro-phenyl)-1-pyrrole-3-carboxylic Acid Amide (F37)

¹H NMR (DMSO-d₆/400 MHz) δ ppm 6.40 (bs, 2H), 6.75 (bs, 1H), 6.89 (d, J=5.24 Hz, 1H), 7.09-7.16 (m, 2H), 7.38 (d, J=2.44 Hz, 1H), 7.41 (bs, 1H), 7.43-7.52 (m, 1H), 8.22 (d, J=5.24 Hz, 1H), 12.10 (bs, 1H); ESI (+) MS: m/z 316 (MH⁺).

Example 24

Step-1

5-(2-Amino-pyrimidin-4-yl)-2-thiophen-2-yl-1H-pyrrole-3-carboxylic Acid Ethyl Ester ¹H NMR (DMSO-d₆/400 MHz) δ ppm 1.26 (t, J=7.07 Hz, 3H) 4.19 (q, J=7.07 Hz, 2H) 6.47 (bs, 2H) 7.11 (d, J=5.12 Hz, 1H) 7.15 (dd, J=5.06, 3.72 Hz, 1H) 7.30 (d, J=2.07 Hz, 1H) 7.64 (dd, J=3.66, 1.22 Hz, 1H) 7.67 (dd, J=5.06, 1.16 Hz, 1H) 8.23 (d, J=5.24 Hz, 1H) 11.92 (bs, 1H); ESI (+) MS: m/z 315 (MH⁺).

Example 24

Step-2

5-(2-Amino-pyrimidin-4-yl)-2-thiophen-2-yl-1H-pyrrole-3-carboxylic Acid

MS: m/z 285 [M-H].

Example 24

Step-3

5-(2-Amino-pyrimidin-4-yl)-2-thiophen-2-yl-1H-pyrrole-3-carboxylic Acid Amide (G2)

¹H NMR (DMSO-d₆/400 MHz) δ ppm 6.46 (bs, 2H) 6.91 (bs, 1H) 7.04 (d, J=5.37 Hz, 1H) 7.11 (dd, J=5.12, 3.66 Hz, 1H) 7.30 (d, J=1.95 Hz, 1H) 7.44 (bs, 1H) 7.57 (dd, J=5.12, 1.22 Hz, 1H) 7.66 (dd, J=3.66, 1.22 Hz, 1H) 8.23 (d, J=5.24 Hz, 1H) 11.60 (bs, 1H); ESI (+) MS: m/z 286 (MH⁺).

Example 25

Step-1

5-(2-Amino-pyrimidin-4-yl)-2-(5-methyl-thiophen-2-yl)-1H-pyrrole-3-carboxylic Acid Ethyl Ester ¹H NMR (DMSO-d₆/400 MHz) δ ppm 1.26 (t, J=7.07 Hz, 3H) 2.50 (s, 3H) 4.19 (q, J=7.07 Hz, 2H) 6.46 (bs, 2H) 6.84 (dd, J=3.54, 0.98 Hz, 1H) 7.10 (d, J=5.24 Hz, 1H) 7.27 (d, J=2.07 Hz, 1H) 7.45 (d, J=3.54 Hz, 1H) 8.22 (d, J=5.12 Hz, 1H) 11.92 (bs, 1H); ESI (+) MS: m/z 329 (MH⁺).

Example 25

Step-2

5-(2-Amino-pyrimidin-4-yl)-2-(5-methyl-thiophen-2-yl)-1H-pyrrole-3-carboxylic Acid MS: m/z 299 [M-H].

Example 25

Step-3

5-(2-Amino-pyrimidin-4-yl)-2-(5-methyl-thiophen-2-yl)-1H-pyrrole-3-carboxylic Acid Amide (G3)

¹H NMR (DMSO-d₆/400 MHz) δ ppm 2.46 (d, J=0.73 Hz, 3H) 6.40 (bs, 2H) 6.79 (dd, J=3.54, 1.10 Hz, 1H) 6.85 (bs, 1H) 7.01 (d, J=5.24 Hz, 1H) 7.25 (d, J=2.07 Hz, 1H) 7.38 (bs, 1H) 7.44 (d, J=3.29 Hz, 1H) 8.21 (d, J=5.24 Hz, 1H) 11.45 (bs, 1H); ESI (+) MS: m/z 300 (MH⁺).

Example 26

Step-1

5-[5-(2-Amino-pyrimidin-4-yl)-3-ethoxycarbonyl-1H-pyrrol-2-yl]-3,4-dihydro-1H-isoquinoline-2-carboxylic Acid tert-butyl Ester ¹H NMR (DMSO-d₆/400 MHz) δ ppm 1.08 (t, J=7.01 Hz, 3H) 1.44 (s, 9H) 2.51-2.59 (m, 2H) 3.42-3.53 (m, 2H) 4.03 (q, J=7.03 Hz, 2H) 4.58 (bs, 2H) 6.45 (bs, 2H) 7.03 (d, J=5.24 Hz, 1H) 7.16-7.35 (m, 4H) 8.21 (d, J=5.00 Hz, 1H) 12.11 (bs, 1H); ESI (+) MS: m/z 464 (MH$^+$).

Example 26

Step-2

5-[5-(2-Amino-pyrimidin-4-yl)-3-carboxy-1H-pyrrol-2-yl]-3,4-dihydro-1H-isoquinoline-2-carboxylic Acid tert-butyl Ester MS: m/z 434 [M-H].

Example 26

Step-3

5-[5-(2-Amino-pyrimidin-4-yl)-3-carbamoyl-1H-pyrrol-2-yl]-3,4-dihydro-1H-isoquinoline-2-carboxylic Acid tert-butyl Ester (G7)

$^1$H NMR (DMSO-d$_6$/400 MHz) δ ppm 1.44 (s, 9H) 2.58 (t, J=5.79 Hz, 2H) 3.48 (t, J=6.10 Hz, 2H) 4.58 (bs, 2H) 6.89 (bs, 1H) 7.11-7.39 (m, 5H) 7.64 (d, J=2.19 Hz, 1H) 7.75 (bs, 2H) 8.27 (d, J=6.34 Hz, 1H) 12.28 (bs, 1H); ESI (+) MS: m/z 435 (MH$^+$).

Example 27

5-(2-Amino-pyrimidin-4-yl)-2-(1,2,3,4-tetrahydro-isoquinolin-5-yl)-1H-pyrrole-3-carboxylic Acid Amide (G8)

By treatment of compound G7 prepared in Example 26 with acids, for instance trifluoroacetic acid at room temperature for 24 h, the corresponding deprotected analog G8 was obtained.

$^1$H NMR (DMSO-d$_6$/400 MHz) δ ppm 2.78 (t, J=5.91 Hz, 2H) 4.35 (t, J=4.51 Hz, 2H) 6.90 (bs, 1H) 7.25 (d, J=6.58 Hz, 1H) 7.27-7.30 (m, 1H) 7.31-7.39 (m, 3H) 7.70 (d, J=2.44 Hz, 1H) 7.86 (bs, 3H) 8.30 (d, J=6.46 Hz, 1H) 9.32 (bs, 2H) 12.44 (bs, 1H); ESI (+) MS: m/z 335 (MH$^+$).

Example 28

Step-1

5-(2-Amino-pyrimidin-4-yl)-2-pyridin-2-yl-1H-pyrrole-3-carboxylic Acid Ethyl Ester $^1$H NMR (DMSO-d$_6$/400 MHz) δ ppm 1.29 (t, 3H, J=7.1 Hz) 4.25 (q, 2H, J=7.07 Hz) 6.64 (bs, 2H) 7.16 (d, 1H, J=5.12 Hz) 7.4 (m, 2H) 7.9 (td, 1H, J=7.8, 1.83 Hz) 8.2 (d, 1H, J=5.12 Hz) 8.4 (dt, 1H, J=8.05, 0.98 Hz) 8.7 (ddd, 1H, J=4.82, 1.77, 0.98 Hz) 11.5 (bs, 1H); ESI (+) MS: m/z 310 (MH$^+$).

Example 28

Step-2

5-(2-Amino-pyrimidin-4-yl)-2-pyridin-2-yl-1H-pyrrole-3-carboxylic Acid $^1$H NMR (DMSO-d$_6$/400 MHz) δ ppm 6.46 (bs, 2H) 7.08 (d, 1H, J=5.12 Hz) 7.31 (m, 2H) 7.91 (t, 1H, J=7.87 Hz) 8.17 (d, 1H, J=5.12 Hz) 8.55 (d, 1H, J=3.90 Hz) 8.80 (bs, 1H); MS: m/z 280 [M-H].

Example 28

Step-3

5-(2-Amino-pyrimidin-4-yl)-2-pyridin-2-yl-1H-pyrrole-3-carboxylic Acid Amide (G12)

$^1$H NMR (DMSO-d$_6$/400 MHz) δ ppm 6.62 (bs, 2H), 7.03 (d, J=5.12 Hz, 1H), 7.16 (bs, 1H), 7.33-7.40 (m, 2H) 7.86-7.93 (m, 1H), 8.25 (d, J=5.12 Hz, 1H), 8.28 (bs, 1H), 8.43 (d, J=8.17 Hz, 1H), 8.62-8.67 (m, 1H), 11.29 (s, 1H); ESI (+) MS: m/z 281 (MH$^+$).

Example 29

Step-1

5-(2-Amino-pyrimidin-4-yl)-2-(1-methyl-1H-indol-3-yl)-1H-pyrrole-3-carboxylic Acid Ethyl Ester $^1$H NMR (DMSO-d$_6$/400 MHz) δ ppm 1.12 (t, J=7.07 Hz, 3H) 3.87 (s, 3H) 4.08 (q, J=7.07 Hz, 2H) 6.41 (bs, 2H) 7.05 (d, J=5.24 Hz, 1H) 7.08-7.14 (m, 1H) 7.19-7.25 (m, 1H) 7.33 (d, J=2.68 Hz, 1H) 7.47-7.53 (m, 2H) 7.77 (s, 1H) 8.18 (d, J=5.24 Hz, 1H) 11.65 (bs, 1H); ESI (+) MS: m/z 362 (MH$^+$).

Example 29

Step-2

5-(2-Amino-pyrimidin-4-yl)-2-(1-methyl-1H-indol-3-yl)-1H-pyrrole-3-carboxylic Acid $^1$H NMR (DMSO-d$_6$/400 MHz) δ ppm 3.87 (s, 3H) 6.40 (bs, 2H) 7.03 (d, J=5.24 Hz, 1H) 7.11 (t, J=7.80 Hz, 1H) 7.22 (t, J=7.80 Hz, 1H) 7.32 (d, J=2.56 Hz, 1H) 7.49-7.54 (m, 2H) 7.77 (s, 1H) 8.18 (d, J=5.24 Hz, 1H) 11.50 (bs, 1H); MS: m/z 332 [M-H].

Example 29

Step-3

5-(2-Amino-pyrimidin-4-yl)-2-(1-methyl-1H-indol-3-yl)-1H-pyrrole-3-carboxylic Acid Amide (G13)

$^1$H NMR (DMSO-d$_6$/400 MHz) δ ppm 3.87 (s, 3H), 6.35 (bs, 2H), 6.73 (bs, 1H), 6.91 (bs, 1H), 6.98 (d, J=5.24 Hz, 1H), 7.11 (t, J=7.07 Hz, 1H), 7.22 (t, J=7.07 Hz, 1H), 7.32 (d, J=2.68 Hz, 1H), 7.48-7.53 (m, 2H), 7.80 (s, 1H), 8.17 (d, J=5.24 Hz, 1H), 11.36 (bs, 1H); ESI (+) MS: m/z 333 (MH$^+$).

Example 30

Step-1

5-(2-Amino-pyrimidin-4-yl)-2-(1-methyl-1H-indol-2-yl)-1H-pyrrole-3-carboxylic Acid Ethyl Ester $^1$H NMR (DMSO-d$_6$/400 MHz) δ ppm 1.10 (t, J=7.07 Hz, 3H), 3.59 (s, 3H), 4.09 (q, J=7.07 Hz, 2H), 6.47 (bs, 2H), 6.66 (d, J=0.73 Hz, 1H), 7.10 (d, J=5.24 Hz, 1H), 7.10-7.12 (m, 1H), 7.19-7.27 (m, 1H), 7.38 (d, J=2.68 Hz, 1H), 7.51 (d, J=7.32 Hz, 1H), 7.62 (d, J=7.80 Hz, 1H) 8.24 (d, J=5.24 Hz, 1H) 12.33 (bs, 1H); ESI (+) MS: m/z 362 (MH$^+$).

Example 30

Step-2

5-(2-Amino-pyrimidin-4-yl)-2-(1-methyl-1H-indol-2-yl)-1H-pyrrole-3-carboxylic Acid MS: m/z 332 [M-H].

Example 30

Step-3

5-(2-Amino-pyrimidin-4-yl)-2-(1-methyl-1H-indol-2-yl)-1H-pyrrole-3-carboxylic Acid Amide (G14)

$^1$H NMR (DMSO-$d_6$/400 MHz) δ ppm 3.58 (s, 3H), 6.38 (bs, 2H), 6.61 (d, J=0.61 Hz, 1H), 6.88 (bs, 1H), 7.00 (d, J=5.24 Hz, 1H), 7.08 (t, J=7.70 Hz, 1H), 7.20 (t, J=7.70 Hz, 1H), 7.25 (bs, 1H), 7.41 (d, J=2.44 Hz, 1H), 7.47 (d, J=7.70 Hz, 1H), 7.59 (d, J=7.70 Hz, 1H), 8.22 (d, J=5.24 Hz, 1H), 11.98 (bs, 1H); ESI (+) MS: m/z 333 (MH$^+$).

Example 31

Step-1

5-(2-Amino-pyrimidin-4-yl)-2-benzo[b]thiophen-5-yl-1H-pyrrole-3-carboxylic Acid Ethyl Ester $^1$H NMR (DMSO-$d_6$/400 MHz) δ ppm 1.18 (t, J=7.07 Hz, 3H) 4.13 (q, J=7.07 Hz, 2H) 6.45 (s, 2H) 7.10 (d, J=5.24 Hz, 1H) 7.35 (d, J=2.56 Hz, 1H) 7.53 (d, J=5.12 Hz, 1H) 7.60 (dd, J=8.41, 1.59 Hz, 1H) 7.82 (d, J=5.49 Hz, 1H) 8.06 (d, J=8.41 Hz, 1H) 8.13 (d, J=1.34 Hz, 1H) 8.22 (d, J=5.24 Hz, 1H) 12.06 (bs, 1H); ESI (+) MS: m/z 365 (MH$^+$).

Example 31

Step-2

5-(2-Amino-pyrimidin-4-yl)-2-benzo[b]thiophen-5-yl-1H-pyrrole-3-carboxylic Acid

MS: m/z 335 [M-H].

Example 31

Step-3

5-(2-Amino-pyrimidin-4-yl)-2-benzo[b]thiophen-5-yl-1H-pyrrole-3-carboxylic Acid Amide (G15)

$^1$H NMR (DMSO-$d_6$/400 MHz) δ ppm 6.43 (bs, 2H) 6.84 (bs, 1H) 7.04 (d, J=5.37 Hz, 1H) 7.31 (d, J=2.44 Hz, 1H) 7.34 (bs, 1H) 7.50 (dd, J=5.49, 0.49 Hz, 1H) 7.62 (dd, J=8.41, 1.71 Hz, 1H) 7.80 (d, J=5.49 Hz, 1H) 8.01 (d, J=8.41 Hz, 1H) 8.13 (d, J=1.34 Hz, 1H) 8.21 (d, J=5.37 Hz, 1H) 11.75 (bs, 1H); ESI (+) MS: m/z 336 (MH$^+$).

Example 32

5-(2-Amino-5-fluoro-pyrimidin-4-yl)-2-phenyl-1H-pyrrole-3-carboxylic Acid Amide (V1)

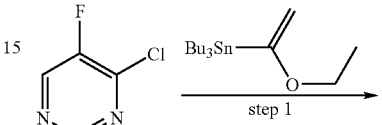

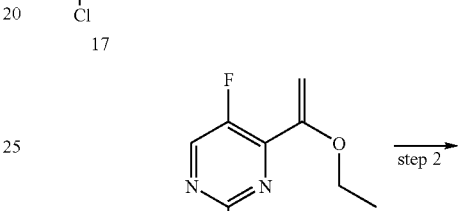

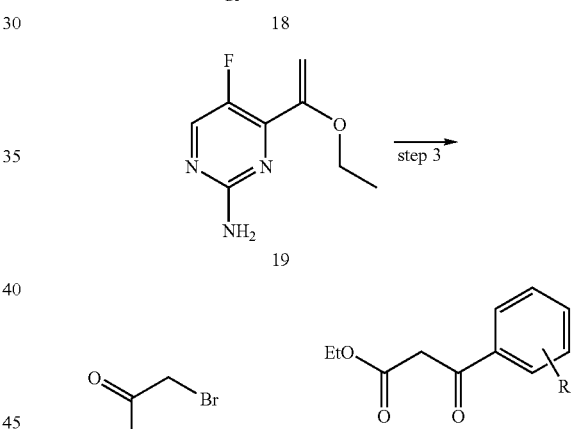

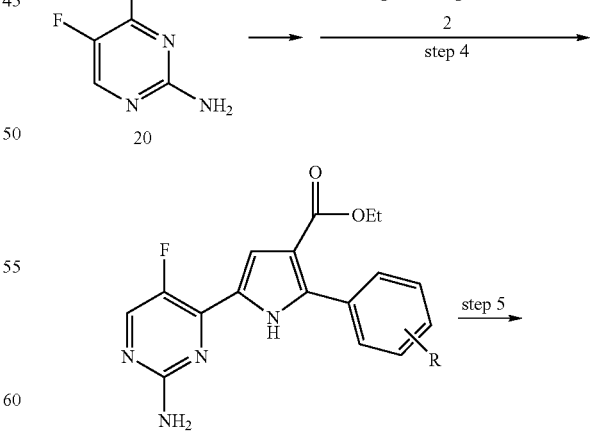

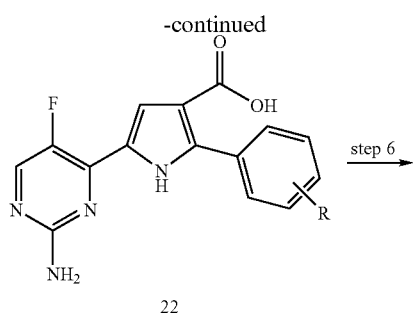

22

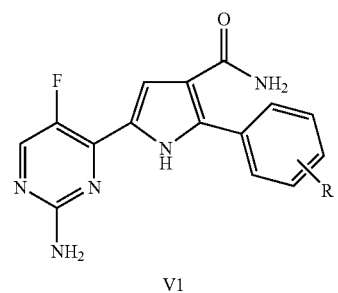

V1
(R = H)

Step 1: Alkylation of Pyrimidine Ring (18)

To a solution of 2,4-dichloro-5-fluoro-pyrimidine 17 (1.2 g, 7.24 mmol) in DMF (14 mL), tributyl-(1-ethoxy-vinyl)-stannane (2.7 mL, 7.9 mmol) was added, followed by dichlorobis(triphenylphosphine) palladium(II) (100 mg, 0.145 mmol). The mixture was warmed at 70° C. for 1 hour, cooled, a saturated solution of potassium fluoride (aq) was added and the mixture was stirred at room temperature for 18 hours. After dilution with water/diethylether and filtration through celite the organic phases were washed thoroughly with water and concentrated. The crude material was purified with the Horizon system (25 mm column), eluting with n-hexane/EtOAc 95:5. Obtained 2-chloro-4-(1-ethoxy-vinyl)-5-fluoro-pyrimidine (1.24 g, 84%).

$^1$H NMR (400 MHz, DMSO-$d_6$) δ ppm 1.32 (t, J=6.95 Hz, 3H) 3.95 (q, J=6.99 Hz, 2H) 4.88 (d, J=2.80 Hz, 1H) 5.20 (d, J=2.93 Hz, 1H) 8.90 (d, J=3.17 Hz, 1H); ESI (+) MS: m/z 203 (MH$^+$).

Step 2: Amination of Pyrimidine Ring (19)

A solution of enolether 18 (15.5 g, 76.73 mmol) in absolute ethanol (25 mL) and 30% aqueous ammonia (50 mL) was warmed under shaking at 100° C. for 1.5 hours in a Parr apparatus. After cooling, ethanol was removed and the compound was extracted with dichloromethane. The crude material was purified with the Horizon system, eluting with n-hexane/EtOAc 1:1. Obtained 4-(1-ethoxy-vinyl)-5-fluoro-pyrimidin-2-ylamine (9 g, 49.2 mmol, 64%).

$^1$H NMR (400 MHz, DMSO-$d_6$) δ ppm 1.29 (t, J=7.01 Hz, 3H) 3.87 (q, J=6.95 Hz, 2H) 4.62 (d, J=2.44 Hz, 1H) 4.91 (dd, J=2.38, 0.55 Hz, 1H) 6.64 (bs, 2H) 8.28 (d, J=3.54 Hz, 1H); ESI (+) MS: m/z 184 (MH$^+$).

Step 3: Bromination to Bromoketone (20)

To a solution of enolether 19 (510 mg, 2.78 mmol) in THF (25 mL), water (1.7 mL) was added followed by NBS (515 mg, 2.78 mmol). The mixture was stirred at room temperature for 1.5 hours. Solvent was evaporated, the residue was stirred thoroughly in methanol and filtered. Obtained 1-(2-amino-5-fluoro-pyrimidin-4-yl)-2-bromo-ethanone (500 mg, 77%).

$^1$H NMR (400 MHz, DMSO-$d_6$) δ ppm 4.70 (s, 2H) 6.94 (bs, 2H) 8.50 (d, J=2.93 Hz, 1H); ESI (+) MS: m/z 235 (MH$^+$).

Step 4: Formation of Pyrrole Ring (21)

To a solution of ketoester 2 (192 mg, 1 mmol) in THF (5 mL), cooled at 0° C., sodium hydride (80 mg, 2 mmol) was added under stirring. After 5 minutes a solution of bromoketone 20 (234 mg, 1 mmol) in DMF (2 mL) was added and the reaction mixture was stirred at 50° C. for 8 hours. After removal of THF, ethanol (10 mL) and ammonium acetate (240 mg, 3 mmol) were added and the mixture was stirred at room temperature for 20 hours. After removal of the solvent, ethylacetate was added, the organic phase was washed with water and the crude material was purified through an Horizon system, eluting with n-hexane/EtOAc 1:1. Obtained 5-(2-amino-5-fluoro-pyrimidin-4-yl)-2-phenyl-1H-pyrrole-3-carboxylic acid ethyl ester (50 mg, 16%). ESI (+) MS: m/z 327 (MH$^+$).

Step 5: Hydrolysis to Acids (22)

To a suspension of ester 21 (25 mg, 0.077 mmol) in 95% EtOH (0.5 mL), 4M aq NaOH (0.5 mL) was added and the mixture was refluxed for 2 h. The mixture was acidified to pH 5 with conc HCl, observing precipitation of the product. The precipitate was filtered, washed with little cold water and dried. 5-(2-Amino-5-fluoro-pyrimidin-4-yl)-2-phenyl-1H-pyrrole-3-carboxylic acid, obtained as a white solid (16 mg, 64%), was used in the next step without further purifications.

ESI (+) MS: m/z 299 (MH$^+$).

Step 6: Condensation to Amides (V1)

To a solution of acid 22 (16 mg, 0.054 mmol) in DMF (0.5 mL) and DIEA (0.03 mL) stirred at 0° C., HOBT.NH$_3$ (13 mg, 0.08 mmol) and EDCI (16 mg, 0.08 mmol) were added. The mixture was stirred at room temperature for 20 hours. After dilution with ethyl acetate the organic phase was washed with water, with sat. aq. solution of sodium bicarbonate, dried over Na$_2$SO$_4$ and concentrated. The crude material was purified by flash chromatography (eluant:AcOEt/n-hexane 9:1). Obtained the title compound in 74% yield.

¹H NMR (DMSO-d₆/400 MHz) δ ppm 6.34 (s, 2H) 6.87 (bs, 1H) 7.27 (t, J=2.80 Hz, 1H) 7.33-7.43 (m, 3H) 7.40 (s, 1H) 7.62-7.66 (m, 2H) 8.27 (d, J=3.41 Hz, 1H) 11.49 (bs, 1H). ESI (+) MS: m/z 298 (MH⁺).

Example 33

2-Phenyl-5-(2-phenylamino-pyrimidin-4-yl)-1H-pyrrole-3-carboxylic Acid Amide (H1)

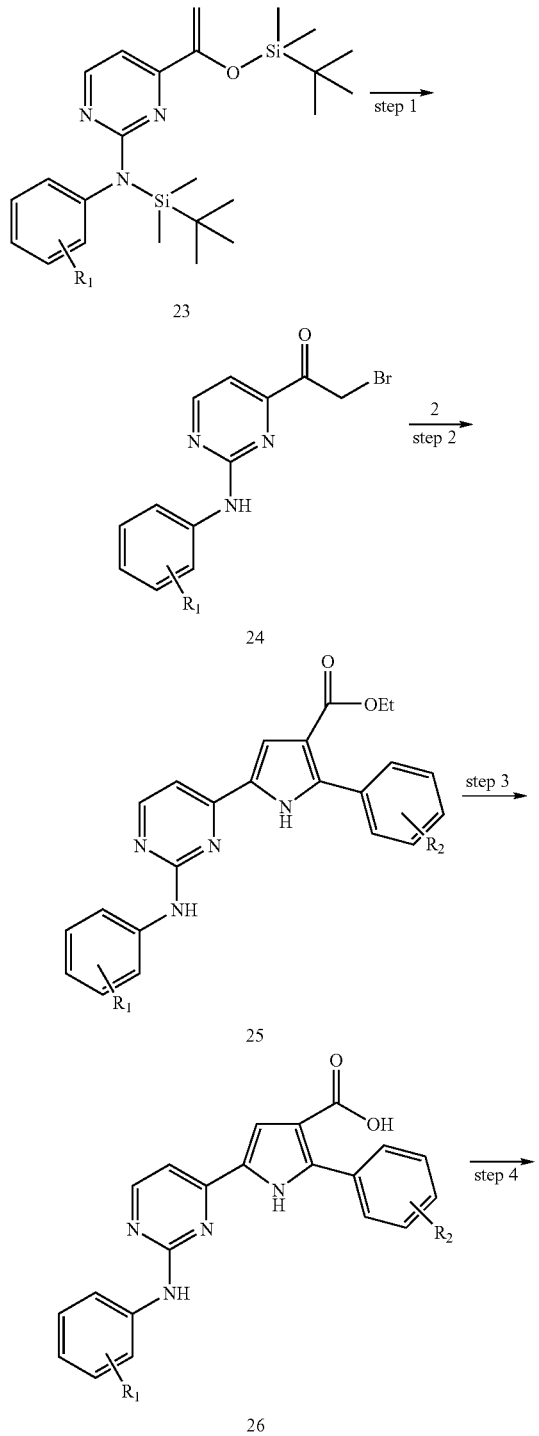

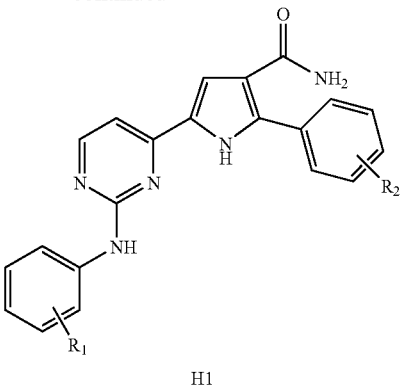

(R1, R2 = H)

Step 1: Bromination to Bromoketone (24)

To a solution of enolsilylether 23 (1 g, 2.27 mmol) in THF (40 mL) and water (5 mL) at room temperature, solid NBS (0.43 g, 62.4 mmol) was added and the mixture was stirred for 20 hours. After solvent evaporation and aqueous work-up with ethyl acetate, the crude material was purified by flash chromatography (eluant:n-hexane/EtOAc 4:1), yielding 2-bromo-1-(2-phenylamino-pyrimidin-4-yl)-ethanone as a yellow solid (0.27 g, 40%).

¹H NMR (DMSO-d₆/300 MHz) δ ppm 4.65 (s, 2H), 6.7 (m, 1H), 6.9 (d, 1H), 7.0 (m, 2H), 7.4 (d, 2H), 8.4 (d, 1H), 9.6 (s, 1H); ESI (+) MS: m/z 293 (MH⁺).

Step 2: Pyrrole Ring Formation (25)

To a solution of ester 2 (150 μL, 0.87 mmol) in anhydrous THF (40 mL) at 0° C., NaH (50 mg, 1.2 mmol) was added under argon with stirring. After 40 min bromoketone 24 (260 mg, 0.89 mmol, prepared as described in WO2005014572) was added and the mixture was stirred at rt for 3 h. Solvent was evaporated to dryness, the residue was dissolved in EtOH (10 mL), ammonium acetate (343 g, 4.45 mmol) was added and the solution was stirred at rt overnight. Solvent was evaporated to dryness and EtOAc and water were added to the crude material and the organic layer was separated, washed with water, dried (Na₂SO₄) and concentrated. The residue was taken up with Et₂O/EtOAc/n-hexane (1:1:1) and filtered. Obtained 2-phenyl-5-(2-phenylamino-pyrimidin-4-yl)-1H-pyrrole-3-carboxylic acid ethyl ester (120 mg, 36%).

¹H NMR (DMSO-d₆/400 MHz) δ ppm 1.20 (t, 3H) 4.14 (q, 2H) 6.90-7.85 (m, 11H) 7.35 (d, J=5.27 Hz, 1H) 8.46 (d, J=5.27 Hz, 1H) 9.45 (s, 1H) 12.10 (s, 1H); ESI (+) MS: m/z 385 (MH⁺).

Step 3: Saponification to Carboxylic Acids (26)

To a suspension of ester 25 (120 mg, 0.31 mmol) in 95% EtOH (3 mL), 4M aq NaOH (4 mL) was added and the mixture was refluxed for 4 h. Most solvent was evaporated and the residue, cooled in ice bath, was acidified to pH 5 with conc. AcOH, observing precipitation of the product. The precipitate was filtered, washed with little cold water, and dried. 2-Phenyl-5-(2-phenylamino-pyrimidin-4-yl)-1H-pyrrole-3-carboxylic acid, obtained as a white solid (100 mg), was used in the next step without further purifications. MS: m/z 355 [M-H].

Step 3: Condensation to Amides (H1)

To a suspension of acid 26 (90 mg, 0.25 mmol) in DMF (3 mL), DIEA (120 μL, 0.67 mmol), EDCI (100 mg, 0.52 mmol) and HOBT.NH₃ (79 mg, 0.52 mmol) were added. The reaction mixture was stirred at rt overnight then it was poured into a stirred 1:1 mixture of water and EtOAc. The organic phase was washed with water, the aqueous layer was extracted with EtOAc and the combined organic layers were washed with water, dried (Na₂SO₄) and concentrated, affording a crude material that was purified by flash chromatography (DCM/MeOH 96:4), affording 2-phenyl-5-(2-phenylamino-pyrimidin-4-yl)-1H-pyrrole-3-carboxylic acid amide as a white solid (35 mg, 30% two steps).

¹H NMR (300 MHz, DMSO-d₆) δ ppm 6.90 (s, 1H) 6.95 (t, J=7.33 Hz, 1H) 7.25-7.50 (m, 7H) 7.29 (d, J=5.57 Hz, 1H) 7.60 (d, 2H) 7.85 (d, J=7.62 Hz, 2H) 8.43 (d, J=5.27 Hz, 1H) 9.40 (s, 1H) 11.75 (s, 1H); ESI (+) MS: m/z 356 (MH⁺).

Example 34

5-(2-Amino-pyrimidin-4-yl)-1-ethyl-2-phenyl-1H-pyrrole-3-carboxylic Acid Amide (L1)

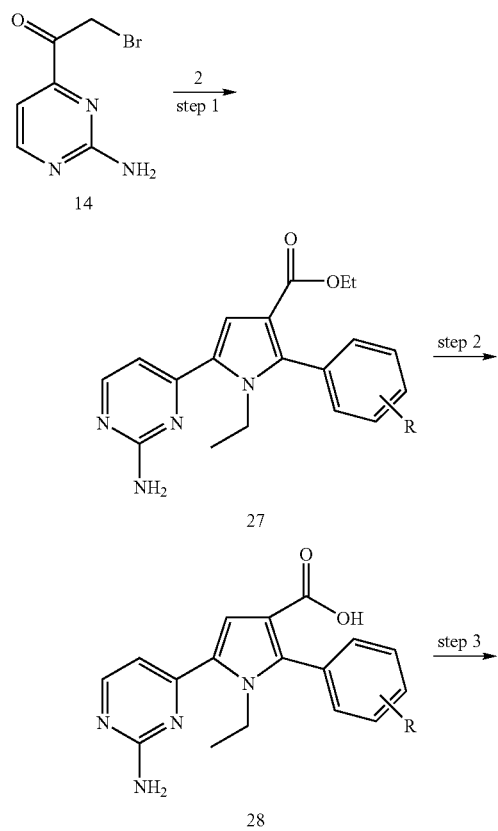

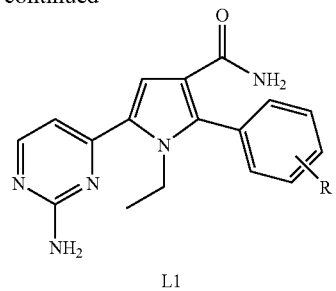

(R = H)

Step 1: Formation of pyrrole ring (27)

To a solution of ester 2 (1.34 g, 7 mmol) in anhydrous THF (100 mL) at 0° C., NaH (0.7 g, 17.5 mmol) was added under argon with stirring. After 5 min bromoketone 14 (2.5 g, 8.4 mmol) was added and the mixture was stirred at rt for 3 h. Solvent was evaporated, the residue was dissolved in AcOH (30 mL) and 2M EtNH₂ in THF (8.7 mL, 17.5 mmol). The mixture was treated with microwaves at 170° C. for 5 min then it was diluted with EtOAc and washed with NaHCO₃ aq saturated solution. The aqueous layer was extracted with EtOAc and the combined organic layers were washed with water, dried (Na₂SO₄) and concentrated. The residue was purified by flash chromatography (DCM/EtOH/acetone 96:2:2), thus affording 0.7 g of 5-(2-amino-pyrimidin-4-yl)-1-ethyl-2-phenyl-1H-pyrrole-3-carboxylic acid ethyl ester (29% yield). ESI (+) MS: m/z 337 (MH⁺).

Step 2: Saponification to Carboxylic Acids (28)

To a suspension of ester 27 (0.7 g, 2.08 mmol) in 95% EtOH (8 ml), 4M aq NaOH (8 mL) was added and the mixture was stirred for 1 h at 100° C. The solvent was removed under vacuum and the aqueous residue was acidified with conc HCl to pH 5, observing precipitation of the product. The mixture was filtered, the solid was washed with little cold water and dried thus affording 0.66 g of 5-(2-amino-pyrimidin-4-yl)-1-ethyl-2-phenyl-1H-pyrrole-3-carboxylic acid that was used in the next step without further purification. MS: m/z 307 [M-H].

Step 3: Condensation to Amides (L1)

To a suspension of acid 28 (400 mg, 1.31 mmol) in 10 mL of THF and 600 μL of DIEA (3.52 mmol), cooled in ice bath, 336 mg of EDCI (1.75 mmol) and 267 mg of HOBT-NH₃ (1.75 mmol) were added and the mixture was stirred overnight at rt. EtOAc and water were added, the layers were separated, the aqueous layer was extracted with EtOAc and the combined organic layers were washed with 1M aq NaOH and water. They were then dried (Na₂SO₄) and concentrated. The residue was filtered and washed with little cold MeOH. The mother liquor was purified by flash chromatography (DCM/MeOH/acetone 90:5:5), affording the desired amide. The two product batches were combined, suspended in MeOH and acidified to pH 1 with 1.25M HCl in MeOH. The solvent was removed and the residue was treated with Et₂O: the resulting solid was filtered, washed with Et₂O and concentrated, affording 380 mg of the hydrochloric salt of 5-(2-amino-pyrimidin-4-yl)-1-ethyl-2-phenyl-1H-pyrrole-3-carboxylic acid amide (1.1 mmol, 83% yield).

¹H NMR (DMSO-d₆/400 MHz) δ ppm 1.08 (t, J=6.89 Hz, 3H) 4.37 (q, J=6.91 Hz, 2H) 6.87 (bd, J=21.95 Hz, 2H) 7.18 (d, J=6.58 Hz, 1H) 7.38-7.43 (m, 2H) 7.50-7.55 (m, 3H) 7.81 (s, 1H) 8.00 (bs, 3H) 8.23 (d, J=6.71 Hz, 1H); ESI (+) MS: m/z 308 (MH⁺).

Example 35

2-Bromo-5-pyridin-4-yl-1H-pyrrole-3-carboxylic Acid Amide (R1) and 2-(3-methoxy-phenyl)-5-pyridin-4-yl-1H-pyrrole-3-carboxylic Acid Amide (A11)

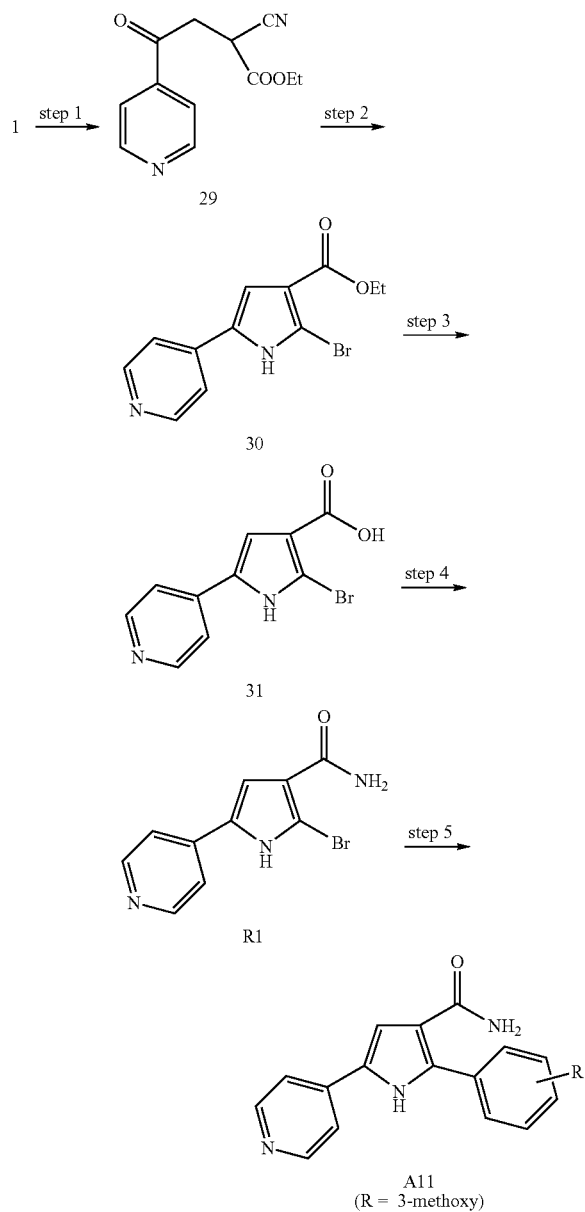

Step 1: Condensation to Cyanoester (29)

To a suspension of sodium metal (81 mg, 3.5 mmol) in 10 mL anhydrous EtOH, ethylcyanoacetate (0.37 mL, 3.5 mmol) was added at 0° C. The solution was stirred until sodium was completely dissolved. The solvent was evaporated to obtain a white solid that was added portionwise to a stirred solution of bromoacetylpyridine 1 (1.0 g, 3.5 mmol) in anhydrous THF (20 mL) and DIEA (0.6 mL, 3.5 mmol). The reaction mixture was stirred overnight at rt. The solvent was removed, the residue was suspended in water and extracted with DCM. The organic extracts were dried over Na₂SO₄ and concentrated. The crude was purified by flash chromatography (DCM/MeOH 95:5) to give 710 mg (87%) of 2-cyano-4-oxo-4-pyridin-4-yl-butyric acid ethyl ester as a reddish oil.
¹H NMR (DMSO-d₆/400 MHz) δ ppm 1.23 (t, J=7.07 Hz, 3H), 3.88 (d, J=5.25 Hz, 2H), 4.21 (q, J=7.07 Hz, 2H), 4.64 (t, J=5.25 Hz, 1H), 7.89 (d, J=6.00 Hz, 2H), 8.85 (d, J=6.00 Hz, 2H); ESI (+) MS: m/z 233 (MH⁺).

Step 2: Formation of Pyrrole Ring (30)

To a solution of HBr (33% in AcOH, 13 mL, 43.1 mmol) at 0° C. a solution of cyanoester 29 (1.0 g, 4.3 mmol), dissolved in Et₂O and DCM, was added dropwise. The reaction mixture was left for 20 min at 0° C. and then at rt until disappearance of the starting material (2.5 h). The solid was filtered and washed with acetone and MeOH. The pyridinium salt was neutralized with 7N NH₃ in MeOH. The solid was purified by flash chromatography (DCM/MeOH 95:5) to give 800 mg (62%) of 2-bromo-5-pyridin-4-yl-1H-pyrrole-3-carboxylic acid ethyl ester as an orange solid.
¹H NMR (DMSO-d₆/400 MHz) δ ppm 1.31 (t, J=7.12 Hz, 3H), 4.24 (q, J=7.12 Hz, 2H), 7.26 (s, 1H), 7.71 (d, J=6.22 Hz, 2H) 8.54 (d, J=6.22 Hz, 2H), 12.85 (s, 1H); ESI (+) MS: m/z 295 (MH⁺).

Step 3: Saponification to Carboxylic Acid (31)

Ester 30 (1.0 g, 3.74 mmol), dissolved in 8 ml of 4M aq NaOH and 8 mL EtOH, was refluxed for 4 h. The solution was cooled and neutralized with AcOH. The precipitate was filtered and washed with water and acetone to afford 850 mg (85%) of 2-bromo-5-pyridin-4-yl-1H-pyrrole-3-carboxylic acid as a white solid.
¹H NMR (DMSO-d₆/400 MHz) δ ppm 7.33 (s, 1H), 7.83 (d, J=6.00 Hz, 2H), 8.58 (d, J=6.00 Hz, 2H), 12.37 (bs, 1H), 12.91 (s, 1H); MS: m/z 266 [M-H].

Step 4: Condensation to Amide (R1)

Acid 31 (450 mg, 1.68 mmol) was dissolved in anhydrous THF (20 mL) in the presence of DIEA (1.27 mL, 7.30 mmol). To the solution, cooled to 0° C., EDCI (1.0 g, 5.5 mmol) and HOBT.NH₃ (812 mg, 5.34 mmol) were added. The reaction mixture was left overnight at rt. The solvent was evaporated, water was added and the slurry was extracted with DCM. The crude was purified by flash chromatography (DCM/MeOH 95:5) to yield 150 mg (33%) of 2-bromo-5-pyridin-4-yl-1H-pyrrole-3-carboxylic acid amide as a pale yellow solid.
¹H NMR (DMSO-d₆/400 MHz) δ ppm 7.02 (s, 2H), 7.29 (s, 1H), 7.59 (d, J=6.25 Hz, 2H), 8.52 (d, J=6.25 Hz, 2H), 12.54 (s, 1H); ESI (+) MS: m/z 267 (MH⁺).

Step 5: Suzuki Coupling to Amides (A11)

To a solution of amide R1 (110 mg, 0.41 mmol) in deoxygenated toluene/EtOH 1:1 (5 mL), deoxygenated 1M aq Na₂CO₃ (1.1 mL, 1.12 mmol), LiCl (57 mg, 1.35 mmol), the conveniently substituted phenyl boronic acid (0.67 mmol) and (Ph₃P)₂PdCl₂ (3 mg) were added and the mixture was stirred at 100° C. until disappearance of the starting material.

The solvent was evaporated and the crude was purified by flash chromatography (eluant:DCM/MeOH 95:5). When required the product was dissolved in EtOH, treated with 2N HCl in Et₂O until precipitation of the hydrochloride salt which was filtered affording 2-(3-methoxy-phenyl)-5-pyridin-4-yl-1H-pyrrole-3-carboxylic acid amide (68% yield).

¹H NMR (DMSO-d₆/400 MHz) δ ppm 3.83 (s, 3H), 6.66 (bs, 2H), 7.28 (m, 3H), 7.40 (m, 2H), 8.24 (d, J=6.82 Hz, 2H), 9.11 (d, J=6.82 Hz); ESI (+) MS: m/z 294 (MH⁺).

By using this procedure the following compounds were obtained.

Example 36

2-(4-Methoxy-phenyl)-5-pyridin-4-yl-1H-pyrrole-3-carboxylic Acid Amide Hydrochloride (A12)

¹H NMR (DMSO-d₆/400 MHz) δ ppm 3.84 (s, 3H), 7.07 (d, J=8.90 Hz, 2H), 7.33 (bs, 2H), 7.67 (d, J=8.90 Hz, 2H), 7.73 (s, 1H), 8.22 (d, J=6.50 Hz, 2H), 8.72 (d, J=6.50 Hz, 2H), 12.28 (s, 1H); ESI (+) MS: m/z 294 (MH⁺).

Example 37

2-(2-Methoxy-phenyl)-5-pyridin-4-yl-1H-pyrrole-3-carboxylic Acid Amide Hydrochloride (A10)

¹H NMR (DMSO-d₆/400 MHz) δ ppm 3.76 (s, 3H), 6.95 (bs, 2H), 7.06 (t, J=8.05 Hz, 1H), 7.16 (d, J=8.05 Hz, 1H), 7.40 (dd, J=1.71 Hz, 7.44 Hz, 1H), 7.46 (m, 1H), 7.73 (s, 1H), 8.15 (d, J=7.00 Hz, 2H), 8.71 (d, J=7.00 Hz, 2H), 12.42 (s, 1H); ESI (+) MS: m/z 294 (MH⁺).

Example 38

2-(4-Nitro-phenyl)-5-pyridin-4-yl-1H-pyrrole-3-carboxylic Acid Amide (A15)

¹H NMR (DMSO-d₆/400 MHz) δ ppm 7.40 (bs, 2H), 7.70 (s, 1H), 8.02 (d, J=8.78 Hz, 2H), 8.19 (d, J=6.20 Hz, 2H), 8.32 (d, J=8.78 Hz, 2H), 8.77 (d, J=6.20 Hz, 2H), 12.57 (bs, 1H); ESI (+) MS: m/z 309 (MH⁺).

Example 39

5-(2-Amino-pyrimidin-4-yl)-2-bromo-1H-pyrrole-3-carboxylic Acid Amide (R2) and 5-(2-amino-pyrimidin-4-yl)-2-thiophen-3-yl-1H-pyrrole-3-carboxylic Acid Amide (G1)

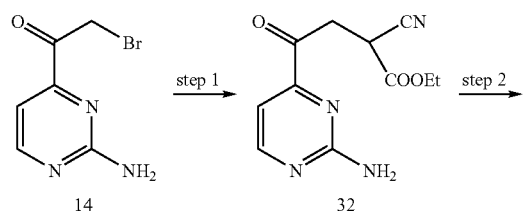

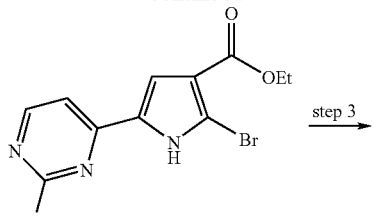

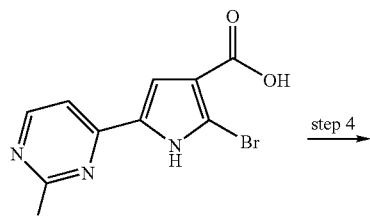

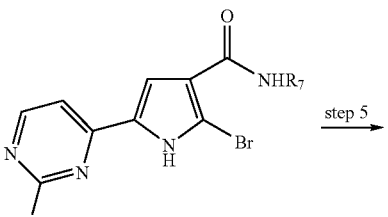

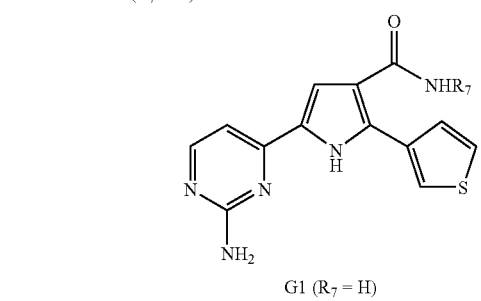

Step 1: Condensation to Cyanoester (32)

Ethylcyanoacetate (5.3 mL, 0.05 mol) was added to a suspension of sodium metal (1.15 g, 0.05 mol) in 150 mL of anhydrous EtOH at 0° C. After sodium dissolution the reaction mixture was concentrated and the resultant solid was added to a solution of bromoketone 14 (15 g, 0.05 mol) in 300 mL of anhydrous THF and DIEA (8.8 mL, 0.05 mol). The reaction mixture was stirred overnight at rt, concentrated and the residue was suspended in water and extracted with DCM. The organic extracts were dried (Na₂SO₄) and concentrated. The crude was purified by flash chromatography (DCM/MeOH 95:5) to give 4.5 g (37%) of 4-(2-amino-pyrimidin-4-yl)-2-cyano-4-oxo-butyric acid ethyl ester as an oil.

¹H NMR (DMSO-d₆/400 MHz) δ ppm 1.21 (t, J=7.08 Hz, 3H), 3.73 (d, J=5.61 Hz, 2H), 4.18 (q, J=7.08 Hz, 2H), 4.58 (t, J=5.61 Hz, 1H), 6.97 (d, J=4.88 Hz, 1H), 7.04 (bs, 2H), 8.52 (d, J=4.88 Hz, 1H); ESI (+) MS: m/z 249 (MH⁺).

Step 2: Formation of Pyrrole Ring (33)

A solution of cyanoester 32 (364 mg, 1.47 mmol) in anhydrous Et₂O and DCM (1:1, 10 mL) was added dropwise to 4.5 mL of 33% HBr in AcOH at 0° C. The mixture was left at 0° C. for 30 min and then at rt until disappearance of the starting material. The solid was filtered, washed with acetone and MeOH, neutralized with 7N NH$_3$ in MeOH to afford 400 mg (88%) of 5-(2-amino-pyrimidin-4-yl)-2-bromo-1H-pyrrole-3-carboxylic acid ethyl ester.

$^1$H NMR (DMSO-d$_6$/400 MHz) δ ppm 1.26 (t, J=7.10 Hz, 3H), 4.20 (q, J=7.10 Hz, 2H), 6.43 (bs, 2H), 6.99 (d, J=5.24 Hz, 1H), 7.23 (s, 1H), 8.23 (d, J=5.24 Hz, 1H); ESI (+) MS: m/z 312 (MH$^+$).

Step 3: Saponification to Carboxylic Acid (34)

A solution of ester 33 (2 g, 6 mmol), in 15 mL of EtOH and 15 mL of 4M aq NaOH, was refluxed at 100° C. for 6 h. The acid was precipitated with AcOH, filtered and washed with acetone to give 80 mg (88%) of 5-(2-amino-pyrimidin-4-yl)-2-bromo-1H-pyrrole-3 carboxylic acid.

$^1$H NMR (DMSO-d$_6$/400 MHz) δ ppm 6.06 (br, 2H), 6.87 (d, J=5.20 Hz, 1H), 7.08 (s, 1H), 8.00 (d, J=5.20 Hz, 1H); MS: m/z 282 [M-H].

Step 4: Condensation to Amides (R2)

A solution of 500 mg (1.77 mmol) of acid 34 in 20 mL of dry THF and DIEA (0.6 mL, 3.54 mmol) was stirred at 0° C. EDCI (508 mg, 2.65 mmol) and HOBT.NH$_3$ (404 mg, 2.65 mmol) were added and the reaction mixture was stirred overnight at rt. The solution was concentrated and the crude was purified by HPLC preparative. Obtained 5-(2-amino-pyrimidin-4-yl)-2-bromo-1H-pyrrole-3-carboxylic acid amide.

$^1$H NMR (DMSO-d$_6$/400 MHz) δ ppm 6.97 (d, J=5.57 Hz, 1H) 7.00 (bs, 1H) 7.17 (bs, 1H) 8.24 (d, J=5.57 Hz, 1H) 12.66 (bs, 1H); ESI (+) MS: m/z 283 (MH$^+$).

Step 5: Suzuki Coupling to Amides (G1)

Bromoamide R2 (224 mg, 0.79 mmol) was dissolved in EtOH (6 mL) and toluene (6 mL), LiCl (99 mg, 2.37 mmol), 1M aq Na$_2$CO$_3$ (1.97 mmol), 3-thiophenboronic acid (152 mg, 1.18 mmol) and (Ph$_3$P)$_2$PdCl$_2$ (6 mg, 0.008 mmol) were added and the reaction mixture was heated to reflux for 6 hr and then overnight at rt. The solvent was evaporated under reduced pressure and the crude material was purified by flash chromatography (DCM/MeOH 9:1) to afford 120 mg (53%) of 5-(2-amino-pyrimidin-4-yl)-2-thiophen-3-yl-1H-pyrrole-3-carboxylic acid amide.

$^1$H NMR (DMSO-d$_6$/400 MHz) δ ppm 6.36 (bs, 2H), 6.87 (bs, 2H), 7.01 (d, J=5.24 Hz, 1H), 7.26 (d, J=2.44 Hz, 1H), 7.54 (d, J=2.93 Hz, 5.00, 1H), 7.65 (dd, J=1.22 Hz, 5.00, 1H), 8.11 (dd, J=1.22 Hz, 2.93, 1H), 8.20 (d, J=5.24 Hz, 1H), 11.52 (bs, 1H); ESI (+) MS: m/z 286 (MH$^+$).

The above procedure was employed to synthesize the following compounds.

Example 40

5-(2-Amino-pyrimidin-4-yl)-2-(4-fluoro-2-methyl-phenyl)-1H-pyrrole-3-carboxylic Acid Amide (F13)

$^1$H NMR (DMSO-d$_6$/400 MHz) δ ppm 2.15 (s, 3H), 6.31 (bs, 2H), 6.69 (bs, 1H), 6.92 (d, J=5.24 Hz, 1H), 7.05 (td, J=8.41, 2.56 Hz, 1H), 7.05 (dd, J=7.68, 2.56 Hz, 1H), 7.06 (bs, 1H), 7.28 (dd, J=8.41, 7.68 Hz, 1H), 7.32 (d, J=2.56 Hz, 1H), 8.18 (d, J=5.24 Hz, 1H), 11.75 (bs, 1H); ESI (+) MS: m/z 312 (MH$^+$).

Example 41

5-(2-Amino-pyrimidin-4-yl)-2-(5-fluoro-2-methyl-phenyl)-1H-pyrrole-3-carboxylic Acid Amide (F14)

$^1$H NMR (DMSO-d$_6$/400 MHz) δ ppm 2.11 (s, 3H), 6.32 (bs, 2H), 6.72 (bs, 1H), 6.93 (d, J=5.24 Hz, 1H), 7.04-7.19 (m, 3H), 7.25-7.31 (m, 1H), 7.33 (d, J=2.44 Hz, 1H), 8.18 (d, J=5.24 Hz, 1H), 11.82 (bs, 1H); ESI (+) MS: m/z 312 (MH$^+$).

Example 42

5-(2-Amino-pyrimidin-4-yl)-2-(2,3-dimethyl-phenyl)-1H-pyrrole-3-carboxylic Acid Amide (F15)

See Ex. 17.

Example 43

5-(2-Amino-pyrimidin-4-yl)-2-(2,3-difluoro-phenyl)-1H-pyrrole-3-carboxylic Acid Amide (F16)

$^1$H NMR (DMSO-d$_6$/400 MHz) δ ppm 6.38 (bs, 2H), 6.82 (bs, 1H), 6.95 (d, J=5.24 Hz, 1H), 7.20-7.28 (m, 1H), 7.28-7.34 (m, 1H), 7.35 (d, J=2.56 Hz, 1H), 7.39-7.50 (m, 2H), 8.23 (d, J=5.24, 1H), 12.00 (bs, 1H); ESI (+) MS: m/z 316 (MH$^+$).

Example 44

5-(2-Amino-pyrimidin-4-yl)-2-(2,4-difluoro-phenyl)-1H-pyrrole-3-carboxylic Acid Amide (F17)

$^1$H NMR (DMSO-d$_6$/400 MHz) δ ppm 6.41 (bs, 2H), 6.77 (bs, 1H), 6.94 (d, J=5.24 Hz, 1H), 7.13 (m, 1H), 7.28 (m, 1H), 7.35 (d, J=2.56 Hz, 1H), 7.38 (bs, 1H), 7.54 (m, 1H), 8.23 (d, J=5.24 Hz, 1H), 11.93 (bs, 1H); ESI (+) MS: m/z 316 (MH$^+$).

Example 45

5-(2-Amino-pyrimidin-4-yl)-2-(2,5-difluoro-phenyl)-1H-pyrrole-3-carboxylic Acid Amide (F18)

$^1$H NMR (DMSO-d$_6$/400 MHz) δ ppm 6.40 (bs, 2H) 6.81 (bs, 1H) 6.94 (d, J=5.37 Hz, 1H) 7.33 (d, J=2.44 Hz, 1H) 7.42 (bs, 1H) 8.22 (d, J=5.24 Hz, 1H) 11.95 (bs, 1H); ESI (+) MS: m/z 316 (MH$^+$).

Example 46

5-(2-Amino-pyrimidin-4-yl)-2-(2-chloro-phenyl)-1H-pyrrole-3-carboxylic Acid Amide (F19)

$^1$H NMR (DMSO-d$_6$/400 MHz) δ ppm 6.37 (bs, 2H), 6.69 (bs, 1H), 6.93 (d, J=5.24 Hz, 1H), 7.19 (bs, 1H), 7.33 (d, J=2.56 Hz, 1H), 7.35-7.45 (m, 3H), 7.48-7.53 (m, 1H), 8.19 (d, J=5.24 Hz, 1H), 11.90 (bs, 1H); ESI (+) MS: m/z 314 (MH$^+$).

Example 47

5-(2-Amino-pyrimidin-4-yl)-2-(3-chloro-phenyl)-1H-pyrrole-3-carboxylic Acid Amide (F20)

$^1$H NMR (DMSO-d$_6$/400 MHz) δ ppm 6.38 (bs, 2H), 6.90 (bs, 1H), 7.01 (d, J=5.24 Hz, 1H), 7.27 (d, J=2.44 Hz, 1H), 7.35-7.44 (m, 2H), 7.47 (bs, 1H), 7.59-7.65 (m, 1H), 7.73 (t, J=1.22 Hz, 1H), 8.23 (d, J=5.24, 1H), 11.79 (bs, 1H); ESI (+) MS: m/z 314 (MH$^+$).

Example 48

5-(2-Amino-pyrimidin-4-yl)-2-(4-chloro-phenyl)-1H-pyrrole-3-carboxylic Acid Amide (F21)

$^1$H NMR (DMSO-d$_6$/400 MHz) δ ppm 6.33 (bs, 2H), 6.86 (bs, 1H), 6.99 (d, J=5.24 Hz, 1H), 7.28 (d, J=2.07 Hz, 1H), 7.38-7.49 (m, 3H), 7.63-7.70 (m, 2H), 8.21 (d, J=5.24 Hz, 1H), 11.74 (bs, 1H); ESI (+) MS: m/z 314 (MH$^+$).

Example 49

5-(2-Amino-pyrimidin-4-yl)-2-(4-isobutyl-phenyl)-1H-pyrrole-3-carboxylic Acid Amide (F22)

$^1$H NMR (DMSO-d$_6$/400 MHz) δ ppm 0.90 (d, J=6.58 Hz, 6H), 1.80-1.95 (m, 1H), 2.48 (m, 2H), 6.35 (bs, 2H), 6.80 (bs, 1H), 7.01 (d, J=5.24 Hz, 1H), 7.19 (d, J=8.17 Hz, 2H), 7.25 (d, J=2.56 Hz, 1H), 7.28 (bs, 1H), 7.56 (d, J=8.17 Hz, 2H), 8.19 (d, J=5.24 Hz, 1H), 11.56 (bs, 1H); ESI (+) MS: m/z 336 (MH$^+$).

Example 50

5-(2-Amino-pyrimidin-4-yl)-2-(2-chloro-4-fluoro-phenyl)-1H-pyrrole-3-carboxylic Acid Amide (F23)

$^1$H NMR (DMSO-d$_6$/400 MHz) δ ppm 6.38 (bs, 2H), 6.72 (bs, 1H), 6.92 (d, J=5.24 Hz, 1H), 7.22-7.33 (m, 2H), 7.35 (d, J=2.56 Hz, 1H), 7.45-7.54 (m, 2H), 8.22 (d, J=5.24 Hz, 1H), 11.95 (bs, 1H); ESI (+) MS: m/z 336 (MH$^+$).

Example 51

5-(2-Amino-pyrimidin-4-yl)-2-(2,5-dimethyl-phenyl)-1H-pyrrole-3-carboxylic Acid Amide (F24)

$^1$H NMR (DMSO-d$_6$/400 MHz) δ ppm 2.11 (s, 3H) 2.31 (s, 3H) 6.41 (bs, 2H) 6.70 (bs, 1H) 6.83 (bs, 1H) 6.98 (d, J=5.37 Hz, 1H) 7.1-7.18 (m, 3H) 7.34 (d, J=2.68 Hz, 1H) 8.19 (d, J=5.37 Hz, 1H) 11.74 (bs, 1H); ESI (+) MS: m/z 308 (MH$^+$).

Example 52

5-(2-Amino-pyrimidin-4-yl)-2-(5-chloro-2-methyl-phenyl)-1H-pyrrole-3-carboxylic Acid Amide (F25)

$^1$H NMR (DMSO-d$_6$/400 MHz) δ ppm 2.12 (s, 3H), 6.35 (bs, 2H), 6.73 (bs, 1H), 6.93 (d, J=5.24 Hz, 1H), 7.22 (bs, 1H), 7.25-7.30 (m, 2H), 7.32-7.36 (m, 2H), 8.20 (d, J=5.24 Hz, 1H), 11.85 (bs, 1H); ESI (+) MS: m/z 328 (MH$^+$).

Example 53

5-(2-Amino-pyrimidin-4-yl)-2-(2,4-dichloro-phenyl)-1H-pyrrole-3-carboxylic Acid Amide (F26)

See Ex. 19.

Example 54

5-(2-Amino-pyrimidin-4-yl)-2-(5-chloro-2-fluoro-phenyl)-1H-pyrrole-3-carboxylic Acid Amide (F27)

$^1$H NMR (DMSO-d$_6$/400 MHz) δ ppm 6.37 (bs, 2H) 6.80 (bs, 1H) 6.93 (d, J=5.24 Hz, 1H) 7.28 (t, J=9.21 Hz, 1H) 7.33 (d, J=2.44 Hz, 1H) 7.44 (bs, 1H) 7.47 (ddd, J=8.84, 4.33, 2.80 Hz, 1H) 7.55 (dd, J=6.22, 2.68 Hz, 1H) 8.22 (d, J=5.24 Hz, 1H) 11.98 (bs, 1H); ESI (+) MS: m/z 332 (MH$^+$).

Example 55

5-(2-Amino-pyrimidin-4-yl)-2-(2-fluoro-4-methyl-phenyl)-1H-pyrrole-3-carboxylic Acid Amide (F28)

$^1$H NMR (DMSO-d$_6$/400 MHz) δ ppm 2.37 (s, 3H), 6.37 (bs, 2H), 6.73 (bs, 1H), 6.95 (d, J=5.24 Hz, 1H), 7.02-7.09 (m, 2H), 7.26 (bs, 1H), 7.30 (d, J=2.56 Hz, 1H), 7.37 (t, J=7.90 Hz, 1H), 8.20 (d, J=5.24 Hz, 1H), 11.78 (bs, 1H); ESI (+) MS: m/z 312 (MH$^+$).

Example 56

5-(2-Amino-pyrimidin-4-yl)-2-(2-fluoro-5-methyl-phenyl)-1H-pyrrole-3-carboxylic Acid Amide (F29)

$^1$H NMR (DMSO-d$_6$/400 MHz) δ ppm 2.33 (s, 3H) 6.42 (bs, 2H) 6.75 (bs, 1H) 6.97 (d, J=5.37 Hz, 1H) 7.11 (dd, J=9.88, 8.41 Hz, 1H) 7.19-7.25 (m, 1H) 7.31 (bs, 1H) 7.30 (dd, J=6.77, 2.01 Hz, 1H) 7.32 (d, J=2.44 Hz, 1H) 8.21 (d, J=5.37 Hz, 1H) 11.85 (bs, 1H); ESI (+) MS: m/z 312 (MH$^+$).

Example 57

5-(2-Amino-pyrimidin-4-yl)-2-(2-fluoro-3-methyl-phenyl)-1H-pyrrole-3-carboxylic Acid Amide (F30)

$^1$H NMR (DMSO-d$_6$/400 MHz) δ ppm 2.27 (d, J=1.71 Hz, 3H) 6.39 (bs, 2H) 6.74 (bs, 1H) 6.95 (d, J=5.24 Hz, 1H) 7.12 (t, J=7.56 Hz, 1H) 7.28 (bs, 1H) 8.20 (d, J=5.37 Hz, 1H) 11.81 (bs, 1H); ESI (+) MS: m/z 312 (MH$^+$).

Example 58

5-(2-Amino-pyrimidin-4-yl)-2-(5-chloro-2-fluoro-3-methyl-phenyl)-1H-pyrrole-3-carboxylic Acid Amide (F32)

$^1$H NMR (DMSO-d$_6$/400 MHz) δ ppm 2.26 (s, 3H), 6.41 (bs, 2H), 6.80 (bs, 1H), 6.95 (d, J=5.24 Hz, 1H), 7.32 (d, J=2.32 Hz, 1H), 7.33-7.37 (m, 1H), 7.38-7.47 (m, 2H), 8.21 (d, J=5.24 Hz, 1H), 11.95 (bs, 1H); ESI (+) MS: m/z 346 (MH$^+$).

Example 59

5-(2-Amino-pyrimidin-4-yl)-2-(3-chloro-2-fluoro-phenyl)-1H-pyrrole-3-carboxylic Acid Amide (F33)

$^1$H NMR (DMSO-d$_6$/400 MHz) δ ppm 6.41 (bs, 2H) 6.81 (bs, 1H) 6.94 (d, J=5.24 Hz, 1H) 7.23-7.27 (m, 1H) 7.35 (d, J=2.44 Hz, 1H) 7.42 (bs, 1H) 7.43-7.47 (m, 1H) 8.23 (d, J=5.24 Hz, 1H) 12.02 (bs, 1H); ESI (+) MS: m/z 332 (MH$^+$).

Example 60

5-(2-Amino-pyrimidin-4-yl)-2-(2,3-dichloro-phenyl)-1H-pyrrole-3-carboxylic Acid Amide (F34)

$^1$H NMR (DMSO-d$_6$/400 MHz) δ ppm 6.35 (bs, 2H), 6.73 (bs, 1H), 6.90 (d, J=5.24 Hz, 1H), 7.34 (bs, 1H), 7.38-7.42 (m, 2H), 7.65-7.70 (m, 2H), 8.21 (d, J=5.24 Hz, 1H), 12.00 (bs, 1H); ESI (+) MS: m/z 349 (MH+).

Example 61

5-(2-Amino-pyrimidin-4-yl)-2-(2-fluoro-3-methoxy-phenyl)-1H-pyrrole-3-carboxylic Acid Amide (F35)

$^1$H NMR (DMSO-$d_6$/400 MHz) δ ppm 3.86 (s, 3H) 6.39 (bs, 2H) 6.74 (bs, 1H) 6.95 (d, J=5.24 Hz, 1H) 6.99-7.03 (m, 1H) 7.12-7.16 (m, 1H) 7.18-7.20 (m, 1H) 7.29 (bs, 1H) 7.30 (d, J=2.44 Hz, 1H) 8.21 (d, J=5.24 Hz, 1H) 11.86 (bs, 1H); ESI (+) MS: m/z 328 (MH+).

Example 62

5-(2-Amino-pyrimidin-4-yl)-2-benzo[b]thiophen-5-yl-1H-pyrrole-3-carboxylic Acid Amide (G15)

Example 63

2-Bromo-5-(3-fluoro-pyridin-4-yl)-1H-pyrrole-3-carboxylic Acid Amide (R3) and 5-(3-fluoro-pyridin-4-yl)-2-phenyl-1H-pyrrole-3-carboxylic Acid Amide (E1)

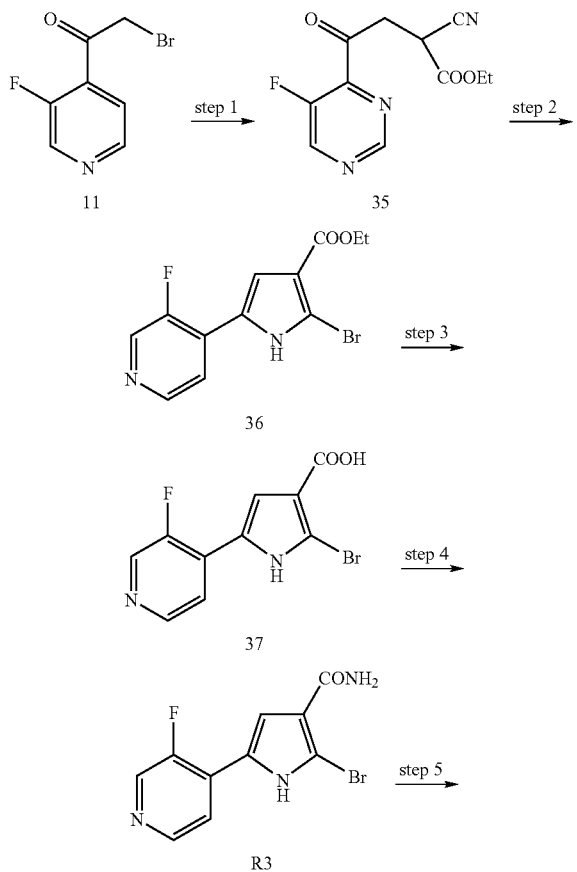

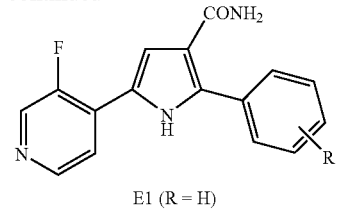

E1 (R = H)

Step 1: Condensation to Cyanoester (35)

Ethylcyanoacetate (715 μL, 6.7 mmol) was added to a suspension of sodium metal (154 mg, 6.7 mmol) in 20 mL of anhydrous EtOH at 0° C. The solution was stirred until sodium dissolved completely. The solvent was evaporated and the solid was added to a solution of bromoketone 11 (2 g, 6.7 mmol) and DIEA (1.16 mL, 6.7 mmol) in 40 mL of anhydrous THF. The mixture was stirred overnight at rt. The solvent was evaporated, the residue was suspended in water and extracted with DCM. The organic extracts were dried (Na$_2$SO$_4$) and the crude material was purified by flash chromatography (DCM/MeOH 98:2) to afford 2-cyano-4-(3-fluoro-pyridin-4-yl)-4-oxo-butyric acid ethyl ester as an oil.

$^1$H NMR (DMSO-$d_6$/400 MHz) δ ppm 1.22 (t, J=7.07 Hz, 3H), 3.78 (m, 2H), 4.20 (q, J=7.07 Hz, 2H), 4.61 (t, J=5.37 Hz, 1H), 7.81 (m, 1H), 8.64 (dd, J=1.22, 5.00 Hz, 1H), 8.82 (d, J=2.56 Hz, 1H); ESI (+) MS: m/z 251 (MH+).

Step 2: Formation of the Pyrrole Ring (36)

A solution of cyanoester 35 (1.0 g, 4 mmol) in anhydrous Et$_2$O (3 mL) and DCM (2 mL) was added to 33% HBr in AcOH (12 mL), cooled at 0° C. The reaction mixture was stirred for 3 h, the precipitate was filtered, washed with acetone and MeOH and neutralized with 7N NH$_3$ in MeOH. The solvent was evaporated to give 1.0 g (80%) of 2-bromo-5-(3-fluoro-pyridin-4-yl)-1H-pyrrole-3-carboxylic acid ethyl ester as a solid.

$^1$H NMR (DMSO-$d_6$/400 MHz) δ ppm 1.26 (t, J=7.07 Hz, 3H), 4.20 (q, J=7.07 Hz, 2H), 7.08 (d, J=3.53 Hz, 1H), 7.30 (bs, 1H), 7.83 (m, 1H), 8.39 (dd, J=0.85, 5.12 Hz, 1H), 8.55 (d, J=3.41 Hz, 1H); ESI (+) MS: m/z 314 (MH+).

Step 3: Saponification to Carboxylic Acid (37)

Ester 36 was dissolved in 8 mL of EtOH and 8 mL of 1M aq NaOH and heated at 100° C. for 6 h. The product was precipitated with AcOH, the solid was filtered and washed with acetone to afford 700 mg (77%) of 2-bromo-5-(3-fluoro-pyridin-4-yl)-1H-pyrrole-3-carboxylic acid.

$^1$H NMR (DMSO-$d_6$/400 MHz) δ ppm 6.98 (d, J=5.12 Hz, 1H), 7.81 (q, J=5.12 Hz, 1H), 8.13 (d, J=5.60 Hz, 1H), 8.25 (d, J=4.02 Hz, 1H); MS: m/z 284 [M-H].

Step 4: Condensation to Amide (R3)

Acid 37 (1.68 mmol) was dissolved in anhydrous THF (20 mL) in the presence of DIEA (1.27 mL, 7.30 mmol). To the solution, cooled to 0° C., EDCI (1.0 g, 5.5 mmol) and HOBT.NH$_3$ (812 mg, 5.34 mmol) were added. The reaction mixture was left overnight at rt. The solvent was evaporated, water was added and the slurry was extracted with DCM. The crude was purified by flash chromatography (DCM/MeOH 98:2) to yield 2-bromo-5-(3-fluoro-pyridin-4-yl)-1H-pyrrole-3-carboxylic acid amide as a yellow solid (42% yield).

$^1$H NMR (DMSO-d$_6$/400 MHz) δ ppm 7.09 (s, 2H) 7.35 (s, 1H) 7.98 (d, J=4.83 Hz, 1H) 8.47 (d, J=4.84 Hz, 1H) 8.61 (d, J=0.91 Hz, 1H) 12.05 (s, 1H); ESI (+) MS: m/z 285 (MH$^+$).

Step 5: Suzuki Coupling to Amide (E1)

To a solution of amide R3 (0.8 mmol) in deoxygenated toluene/EtOH 1:1 (10 mL), deoxygenated 1M aq Na$_2$CO$_3$ (2.2 mL, 2.2 mmol), LiCl (2.7 mmol), phenyl boronic acid (1.4 mmol) and (Ph$_3$P)$_2$PdCl$_2$ (6 mg) were added and the mixture was stirred at 100° C. until disappearance of the starting material. The solvent was evaporated and the crude was purified by flash chromatography (eluant:DCM/MeOH 95:5). When required the product was dissolved in EtOH, treated with 2N HCl in Et$_2$O until precipitation of the hydrochloride salt which was filtered affording 5-(3-fluoro-pyridin-4-yl)-2-phenyl-1H-pyrrole-3-carboxylic acid amide (74% yield).

Example 64

2-(4-Methoxy-phenyl)-5-pyridin-4-yl-1H-pyrrole-3-carboxylic Acid Amide (A12)

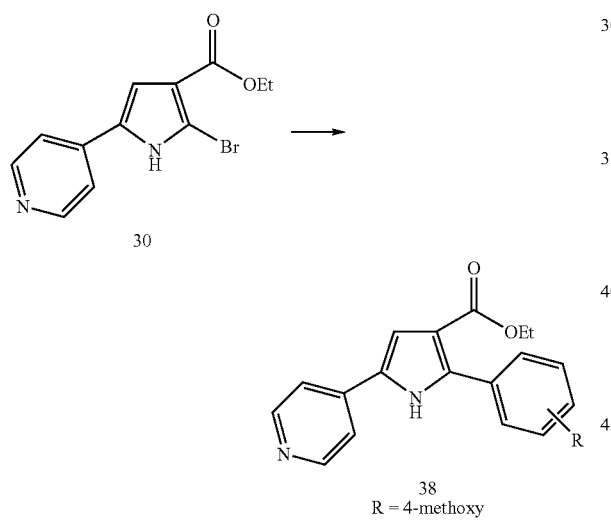

To ester 30 (40 mg, 0.135 mmol), dissolved in deoxygenated EtOH/toluene 1:1 (2 mL), 4-methoxy phenyl boronic acid (31 mg, 0.2 mmol), LiCl (17 mg, 0.4 mmol), deoxygenated 1M aq Na$_2$CO$_3$ (340 μL, 0.34 mmol) and (Ph$_3$P)$_2$PdCl$_2$ (1 mg) were added and the reaction mixture was stirred at reflux until disappearance of the starting material (2.5 h). The solvent was evaporated, water was added and the slurry was extracted with DCM and washed with water. The organic layers were dried (Na$_2$SO$_4$) and the crude was purified by flash chromatography (DCM/MeOH 95:5) to afford 28 mg (70%) of 2-(4-methoxy-phenyl)-5-pyridin-4-yl-1H-pyrrole-3-carboxylic acid ethyl ester 38 as a solid.

$^1$H NMR (DMSO-d$_6$/400 MHz) δ ppm 1.20 (t, J=7.00 Hz, 3H), 3.82 (s, 3H), 4.10 (q, J=7.00 Hz, 2H), 7.10 (d, J=8.80 Hz, 2H), 7.70 (d, J=8.80 Hz, 2H), 7.68 (s, 1H), 8.25 (d, J=6.40 Hz, 2H), 8.70 (d, J=6.40 Hz, 2H), 12.30 (s, 1H); ESI (+) MS: m/z 323 (MH$^+$).

Ester 38 can be transformed in amide A12 as already described in Example 1.

Example 65

5-pyridin-4-yl-2-p-tolyl-1H-pyrrole-3-carboxylic Acid Amide (A9)

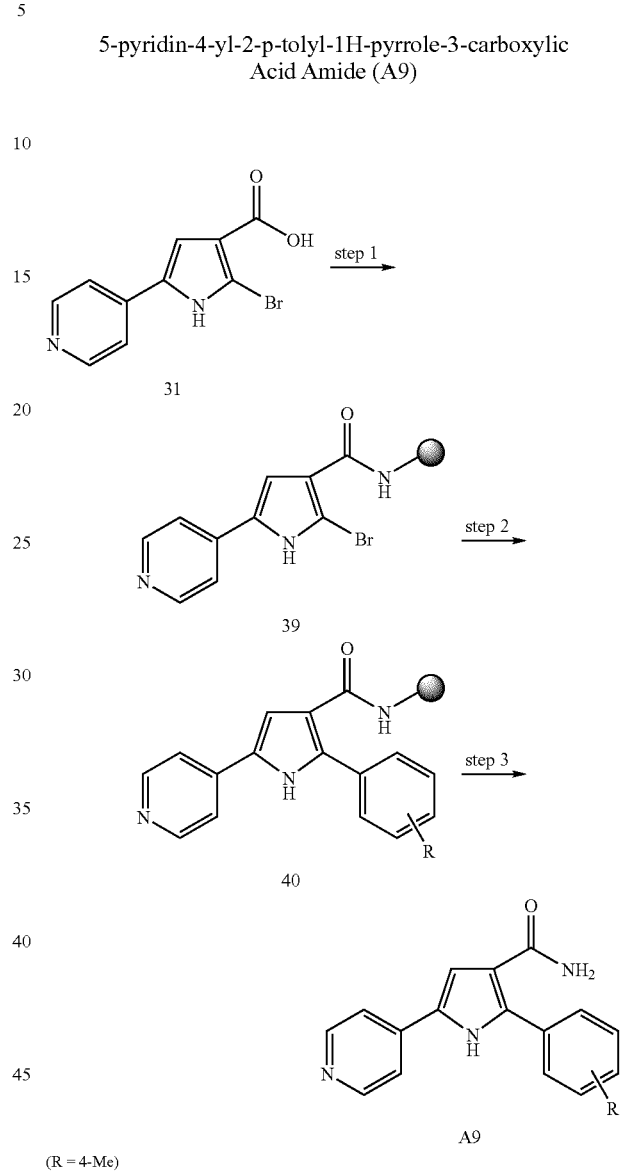

Step 1: Condensation to Amide (39)

Acid 31 (500 mg, 1.87 mmol) was loaded on Rink Amide MBHA resin (1.38 g, 0.935 mmol, theoretical loading 0.68 mmol/g) by stirring with DIEA (0.65 mL, 3.74 mmol), EDCI (537 mg, 2.8 mmol) and HOBT (379 mg, 2.8 mmol) in 20 mL of DMF at rt overnight. The substitution rate was 78% and the resin had been previously cleaved with 20% piperidine in DMF.

Step 2: Suzuki Coupling to Amides (40)

The supported amide 39 (100 mg, 0.052 mmol) was heated at 100° C. overnight with 4-methylphenylboronic acid (35 mg, 0.26 mmol), LiCl (9 mg, 0.208 mmol), Cs$_2$CO$_3$ (85 mg, 0.26 mmol) and $(PhP_3)_2PdCl_2$ (7.0 mg, 0.01 mmol) in 2 mL of deoxygenated DMF and 0.1 mL of deoxygenated water.

Step 3: Cleavage to Amides (A9)

Amide 40 was cleaved with TFA/DCM 95:5. The solution was concentrated and the crude was purified by preparative HPLC to afford 5-pyridin-4-yl-2-p-tolyl-1H-pyrrole-3-carboxylic acid amide as a solid (yield: 54%).

$^1$H NMR (DMSO-$d_6$/400 MHz) δ ppm 2.37 (s, 3H), 7.00 (bs, 2H), 7.25 (d, J=8.00 Hz, 2H), 7.34 (d, J=2.56 Hz, 1H), 7.58 (d, J=8.00 Hz, 2H), 7.79 (d, J=6.22 Hz, 2H), 8.56 (d, J=6.22 Hz, 2H), 11.85 (s, 1H); ESI (+) MS: m/z 278 (MH$^+$).

The above procedure was employed to synthesize the following compounds.

Example 66

2-(3-Methoxy-phenyl)-5-pyridin-4-yl-1H-pyrrole-3-carboxylic Acid Amide (A11)

$^1$H NMR (DMSO-$d_6$/400 MHz) δ ppm 3.83 (s, 3H), 6.66 (bs, 2H), 7.28 (m, 3H), 7.40 (m, 2H), 8.24 (d, J=6.82 Hz, 2H), 9.11 (d, J=6.82 Hz, 2H), 12.32 (s, 1H); ESI (+) MS: m/z 294 (MH$^+$).

Example 67

2-(2-Nitro-phenyl)-5-pyridin-4-yl-1H-pyrrole-3-carboxylic Acid Amide (A13)

$^1$H NMR (DMSO-$d_6$/400 MHz) δ ppm 6.96 (bs, 2H), 7.37 (s, 1H), 7.58-7.65 (m, 4H), 7.79 (m, 1H), 8.07 (dd, J=1.22, 8.17 Hz, 1H), 8.55 (d, J=6.22 Hz, 2H), 12.19 (s, 1H); ESI (+) MS: m/z 309 (MH$^+$).

Example 68

2-(3-Nitro-phenyl)-5-pyridin-4-yl-1H-pyrrole-3-carboxylic Acid Amide (A14)

$^1$H NMR (DMSO-$d_6$/400 MHz) δ ppm 7.30 (bs, 2H), 7.35 (d, J=2.69 Hz, 1H), 7.76 (m, 3H), 8.15 (m, 1H), 8.22 (m, 1H), 8.58 (dd, J=1.58, 4.63 Hz, 2H), 8.61 (t, J=1.81 Hz, 1H), 12.07 (s, 1H); ESI (+) MS: m/z 309 (MH$^+$).

Example 69

5-Pyridin-4-yl-2-o-tolyl-1H-pyrrole-3-carboxylic Acid Amide (A7)

$^1$H NMR (DMSO-$d_6$/400 MHz) δ ppm 2.19 (s, 3H), 6.78 (bs, 2H), 7.25-7.38 (m, 5H), 7.64 (d, J=5.90 Hz, 2H), 8.50 (d, J=5.90 Hz, 2H), 11.90 (s, 1H); ESI (+) MS: m/z 278 (MH$^+$).

Example 70

5-Pyridin-4-yl-2-m-tolyl-1H-pyrrole-3-carboxylic Acid Amide (A8)

$^1$H NMR (DMSO-$d_6$/400 MHz) δ ppm 2.20 (s, 3H), 6.90 (bs, 2H), 7.20-7.40 (m, 5H), 7.70 (d, J=6.00 Hz, 2H), 8.55 (d, J=6.00 Hz, 2H), 11.88 (s, 1H); ESI (+) MS: m/z 278 (MH$^+$).

Example 71

2-Furan-3-yl-5-pyridin-4-yl-1H-pyrrole-3-carboxylic Acid Amide (C2)

$^1$H NMR (DMSO-$d_6$/400 MHz) δ ppm 7.17 (s, 1H), 7.30 (bs, 2H), 7.64 (s, 1H), 7.77 (s, 1H), 8.03 (d, J=6.30 Hz, 2H), 8.52 (s, 1H), 8.69 (d, J=6.30 Hz, 2H), 11.88 (s, 1H); ESI (+) MS: m/z 254 (MH$^+$).

Example 72

5-Pyridin-4-yl-2-thiophen-3-yl-1H-pyrrole-3-carboxylic Acid Amide (C1)

$^1$H NMR (DMSO-$d_6$/400 MHz) δ ppm 7.30 (bs, 2H), 7.57 (d, J=2.56 Hz, 1H), 7.62 (m, 2H), 8.03 (d, J=6.50 Hz, 2H), 8.14 (m, 1H), 8.66 (d, J=6.50 Hz, 2H), 12.01 (s, 1H); ESI (+) MS: m/z 270 (MH$^+$).

Example 73

2-(2,5-Dimethyl-phenyl)-5-pyridin-4-yl-1H-pyrrole-3-carboxylic Acid Amide (A19)

$^1$H NMR (DMSO-$d_6$/400 MHz) δ ppm 2.12 (s, 3H), 2.31 (s, 3H), 6.72 (bs, 2H), 7.13 (m, 2H), 7.29 (d, J=2.81 Hz, 1H), 7.62 (dd, J=1.58, 4.63 Hz, 2H), 8.48 (dd, J=1.58, 4.63 Hz, 2H), 11.86 (s, 1H); ESI (+) MS: m/z 292 (MH$^+$).

Example 74

2-(2,3-Dimethyl-phenyl)-5-pyridin-4-yl-1H-pyrrole-3-carboxylic Acid Amide (A20)

$^1$H NMR (DMSO-$d_6$/400 MHz) δ ppm 2.06 (s, 3H), 2.31 (s, 3H), 6.65 (bs, 2H), 7.16-7.32 (m, 4H), 7.63 (d, J=5.40 Hz, 2H), 8.49 (d, J=5.40 Hz, 2H), 11.88 (s, 1H); ESI (+) MS: m/z 292 (MH$^+$).

Example 75

2-(3,4-Dimethyl-phenyl)-5-pyridin-4-yl-1H-pyrrole-3-carboxylic Acid Amide (A21)

$^1$H NMR (DMSO-$d_6$/400 MHz) δ ppm 2.28 (s, 3H), 2.55 (s, 3H), 7.20 (m, 1H), 7.22 (d, J=2.81 Hz, 1H), 7.38 (m, 1H), 7.43 (s, 1H), 7.69 (d, J=5.85 Hz, 2H), 8.51 (m, 2H), 11.72 (s, 1H); ESI (+) MS: m/z 292 (MH$^+$).

Example 76

2-(3-Acetylamino-phenyl)-5-pyridin-4-yl-1H-pyrrole-3-carboxylic Acid Amide (A18)

$^1$H NMR (DMSO-$d_6$/400 MHz) δ ppm 2.06 (s, 3H), 6.99 (bs, 2H), 7.28 (m, 1H), 7.36 (m, 1H), 7.57 (d, J=2.44 Hz, 1H), 7.65 (d, J=8.17 Hz, 1H), 7.79 (s, 1H), 8.03 (d, J=6.20 Hz, 2H), 8.66 (d, J=6.20 Hz, 2H), 10.05 (s, 1H), 12.21 (s, 1H); ESI (+) MS: m/z 321 (MH$^+$).

Example 77

2-(2-Cyano-phenyl)-5-pyridin-4-yl-1H-pyrrole-3-carboxylic Acid Amide (A22)

$^1$H NMR (DMSO-$d_6$/400 MHz) δ ppm 6.88 (bs, 2H), 7.39 (s, 1H), 7.59 (m, 1H), 7.64 (m, 3H), 7.75 (t, J=7.19 Hz, 1H), 7.88 (d, J=7.08 Hz, 1H), 8.56 (d, J=4.75 Hz, 2H), 12.21 (s, 1H); ESI (+) MS: m/z 289 (MH+).

Example 78

2-(3-Cyano-phenyl)-5-pyridin-4-yl-1H-pyrrole-3-carboxylic Acid Amide (A23)

¹H NMR (DMSO-$d_6$/400 MHz) δ ppm 6.99 (bs, 2H), 7.32 (d, J=2.56 Hz, 1H), 7.64 (t, J=7.56 Hz, 1H), 7.69 (d, J=6.10 Hz, 2H), 7.82 (m, 2H), 8.03 (m, 2H), 8.14 (m, 1H), 8.56 (d, J=6.10 Hz, 2H), 11.95 (s, 1H); ESI (+) MS: m/z 289 (MH+).

Example 79

2-(3-Acetyl-phenyl)-5-pyridin-4-yl-1H-pyrrole-3-carboxylic Acid Amide (A16)

¹H NMR (DMSO-$d_6$/400 MHz) δ ppm 2.64 (s, 3H), 6.94 (bs, 2H), 7.31 (d, J=2.68 Hz, 1H), 7.57 (t, J=7.80 Hz, 1H), 7.70 (dd, J=1.59, 4.64 Hz, 2H), 7.93 (m, 2H), 8.28 (t, J=1.71 Hz, 1H), 8.54 (m, 2H), 11.94 (s, 1H); ESI (+) MS: m/z 306 (MH+).

Example 80

2-(3-Hydroxymethyl-phenyl)-5-pyridin-4-yl-1H-pyrrole-3-carboxylic Acid Amide (A17)

¹H NMR (DMSO-$d_6$/400 MHz) δ ppm 4.57 (s, 2H), 5.25 (s, 1H), 6.90 (bs, 2H), 7.29 (d, J=2.68 Hz, 1H), 7.36 (m, 2H), 7.52 (m, 1H), 7.58 (s, 1H), 7.74 (d, J=5.90 Hz, 2H), 8.53 (d, J=5.90 Hz, 2H), 11.86 (s, 1H); ESI (+) MS: m/z 294 (MH+).

Example 81

5-(2-Amino-pyrimidin-4-yl)-2-o-tolyl-1H-pyrrole-3-carboxylic Acid Amide (F2)

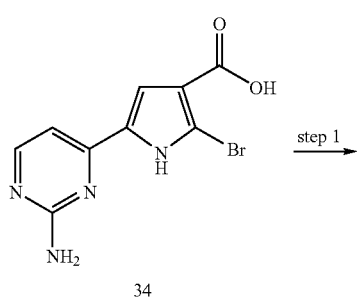

34

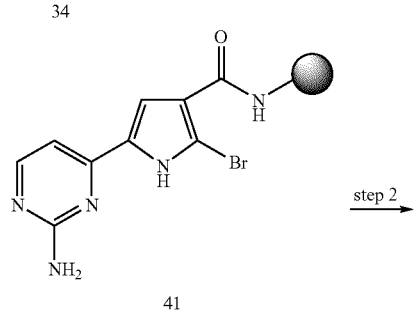

41

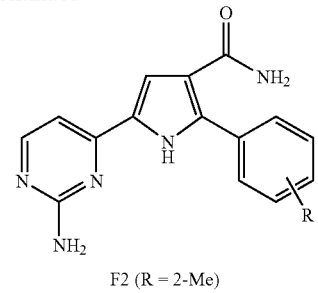

F2 (R = 2-Me)

Step 1: Condensation to Amide (41)

Acid 34 (20 mg, 0.07 mmol) was loaded on Rink Amide MBHA resin (52 mg, 0.035 mmol, theoretical loading 0.68 mmol/g) by stirring with DIEA (24 µL, 0.14 mmol), EDCI (20 mg, 0.105 mmol) and HOBT (14 mg, 0.105 mmol) in 1.5 mL of DMF overnight at rt. The resin had been previously cleaved with 20% piperidine in DMF.

Step 2: Suzuki Coupling and Cleavage to Amides (F2)

Supported amide 41 (0.035 mmol), 2-methylphenylboronic acid (24 mg, 0.175 mmol), LiCl (6 mg, 0.14 mmol), $Cs_2CO_3$ (57 mg, 0.175 mmol) and $(PhP_3)_2PdCl_2$ (5.0 mg, 0.07 mmol) in 1 mL of DMF and 50 µL $H_2O$ were heated at 100° C. overnight. The product supported on the resin was cleaved with TFA/DCM 95:5. The solution was concentrated and the crude was purified by preparative HPLC to afford 5-(2-amino-pyrimidin-4-yl)-2-o-tolyl-1H-pyrrole-3-carboxylic acid amide as a solid.

The above procedure was employed to synthesize the following compounds.

Example 82

5-(2-Amino-pyrimidin-4-yl)-2-(2-ethyl-phenyl)-1H-pyrrole-3-carboxylic Acid Amide (F3)

¹H NMR (DMSO-$d_6$/400 MHz) δ ppm 0.99 (t, J=7.56 Hz, 3H), 2.50 (m, 2H), 6.30 (bs, 2H), 6.67 (bs, 2H), 6.93 (d, J=5.24 Hz, 1H), 7.23 (m, 2H), 7.30-7.40 (m, 3H), 8.15 (d, J=5.24 Hz, 1H), 11.77 (bs, 1H); ESI (+) MS: m/z 308 (MH+).

Example 83

5-(2-Amino-pyrimidin-4-yl)-2-(2-fluoro-phenyl)-1H-pyrrole-3-carboxylic Acid Amide (F4)

¹H NMR (DMSO-$d_6$/400 MHz) δ ppm 6.92 (bs, 2H), 7.27 (m, 3H), 7.45-7.54 (m, 2H), δ 7.62 (bs, 1H), 7.84 (bs, 2H), 8.28 (d, J=6.58 Hz, 1H), 12.41 (bs, 1H); ESI (+) MS: m/z 298 (MH+)

Example 84

5-(2-Amino-pyrimidin-4-yl)-2-naphthalen-1-yl-1H-pyrrole-3-carboxylic Acid Amide (F5)

¹H NMR (DMSO-$d_6$/400 MHz) δ ppm 6.33 (bs, 2H), 6.65 (bs, 2H), 6.96 (d, J=5.27 Hz, 1H), 7.40-7.60 (m, 5H), 7.98 (m, 2H), 8.17 (d, J=5.27 Hz, 1H), 11.95 (bs, 1H); ESI (+) MS: m/z 330 (MH+).

Example 85

5-(2-Amino-pyrimidin-4-yl)-2-naphthalen-2-yl-1H-pyrrole-3-carboxylic Acid Amide (F6)

$^1$H NMR (DMSO-d$_6$/400 MHz) δ ppm 6.37 (bs, 2H), 6.87 (bs, 1H), 7.05 (d, J=5.24 Hz, 1H), 7.32 (d, J=2.32 Hz, 1H), 7.39 (bs, 1H), 7.51-7.59 (m, 2H), 7.78 (dd, J=8.41, 1.71 Hz, 1H), 7.88-7.97 (m, 3H), 8.16 (d, J=1.22 Hz, 1H), 8.23 (d, J=5.24 Hz, 1H), 11.80 (bs, 1H); ESI (+) MS: m/z 330 (MH$^+$).

Example 86

5-(2-Amino-pyrimidin-4-yl)-2-(4-phenoxy-phenyl)-1H-pyrrole-3-carboxylic Acid Amide (F7)

$^1$H NMR (DMSO-d$_6$/400 MHz) δ ppm 6.35 (bs, 2H), 6.81 (bs, 1H), 6.98-7.11 (m, 5H), 7.15-7.21 (m, 1H), 7.27 (d, J=2.19 Hz, 1H), 7.34 (bs, 1H), 7.40-7.46 (m, 2H), 7.67 (d, J=8.90 Hz, 2H), 8.20 (d, J=5.24 Hz, 1H), 11.62 (bs, 1H); ESI (+) MS: m/z 372 (MH$^+$).

Example 87

5-(2-Amino-pyrimidin-4-yl)-2-biphenyl-4-yl-1H-pyrrole-3-carboxylic Acid Amide (F8)

$^1$H NMR (DMSO-d$_6$/400 MHz) δ ppm 6.35 (bs, 2H), 6.85 (bs, 1H), 6.90-7.15 (m, 5H), 7.15-7.25 (m, 2H), 7.34 (bs, 1H), 7.40-7.45 (m, 2H), 7.70 (d, J=8.90 Hz, 2H), 8.18 (d, J=5.24 Hz, 1H), 11.73 (bs, 1H); ESI (+) MS: m/z 356 (MH$^+$).

Example 88

5-(2-Amino-pyrimidin-4-yl)-2-biphenyl-3-yl-1H-pyrrole-3-carboxylic Acid Amide (F9)

$^1$H NMR (DMSO-d$_6$/400 MHz) δ ppm 6.89 (bs, 2H), 7.02 (d, J=5.24 Hz, 1H), 7.30 (d, J=2.44 Hz, 1H), 7.34-7.43 (m, 2H), 7.46-7.53 (m, 4H), 7.61-7.68 (m, 2H), 7.74 (d, J=8.41 Hz, 2H), 7.96 (t, J=1.70 Hz, 1H), 8.21 (d, J=5.24 Hz, 1H), 11.78 (bs, 1H); ESI (+) MS: m/z 356 (MH$^+$).

Example 89

5-(2-Amino-pyrimidin-4-yl)-2-biphenyl-2-yl-1H-pyrrole-3-carboxylic Acid Amide (F10)

$^1$H NMR (DMSO-d$_6$/400 MHz) δ ppm 6.33 (bs, 2H), 6.90 (bs, 1H), 7.03 (d, J=5.24 Hz, 1H), 7.28 (d, J=2.44 Hz, 1H), 7.34-7.56 (m, 6H), 7.56-7.79 (m, 4H), 8.20 (d, J=5.24 Hz, 1H), 11.78 (bs, 1H); ESI (+) MS: m/z 356 (MH$^+$).

Example 90

5-(2-Amino-pyrimidin-4-yl)-2-(2-methoxy-phenyl)-1H-pyrrole-3-carboxylic Acid Amide (F11)

$^1$H NMR (DMSO-d$_6$/400 MHz) δ ppm 3.75 (s, 3H), 6.34 (bs, 2H), 6.69 (bs, 1H), 6.88-7.04 (m, 3H), 7.08 (d, J=6.10 Hz, 1H), 7.23 (d, J=2.56 Hz, 1H), 7.32-7.41 (m, 2H), 8.16 (d, J=5.37 Hz, 1H), 11.50 (bs, 1H); ESI (+) MS: m/z 310 (MH$^+$).

Example 91

5-(2-Amino-pyrimidin-4-yl)-2-benzo[1,3]dioxol-5-yl-1H-pyrrole-3-carboxylic Acid Amide (F12)

$^1$H NMR (DMSO-d$_6$/400 MHz) δ ppm 6.06 (s, 2H), 6.35 (bs, 2H), 6.82 (bs, 1H), 6.97 (bs, 1H), 7.01 (d, J=5.24 Hz, 1H), 7.16 (dd, J=8.05, 1.34 Hz, 1H), 7.23-7.25 (m, 3H), 8.20 (d, J=5.24 Hz, 1H), 11.52 (bs, 1H); ESI (+) MS: m/z 324 (MH$^+$).

Example 92

5-(2-Amino-pyrimidin-4-yl)-2-(5-chloro-thiophen-2-yl)-1H-pyrrole-3-carboxylic Acid Amide (G4)

$^1$H NMR (DMSO-d$_6$/400 MHz) δ ppm 6.40 (bs, 2H), 6.98 (bs, 1H), 7.03 (d, J=5.24 Hz, 1H), 7.11 (d, J=3.20 Hz, 1H), 7.32 (s, 1H), 7.59 (bs, 1H), 7.63 (d, J=3.20 Hz, 1H), 8.23 (d, J=5.24 Hz, 1H), 11.70 (bs, 1H); ESI (+) MS: m/z 320 (MH$^+$).

Example 93

5-(2-Amino-pyrimidin-4-yl)-2-benzo[b]thiophen-2-yl-1H-pyrrole-3-carboxylic Acid Amide (G5)

$^1$H NMR (DMSO-d$_6$/400 MHz) δ ppm 6.42 (bs, 2H), 6.99 (bs, 1H), 7.08 (d, J=5.12 Hz, 1H), 7.32 (s, 1H), 7.33-7.41 (m, 2H), 7.56 (bs, 1H), 7.84 (bs, 1H), 7.91-8.03 (m, 2H), 8.25 (d, J=5.12 Hz, 1H), 11.82 (bs, 1H); ESI (+) MS: m/z 336 (MH$^+$).

Example 94

5-(2-Amino-pyrimidin-4-yl)-2-benzo[b]thiophen-3-yl-1H-pyrrole-3-carboxylic Acid Amide (G6)

$^1$H NMR (DMSO-d$_6$/400 MHz) δ ppm 6.35 (bs, 2H), 6.76 (bs, 1H), 6.99 (d, J=5.24 Hz, 1H), 7.20 (s, 1H), 7.35-7.42 (m, 3H), 7.51-7.57 (m, 1H), 7.90 (s, 1H), 8.00-8.06 (m, 1H), 8.20 (d, J=5.24 Hz, 1H), 11.91 (bs, 1H); ESI (+) MS: m/z 336 (MH$^+$).

Example 95

5-(2-Amino-pyrimidin-4-yl)-2-benzofuran-2-yl-1H-pyrrole-3-carboxylic Acid Amide (G9)

$^1$H NMR (DMSO-d$_6$/400 MHz) δ ppm 6.53 (bs, 2H), 7.07 (bs, 1H), 7.11 (d, J=5.12 Hz, 1H), 7.27 (td, J=7.56, 0.98 Hz, 1H), 7.34 (td, J=7.56, 0.98 Hz, 1H), 7.42 (s, 1H), 7.61 (dd, J=7.56, 0.98 Hz, 1H), 7.65 (bs, 1H), 7.70 (dd, J=7.56, 0.98 Hz, 1H), 7.87 (d, J=0.98 Hz, 1H), 8.26 (d, J=5.12 Hz, 1H), 11.61 (bs, 1H); ESI (+) MS: m/z 320 (MH$^+$).

Example 96

5-(2-Amino-pyrimidin-4-yl)-2-dibenzofuran-1-yl-1H-pyrrole-3-carboxylic Acid Amide (G10)

$^1$H NMR (DMSO-d$_6$/400 MHz) δ ppm 6.52 (bs, 2H), 6.82 (bs, 1H), 7.03 (d, J=5.38 Hz, 1H), 7.36 (bs, 1H), 7.38-7.56 (m, 3H), 7.64-7.73 (m, 2H), 8.16 (dd, J=7.68, 1.22 Hz, 1H), 8.19 (d, J=7.68 Hz, 1H), 8.24 (d, J=5.38 Hz, 1H), 12.00 (bs, 1H); ESI (+) MS: m/z 370 (MH$^+$).

Example 97

5-(2-Amino-pyrimidin-4-yl)-2-pyridin-3-yl-1H-pyrrole-3-carboxylic Acid Amide (G11)

$^1$H NMR (DMSO-d$_6$/400 MHz) δ ppm 6.63 (bs, 2H), 7.23 (d, J=5.24 Hz, 1H), 7.15 (bs, 1H), 7.32-7.38 (m, 1H), 7.66 (s, 1H), 7.85-7.91 (m, 1H), 8.20 (d, J=5.24 Hz, 1H), 8.28 (bs, 1H), 8.60-8.66 (m, 1H), 8.77-8.86 (m, 1H), 11.37 (s, 1H); ESI (+) MS: m/z 281 (MH+).

Example 98

5-(2-Amino-pyrimidin-4-yl)-2-pyridin-2-yl-1H-pyrrole-3-carboxylic Acid Amide (G12)

$^{1}$H NMR (DMSO-d$_{6}$/400 MHz) δ ppm 6.62 (bs, 2H), 7.03 (d, J=5.12 Hz, 1H), 7.16 (bs, 1H), 7.33-7.40 (m, 2H) 7.86-7.93 (m, 1H), 8.25 (d, J=5.12 Hz, 1H), 8.28 (bs, 1H), 8.43 (d, J=8.17 Hz, 1H), 8.62-8.67 (m, 1H), 11.29 (s, 1H); ESI (+) MS: m/z 281 (MH+).

Example 99

5-(3-Fluoro-pyridin-4-yl)-2-o-tolyl-1H-pyrrole-3-carboxylic Acid Amide (E2)

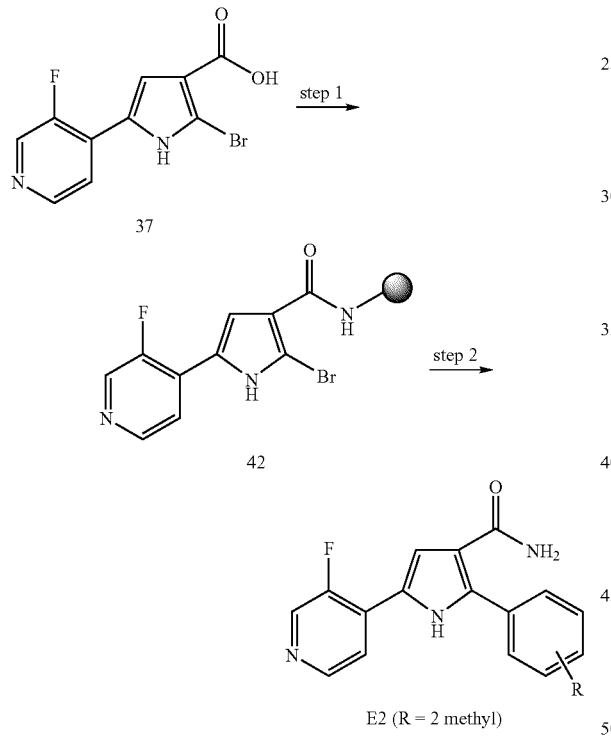

Step 1: Condensation to Amide (42)

Acid 37 (50 mg, 0.175 mmol) was loaded on Rink Amide MBHA resin (128 mg, 0.087 mmol, theoretical loading 0.68 mmol/g) using DIEA (61 μL, 0.35 mmol), EDCI (50 mg, 0.26 mmol), HOBT (35 mg, 0.26 mmol) in 2.5 mL of DMF. The reaction mixture was stirred overnight at rt. The resin had been first cleaved with 20% piperidine in DMF.

Step 2: Suzuki Coupling and Cleavage to Amides (E2)

Supported amide 42 (0.087 mmol), 2-methylphenylboronic acid (60 mg, 0.44 mmol), LiCl (15 mg, 0.35 mmol), Cs$_{2}$CO$_{3}$ (142 mg, 0.435 mmol) and (PhP$_{3}$)$_{2}$PdCl$_{2}$ (12 mg, 0.0175 mmol) in 1.5 mL of DMF and 75 μL of H$_{2}$O were heated at 100° C. overnight. The product supported on the resin was cleaved with TFA/DCM 95:5. The solution was concentrated and the crude material was purified by preparative HPLC to afford 5-(3-fluoro-pyridin-4-yl)-2-o-tolyl-1H-pyrrole-3-carboxylic acid amide as a white solid.

$^{1}$H NMR (DMSO-d$_{6}$/400 MHz) δ ppm 2.16 (s, 3H), 6.86 (bs, 2H), 7.23 (bs, 1H), 7.18-7.38 (m, 4H), 7.91-7.98 (m, 1H), 8.39 (d, J=5.12 Hz, 1H), 8.56 (d, J=3.41 Hz, 1H), 11.95 (bs, 1H); ESI (+) MS: m/z 296 (MH+).

Example 100

5-Pyridin-4-yl-1H-pyrrole-3-carboxylic Acid Amide (P1)

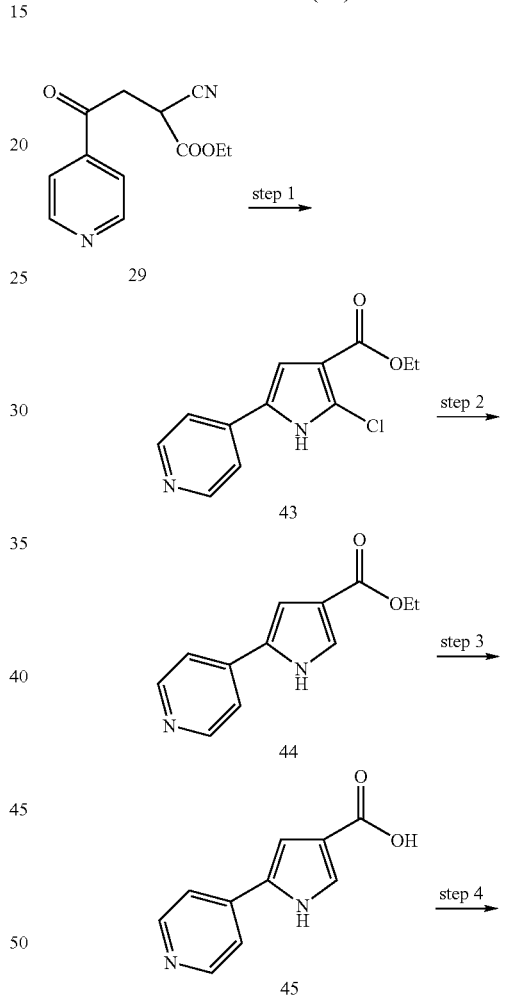

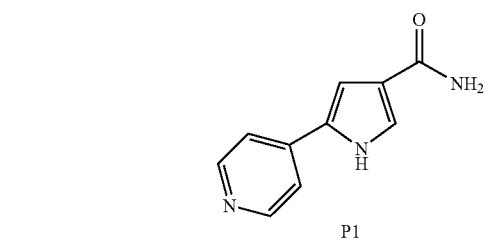

Step 1: Formation of Pyrrole Ring (43)

To a solution of cianoester 29 (550 mg, 2.37 mmol) in Et$_{2}$O (1 mL) at 0° C., 4N HCl in dioxane (6 mL, 23.7 mmol) was added dropwise. The reaction mixture was left for 10 min at 0° C. and then stirring was continued at rt for 6 h. The solid was filtered and washed with Et$_2$O to yield 500 mg (84%) of 2-chloro-5-pyridin-4-yl-1H-pyrrole-3-carboxylic acid ethyl ester as a yellow solid. The product was used without further purification.

$^1$H NMR (DMSO-d$_6$/400 MHz) δ ppm 1.34 (t, J=7.07 Hz, 3H), 4.27 (q, J=7.07 Hz, 2H), 7.73 (s, 1H), 8.25 (d, J=5.61 Hz, 2H), 8.78 (m, 2H); ESI (+) MS: m/z 251 (MH$^+$).

Step 2: Dehalogenation to Ester (44)

A mixture of ester 43 (630 mg, 2.2 mmol) in 30 mL of MeOH, HCOONH$_4$ (1.26 g, 19.8 mmol) and 10% Pd/C (630 mg) was stirred at rt under argon until disappearance of the starting material. The catalyst was removed by filtration through celite and the filtrate concentrated. Saturated aq NaHCO$_3$ was added and the slurry was extracted with EtOAc affording 300 mg (63%) of 5-pyridin-4-yl-1H-pyrrole-3-carboxylic acid ethyl ester as a solid.

$^1$H NMR (DMSO-d$_6$/400 MHz) δ ppm 1.30 (t, J=7.07 Hz, 3H), 4.24 (q, J=7.07 Hz, 2H), 7.20 (m, 1H), 7.63 (m, 1H), 7.68 (dd, J=1.50, 4.60 Hz, 2H), 7.20 (m, 1H), 7.63 (m, 1H), 7.68 (dd, J=1.50, 4.60 Hz, 2H), 8.52 (dd, J=1.50, 4.60 Hz, 2H), 12.27 (s, 1H); ESI (+) MS: m/z 217 (MH$^+$).

Step 3: Saponification to Acid (45)

Ester 44 (200 mg, 0.92 mol) in 4M aq NaOH (4.6 mL) and EtOH (4 mL) was heated at 100° C. for 1 h. The reaction mixture was cooled to 0° C. and the product was precipitated by adding conc HCl. The solid was filtered to obtain 160 mg (78%) of 5-pyridin-4-yl-1H-pyrrole-3-carboxylic acid as a white solid.

$^1$H NMR (DMSO-d$_6$/400 MHz) δ ppm 7.60 (s, 1H), 7.81 (m, 1H), 8.14 (d, J=5.49 Hz, 2H), 8.72 (m, 2H), 12.70 (s, 1H); MS: m/z 187 [M-H].

Step 4: Condensation to Amide (P1)

To a solution of acid 45 (137 mg, 0.61 mmol) in DIEA (213 µL, 1.22 mmol) and anhydrous THF (8 mL), cooled at 0° C., EDCI (175 mg, 0.09 mmol) and HOBT-NH$_3$ (137 mg, 0.9 mmol) were added and the solution was stirred overnight at rt. The solution was concentrated, water was added and the product was extracted with DCM. The organic layer was washed with water, dried and concentrated to give a solid that was triturated with Et$_2$O to afford 50 mg (44%) of 5-pyridin-4-yl-1H-pyrrole-3-carboxylic Acid Amide.

$^1$H NMR (DMSO-d$_6$/400 MHz) δ ppm 6.98 (bs, 2H) 7.61 (bs, 1H) 7.79-7.82 (m, 1H) 8.06 (d, J=6.58 Hz, 2H) 8.71 (d, J=6.83 Hz, 2H) 12.57 (s, 1H); ESI (+) MS: m/z 188 (MH$^+$).

Example 101

1-Ethyl-2-phenyl-5-pyridin-4-yl-1H-pyrrole-3-carboxylic Acid Amide (D1)

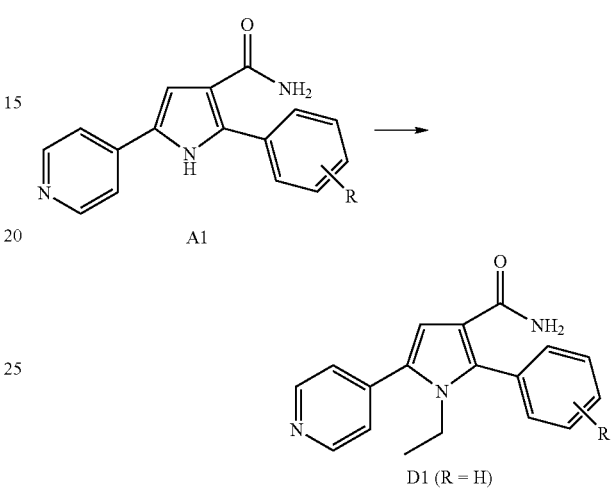

To a solution of amide A1 (R=H, 31 mg, 0.118 mmol) in DMF (0.5 mL), Cs$_2$CO$_3$ (100 mg, 0.235 mmol) and EtI (19 µL, 0.235 mmol) were added. The mixture was treated with microwaves at 60° C. for 15 min ("cooling while heating" technique) then the solvent was removed. To the residue EtOAc and water were added, the layers were separated, the aqueous layer was extracted with EtOAc and the combined organic layers were washed with water, dried (Na$_2$SO$_4$), filtered and concentrated. The crude material was purified by flash chromatography (DCM/MeOH 95:5), affording the title compound. This was suspended in MeOH and acidified to pH 1 with 1.25M HCl in MeOH. After solvent removal the residue was treated with Et$_2$O, the resulting solid was filtered, washed with Et$_2$O and dried, affording the hydrochloric salt of 1-ethyl-2-phenyl-5-pyridin-4-yl-1H-pyrrole-3-carboxylic acid amide (9 mg, 26% yield).

$^1$H NMR (DMSO-d$_6$/400 MHz) δ ppm 0.88 (t, J=7.13 Hz, 3H) 4.02 (q, J=7.11 Hz, 2H) 6.86 (s, 2H) 7.29 (s, 1H) 7.39-7.58 (m, 5H) 7.95 (d, J=6.58 Hz, 2H) 8.80 (d, J=6.71 Hz, 2H); ESI (+) MS: m/z 292 (MH$^+$).

Example 102

4-Methyl-2-phenyl-5-pyridin-4-yl-1H-pyrrole-3-carboxylic Acid Amide (B1)

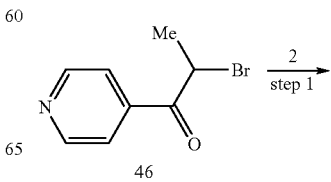

46

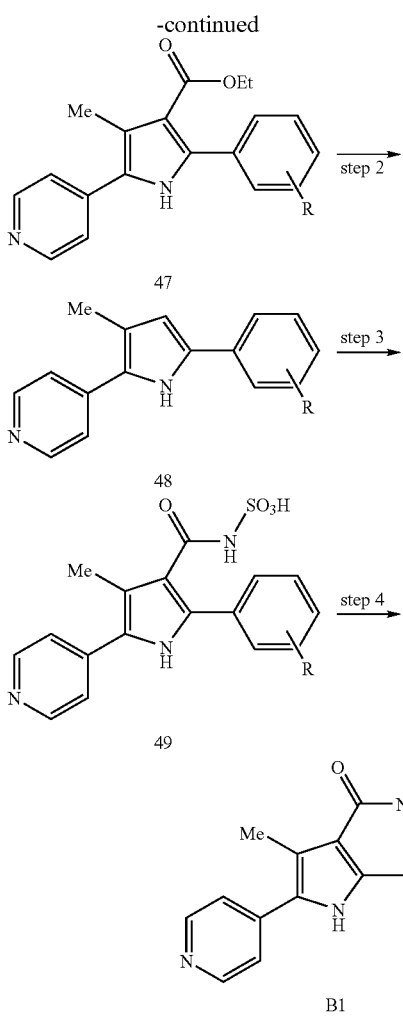

(R = H)

Step 1: Formation of Pyrrole Ring (47)

2-Bromo-1-pyridin-4-yl-propan-1-one hydrobromide 46 (0.6 g, 2 mmol) was added to a mixture of 3-oxo-3-phenyl-propionic acid ethyl ester 2 (R=H, 0.3 g, 1.56 mmol) in 300 mL of dry THF and NaH (0.18 g) at 0° C. The solution was left at 0° C. for 1 h and then stirred at 50° C. for 4 h. The solvent was removed and the residue was dissolved in 20 mL of EtOH, ammonium acetate (0.7 g, 9.3 mmol) was added and the reaction mixture was left overnight at rt. The reaction mixture was concentrated, water was added and the slurry extracted with EtOAc. The combined organic layers were washed with water, dried ($Na_2SO_4$), filtered and concentrated. The crude was purified by flash chromatography (DCM/MeOH 95:5) affording 170 mg (36%) of 4-methyl-2-phenyl-5-pyridin-4-yl-1H-pyrrole-3-carboxylic acid ethyl ester as a solid.

$^1$H NMR (DMSO-$d_6$/300 MHz) δ ppm 1.08 (t, J=7.03 Hz, 3H) 2.41 (s, 3H) 4.08 (q, J=7.03 Hz, 2H) 7.21-7.71 (m, 7H) 8.58 (dd, J=4.69, 1.76 Hz, 2H) 11.77 (s, 1H); ESI (+) MS: m/z 307 (MH$^+$).

Step 2: Decarboxylation to Pyrrole (48)

Ester 47 (0.17 g, 0.56 mmol), dissolved in 1.5 mL of EtOH and 2.2 mL of 4M aq NaOH, was heated at 100° C. until decarboxylation was complete (5 h). The reaction mixture was concentrated, water was added and the slurry extracted with EtOAc. The combined organic layers were washed with water, dried ($Na_2SO_4$), filtered and concentrated to yield 4-(3-methyl-5-phenyl-1H-pyrrol-2-yl)-pyridine as a white solid (92 mg, 70%).

$^1$H NMR (DMSO-$d_6$/400 MHz) δ ppm 2.30 (s, 3H) 6.52-6.54 (m, 1H) 7.18-7.26 (m, 1H) 7.35-7.43 (m, 2H) 7.58 (dd, J=4.69, 1.76 Hz, 2H) 7.73-7.79 (m, 2H) 8.53 (dd, J=4.69, 1.47 Hz, 2H) 11.21 (s, 1H); ESI (+) MS: m/z 235 (MH$^+$).

Step 3: Formation of Sulfamic Acid (49)

To pyrrole 48 (90 mg, 0.39 mmol), dissolved in $CH_3CN$ (3 mL), $ClSO_2NCO$ was added and the reaction mixture was stirred at rt until disappearance of starting material. Water was added and pH was adjusted to 8 with 10% aq KOH. After extraction with EtOAc (x 2) and concentration under reduced pressure of the aqueous solution, the precipitate was filtered, washed with little water and dried. Obtained (4-methyl-2-phenyl-5-pyridin-4-yl-1H-pyrrole-3-carbonyl)-sulfamic acid as a white solid (90% yield).

$^1$H NMR (DMSO-$d_6$/400 MHz) δ ppm 2.27 (s, 3H) 7.22-7.34 (m, 1H) 7.34-7.45 (m, 2H) 7.55 (dd, J=4.76, 1.59 Hz, 2H) 7.62-7.66 (m, 2H) 8.54 (dd, J=4.63, 1.46 Hz, 2H) 9.28 (s, 1H) 11.29 (s, 1H); MS: m/z 356 [M-H].

Step 4: Formation of Amides (B1)

Acid 49 was hydrolized by dissolution in conc. HCl at rt. The acidic aqueous solution was basified with 2N NaOH and extracted with EtOAc (x3). The crude product was purified by flash chromatography (DCM/MeOH 95:5, then 93:7) affording 4-methyl-2-phenyl-5-pyridin-4-yl-1H-pyrrole-3-carboxylic acid amide in 85% yield.

$^1$H NMR (DMSO-$d_6$/500 MHz) δ ppm 2.41 (s, 3H) 7.39 (t, J=7.48 Hz, 1H) 7.47 (t, J=7.48 Hz, 2H) 7.71 (d, J=7.32 Hz, 2H) 8.16 (d, J=7.02 Hz, 2H) 8.73 (d, J=7.02 Hz, 2H); ESI (+) MS: m/z 278 (MH$^+$).

Example 103

2-[4-(4-Methyl-piperazin-1-yl)-phenyl]-5-pyridin-4-yl-1H-pyrrole-3-carboxylic Acid Ethyl Ester (51)

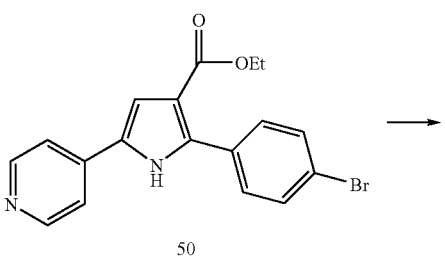

50

-continued

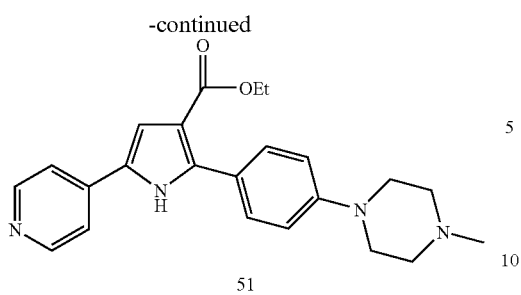

51

A mixture of ester 50 (30 mg, 0.08 mmol, obtained as described in Example 1), Pd(OAc)₂ (1 mg, 0.0045 mmol), (2-biphenylyl)dicyclohexylphosphine (3 mg, 0.008 mmol), $^t$BuONa (16 mg, 0.17 mmol), 1-methylpiperazine (60 μL, 0.54 mmol), in toluene (1 mL) and anhydrous DMF (0.2 mL) was subdued to the action of microwaves at 130° C. for 20 min. After filtration on celite and aqueous work-up (EtOAc/water) the crude 2-[4-(4-methyl-piperazin-1-yl)-phenyl]-5-pyridin-4-yl-1H-pyrrole-3-carboxylic acid ethyl ester was obtained.

$^1$H NMR (DMSO-$d_6$/400 MHz) δ ppm 1.25 (t, J=7.07 Hz, 3H), 2.86 (bs, 3H), 3.11-3.54 (m, 8H), 4.20 (q, J=7.07 Hz, 2H), 7.12 (d, J=8.80 Hz, 2H), 7.64 (d, J=8.80 Hz, 2H), 7.78-7.82 (m, 1H), 8.34-8.41 (m, 2H), 8.75 (d, J=6.46 Hz, 2H), 12.49 (bs, 1H); ESI (+) MS: m/z 391 (MH⁺).

Employing the above procedure and starting from the corresponding bromophenyl ester derivatives, obtained described in Example 1, the following compounds have been prepared:

2-(3-Morpholin-4-yl-phenyl)-5-pyridin-4-yl-1H-pyrrole-3-carboxylic Acid Ethyl Ester (52)

$^1$H NMR (DMSO-$d_6$/400 MHz) δ ppm 1.19 (t, J=7.07 Hz, 3H) 3.14-3.20 (m, 4H) 3.73-3.79 (m, 4H) 4.13 (q, J=7.07 Hz, 2H) 7.01 (dd, J=8.17, 2.19 Hz, 1H) 7.08 (d, J=7.68 Hz, 1H) 7.18 (t, J=1.70 Hz, 1H) 7.26 (d, J=2.80 Hz, 1H) 7.31 (t, J=7.93 Hz, 1H) 7.77 (dd, J=4.69, 1.52 Hz, 2H) 8.51 (d, J=5.85 Hz, 2H) 12.03 (bs, 1H); ESI (+) MS: m/z 306 (MH⁺).

2-(4-Morpholin-4-yl-phenyl)-5-pyridin-4-yl-1H-pyrrole-3-carboxylic Acid Ethyl Ester (53)

ESI (+) MS: m/z 306 (MH⁺).

Using the procedure already described in Example 1 the above esters were respectively hydrolyzed to the following acids:

2-[4-(4-Methyl-piperazin-1-yl)-phenyl]-5-pyridin-4-yl-1H-pyrrole-3-carboxylic Acid (54)

$^1$H NMR (DMSO-$d_6$/400 MHz) δ ppm 2.83 (bs, 3H), 3.09-3.53 (m, 8H), 7.10 (d, J=8.80 Hz, 2H), 7.63 (d, J=8.80 Hz, 2H), 7.92 (s, 1H), 8.05-8.21 (m, 2H), 8.58-8.69 (m, 2H), 12.23 (bs, 1H); ESI (+) MS: m/z 361 [M-H].

2-(3-Morpholin-4-yl-phenyl)-5-pyridin-4-yl-1H-pyrrole-3-carboxylic Acid (55)

$^1$H NMR (DMSO-$d_6$/400 MHz) δ ppm 3.13-3.17 (m, 4H) 3.73-3.78 (m, 4H) 6.90 (dt, J=7.19, 2.13 Hz, 1H) 7.10 (s, 1H) 7.22 (s, 1H) 7.24 (s, 1H) 7.43 (s, 1H) 7.71 (dd, J=4.76, 1.59 Hz, 2H) 8.46 (d, J=6.22 Hz, 2H) 11.52 (bs, 1H); MS: m/z 348 [M-H].

2-(4-Morpholin-4-yl-phenyl)-5-pyridin-4-yl-1H-pyrrole-3-carboxylic Acid (56)

MS: m/z 348 [M-H].

By the standard amidation method already described in Example 1, the above acids were respectively transformed into the following amides:

Example 104

2-[4-(4-Methyl-piperazin-1-yl)-phenyl]-5-pyridin-4-yl-1H-pyrrole-3-carboxylic Acid Amide (A24)

$^1$H NMR (DMSO-$d_6$/400 MHz) δ ppm 2.82 (bs, 3H), 3.15-3.52 (m, 8H), 7.08 (d, J=8.80 Hz, 2H), 7.67 (d, J=8.80 Hz, 2H), 7.94 (s, 1H), 7.97-8.11 (m, 2H), 8.56-8.72 (m, 2H), 12.04 (bs, 1H); ESI (+) MS: m/z 362 (MH⁺).

Example 105

2-(3-Morpholin-4-yl-phenyl)-5-pyridin-4-yl-1H-pyrrole-3-carboxylic Acid Amide Hydrochloride (A25)

$^1$H NMR (DMSO-$d_6$/400 MHz) δ ppm 3.14-3.21 (m, 4H) 3.74-3.79 (m, 4H) 7.04 (dd, J=8.23, 2.13 Hz, 1H) 7.15 (d, J=7.68 Hz, 1H) 7.31 (s, 1H) 7.33 (t, J=7.93 Hz, 1H) 7.71 (d, J=2.56 Hz, 1H) 8.23 (d, J=6.71 Hz, 2H) 8.73 (d, J=6.95 Hz, 2H) 12.34 (bs, 1H) 15.08 (bs, 1H); ESI (+) MS: m/z 349 (MH⁺).

Example 106

2-(4-Morpholin-4-yl-phenyl)-5-pyridin-4-yl-1H-pyrrole-3-carboxylic Acid Amide (A26)

$^1$H NMR (DMSO-$d_6$/400 MHz) δ ppm 3.15-3.20 (m, 4H), 3.73-3.79 (m, 4H), 6.82 (bs, 1H), 6.99 (d, J=8.80 Hz, 2H), 7.08 (bs, 1H), 7.23 (d, J=2.68 Hz, 1H), 7.56 (d, J=8.80 Hz, 2H), 7.68 (d, J=6.35 Hz, 2H), 8.49 (d, J=6.35 Hz, 2H), 11.63 (bs, 1H); ESI (+) MS: m/z 349 (MH⁺).

Example 107

5-(2-Amino-pyrimidin-4-yl)-2-phenyl-1H-pyrrole-3-carboxylic Acid Methylamide (M1)

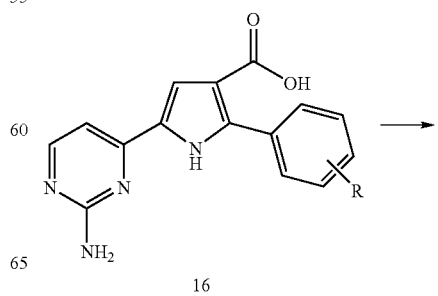

16

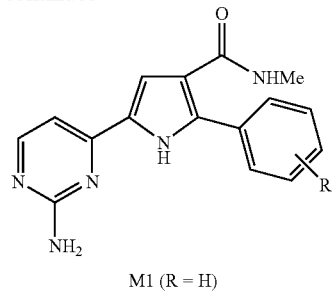

M1 (R = H)

To a solution of acid 16 (R=H, 20 mg, 0.07 mmol) in anhydrous DMF, CDI (25 mg, 2 eq.) was added and the mixture stirred at 45° C. for 1 h. After cooling to rt the solution was treated with 0.5 mL of 33% MeNH$_2$ in EtOH. The mixture was stirred overnight, filtered and the filtrate was poured into water. After extraction with EtOAc (×2) the organic layer was concentrated, dissolved in EtOH and treated with excess 1.25M HCl in MeOH. Et$_2$O was added and the yellow crystalline solid was filtered, washed with Et$_2$O and recovered. Obtained 8 mg (37% yield) of 5-(2-amino-pyrimidin-4-yl)-2-phenyl-1H-pyrrole-3-carboxylic acid methylamide.

$^1$H NMR (DMSO-d$_6$/400 MHz) δ ppm 2.70 (d, J=4.63 Hz, 3H) 7.36 (d, J=6.58 Hz, 1H) 7.39-7.49 (m, 3H) 7.53 (d, J=2.44 Hz, 1H) 7.64-7.70 (m, 2H) 7.84 (bs, 3H) 8.02 (bq, J=4.51 Hz, 1H) 8.29 (d, J=6.46 Hz, 1H) 12.20 (bs, 1H); ESI (+) MS: m/z 294 (MH$^+$).

The above procedure was employed to synthesize the following compounds.

Example 108

5-(2-Amino-pyrimidin-4-yl)-2-phenyl-1H-pyrrole-3-carboxylic Acid Isopropylamide (M2)

$^1$H NMR (DMSO-d$_6$/400 MHz) δ ppm 1.09 (t, J=6.58 Hz, 6H), 3.93-4.06 (m, 1H), 6.36 (bs, 2H), 7.04 (d, J=5.24 Hz, 1H), 7.23 (d, J=2.44 Hz, 1H), 7.30-7.43 (m, 3H), 7.59-7.67 (m, 3H), 8.21 (d, J=5.24 Hz, 1H), 11.61 (bs, 1H); ESI (+) MS: m/z 322 (MH$^+$).

Example 109

5-(2-Amino-pyrimidin-4-yl)-2-phenyl-1H-pyrrole-3-carboxylic Acid Benzylamide (M3)

$^1$H NMR (DMSO-d$_6$/400 MHz) δ ppm 4.37 (d, J=6.10 Hz, 2H), 6.37 (bs, 2H), 7.05 (d, J=5.24 Hz, 1H), 7.18-7.44 (m, 9H), 7.64 (d, J=8.30 Hz, 2H), 8.21 (d, J=5.24 Hz, 1H), 8.48 (t, J=6.10 Hz, 1H), 11.70 (bs, 1H); ESI (+) MS: m/z 370 (MH$^+$).

Example 110

5-(2-Amino-pyrimidin-4-yl)-2-phenyl-1H-pyrrole-3-carboxylic Acid cyclohexylmethyl-amide (M4)

$^1$H NMR (DMSO-d$_6$/400 MHz) δ ppm 0.79-0.94 (m, 2H), 1.06-1.27 (m, 4H), 1.40-4.52 (m, 1H), 1.57-1.74 (m, 4H), 2.99 (t, J=6.46 Hz, 2H), 6.36 (bs, 2H), 7.04 (d, J=5.24 Hz, 1H), 7.23 (d, J=2.44 Hz, 1H), 7.29-7.46 (m, 3H), 7.63 (d, J=8.15 Hz, 2H), 7.82 (t, J=5.85 Hz, 1H), 8.21 (d, J=5.24 Hz, 1H), 11.63 (bs, 1H); ESI (+) MS: m/z 376 (MH$^+$).

Example 111

5-(2-Amino-pyrimidin-4-yl)-2-phenyl-1H-pyrrole-3-carboxylic Acid phenethyl-amide (M5)

$^1$H NMR (DMSO-d$_6$/400 MHz) δ ppm 2.80 (t, J=7.35 Hz, 2H), 3.42 (q, J=7.35 Hz, 2H), 6.37 (bs, 2H), 7.03 (d, J=5.24 Hz, 1H), 7.18-7.42 (m, 9H), 7.60 (d, J=8.30 Hz, 2H), 7.98 (t, J=7.35 Hz, 1H), 8.21 (d, J=5.24 Hz, 1H), 11.65 (bs, 1H); ESI (+) MS: m/z 384 (MH$^+$).

Example 112

Synthesis of 5-(2-amino-pyrimidin-4-yl)-2-phenyl-thiophene-3-carboxylic Acid Amide (S1)

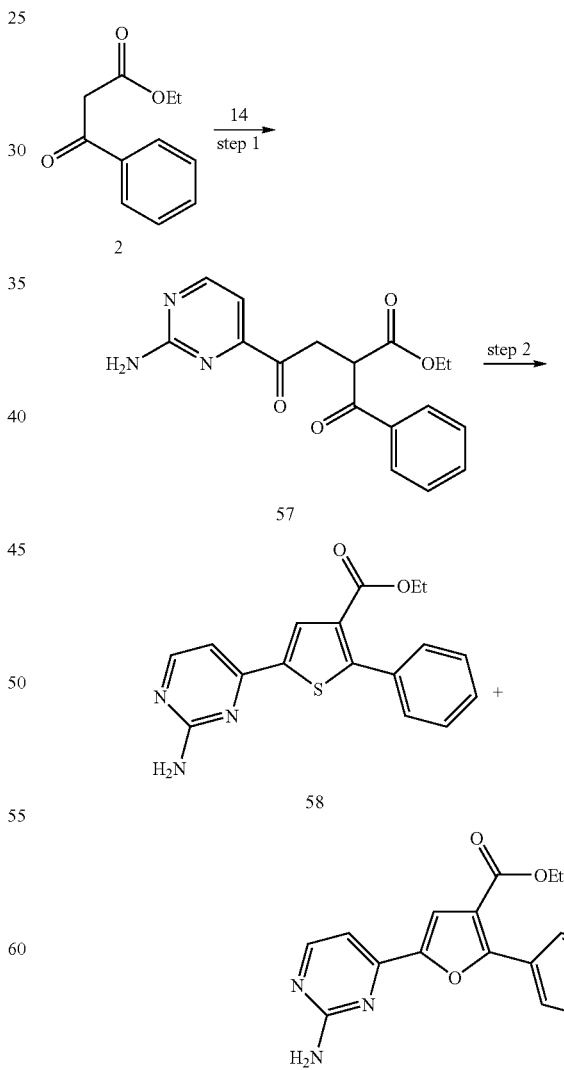

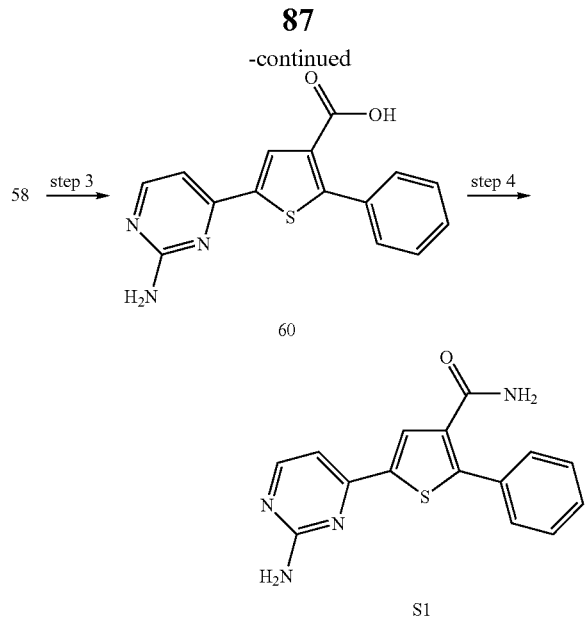

Step 1: Ketoester Alkylation (57)

To a stirred solution of 3-oxo-3-phenyl-propionic acid ethylester 2 (2 g, 10 mmol) and NaH (1 g, 2.5 eq, 25 mmol) in dry THF (200 mL) at 0° C., 1-(2-amino-pyrimidin-4-yl)-2-bromo-ethanone 14 (3.56 g, 1.2 eq, 12 mmol) was added. The reaction mixture was stirred at 0° C. for 30 min, then more 14 (0.5 eq, 1.48 g) was added and the reaction mixture was stirred at rt overnight. After solvent removal, the residue was diluted in DCM and washed with brine, dried (Na$_2$SO$_4$) and the solvent removed under reduced pressure to give 4-(2-amino-pyrimidin-4-yl)-2-benzoyl-4-oxo-butyric acid ethyl ester (3.27 g, 97%). ESI (+) MS: m/z 328 (MH$^+$).

Step 2: Ring Formation (58+59)

A mixture of ester 57 (3.27 g, 10 mmol) and Lawesson's reagent (2.43 g, 0.66 eq, 6 mmol) in toluene (100 mL) were refluxed under N$_2$ for 4 h. After solvent removal, the residue was taken up in DCM, filtered and eluted through the Horizon system (hexane/EtOAc 9:1, then DCM/MeOH 98:2). The mixture of thiophene and furan derivatives was then passed through the Horizon system again (DCM/MeOH 99:1) to give a first fraction of the thiophene derivative 58 (250 mg) and a second fraction of the furan derivative 59 (236 mg) as yellow solids.

5-(2-Amino-pyrimidin-4-yl)-2-phenyl-thiophene-3-carboxylic Acid Ethyl Ester (58)

$^1$H NMR (DMSO-d$_6$/400 MHz) δ ppm: 1.14 (t, 3H), 4.16 (q, 2H), 6.73 (m, 2H), 7.20 (d, 1H), 7.53 (m, 5H), 8.18 (s, 1H), 8.30 (d, 1H); ESI (+) MS: m/z 326 (MH$^+$).

5-(2-Amino-pyrimidin-4-yl)-2-phenyl-furan-3-carboxylic Acid Ethyl Ester (59)

$^1$H NMR (DMSO-d$_6$/400 MHz) δ ppm: 1.29 (t, 3H), 4.27 (q, 2H), 6.76 (m, 2H), 7.07 (d, 1H), 7.52 (m, 3H), 8.03 (m, 2H), 8.34 (d, 1H); ESI (+) MS: m/z 310 (MH$^+$).

Step 3: Saponification to Carboxylic Acid (60)

To a solution of ester 58 (220 mg, 0.68 mmol) in 1:1 H$_2$O/EtOH (9 mL), 4M aq NaOH (10 eq) was added and the mixture stirred at 100° C. for 1 h. After cooling to rt, the solution was acidified with 2M HCl yielding 5-(2-amino-pyrimidin-4-yl)-2-phenyl-thiophene-3-carboxylic acid as a solid which was filtered, washed with water and dried under reduced pressure (185 mg, 90%).

$^1$H NMR (DMSO-d$_6$/400 MHz) δ ppm 7.28 (d, 1H), 7.43-7.58 (m, 5H), 8.25 (s, 1H), 8.31 (d, 1H); ESI (+) MS: m/z 296 [M-H].

Step 4: Condensation to Amide (S1)

To a mixture of acid 60 (185 mg, 0.62 mmol) and DIEA (218 μL, 1.26 mmol, 2 eq) in dry THF (4 mL), EDCI (141.7 mg, 0.93 mmol) and HOBT.NH$_3$ (141.5 mg, 0.93 mmol) were added at 0° C. The reaction mixture was stirred at rt overnight. After solvent evaporation the residue was taken up with DCM and washed with water. The organic layers were dried (Na$_2$SO$_4$), concentrated and the obtained solid was purified by re-precipitation with DCM/hexane to give 5-(2-amino-pyrimidin-4-yl)-2-phenyl-thiophene-3-carboxylic acid amide as a yellow solid (87 mg, 48%).

$^1$H NMR (DMSO-d$_6$/400 MHz) δ ppm: 6.69 (bs, 2H), 7.10 (d, 1H), 7.38-7.44 (m, 5H), 7.56 (d, 2H), 7.71 (bs, 1H), 8.29 (d, 1H); ESI (+) MS: m/z 297 (MH$^+$).

Example 113

Synthesis of 5-(2-amino-pyrimidin-4-yl)-2-phenyl-furan-3-carboxylic Acid Amide (T1)

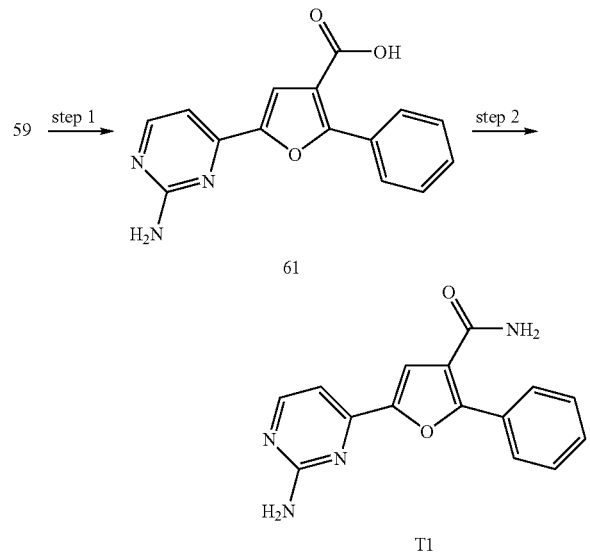

Step 1: Saponification to Carboxylic Acid (61)

To a solution of ester 59 (221 mg, 0.71 mmol) in 1:1 H$_2$O/EtOH (9 mL), 4M aq NaOH (10 eq) was added and the reaction mixture was stirred at 100° C. for 1 h. After cooling to rt, the solution was acidified with 2M HCl yielding 5-(2-amino-pyrimidin-4-yl)-2-phenyl-furan-3-carboxylic acid as a white solid which was filtered, washed with water and dried under reduced pressure (quant.).

$^1$H NMR (DMSO-d$_6$/400 MHz) δ ppm 6.75 (d, 2H), 7.06 (d, 1H), 7.51 (m, 3H), 8.0 (d, 2H), 8.33 (d, 1H); ESI (+) MS: m/z 280 [M-H].

Step 2: Condensation to Amide (T1)

To a mixture of acid 61 (172 mg, 0.61 mmol) and DIEA (213 μL, 1.22 mmol) in dry THF (4 mL), EDCI (139.6 mg, 0.92 mmol) and HOBT.NH$_3$ (140 mg, 0.92 mmol) were added at 0° C. The reaction mixture was stirred at rt overnight. After solvent evaporation the residue was taken up with DCM and washed with water. The aqueous phase was extracted with EtOAc, the organic layer was dried (Na$_2$SO$_4$) and concentrated to give 5-(2-amino-pyrimidin-4-yl)-2-phenyl-furan-3-carboxylic acid amide as a yellow solid (80 mg, 48%).

$^1$H NMR (DMSO-d$_6$/400 MHz) δ ppm: 6.69 (bs, 2H), 7.01 (d, 1H), 7.41-7.48 (m, 4H), 7.53 (s, 1H), 7.92 (bs, 1H), 8.05 (d, 2H), 8.33 (d, 1H); ESI (+) MS: m/z 281 (MH$^+$).

Example 114

5-(2-Amino-5-bromo-pyrimidin-4-yl)-2-phenyl-1H-pyrrole-3-carboxylic Acid Amide (N2)

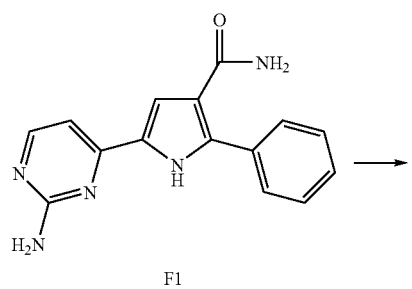

F1

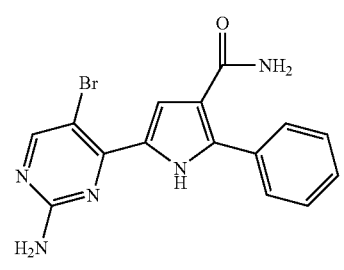

N2

To amide F1 (280 mg, 1 mmol) in DMF (2 mL), NBS (180 mg, 1 mmol) was added and the mixture was stirred at rt for 15 h. The reaction mixture was poured into stirred water, the precipitate was filtered, washed thoroughly and dried. Obtained the title compound as a yellow solid (270 mg, 75%).

$^1$H NMR (DMSO-d$_6$/400 MHz) δ ppm 6.65 (s, 2H) 6.89 (s, 1H) 7.23-7.46 (m, 4H) 7.64-7.68 (m, 2H) 7.64 (d, J=2.68 Hz, 1H) 7.64 (d, J=2.68 Hz, 1H) 8.35 (s, 1H) 11.27 (s, 1H); ESI (+) MS: m/z 358 (MH$^+$).

The above procedure was employed to synthesize, from F4, the following compound:

Example 115

5-(2-Amino-5-bromo-pyrimidin-4-yl)-2-(2-fluoro-phenyl)-1H-pyrrole-3-carboxylic Acid Amide (N8)

$^1$H NMR (DMSO-d$_6$/400 MHz) δ ppm 6.60 (bs, 2H), 6.80 (bs, 1H), 7.18-7.30 (m, 2H), 7.31-7.56 (m, 3H), 7.71 (s, 1H), 8.36 (s, 1H), 11.55 (bs, 1H); ESI (+) MS: m/z 377 (MH$^+$).

The above procedure was employed to synthesize from F1 the following compound, using N-chloro succinimide as the halogenating agent, in DMF at 100° C. for 20 h (72% yield).

Example 116

5-(2-Amino-5-chloro-pyrimidin-4-yl)-2-phenyl-1H-pyrrole-3-carboxylic Acid Amide (N1)

$^1$H NMR (DMSO-d$_6$/400 MHz) δ ppm 6.62 (s, 2H) 6.88 (s, 1H) 7.31-7.46 (m, 4H) 7.58 (d, J=2.68 Hz, 1H) 7.58 (d, J=2.68 Hz, 1H) 7.64-7.69 (m, 2H) 8.27 (s, 1H) 11.27 (s, 1H); ESI (+) MS: m/z 314 (MH$^+$).

The above procedure was employed to synthesize, from F4, the following compound:

Example 117

5-(2-Amino-5-chloro-pyrimidin-4-yl)-2-(2-fluoro-phenyl)-1H-pyrrole-3-carboxylic Acid Amide (N7)

$^1$H NMR (DMSO-d$_6$/400 MHz) δ ppm 6.58 (bs, 2H), 6.81 (bs, 1H), 7.19-7.31 (m, 2H), 7.36-7.59 (m, 3H), 7.67 (s, 1H), 8.29 (s, 1H), 11.60 (bs, 1H); ESI (+) MS: m/z 332 (MH$^+$).

Example 118

5-(2-Amino-pyrimidin-4-yl)-4-iodo-2-phenyl-1H-pyrrole-3-carboxylic Acid Amide (N3)

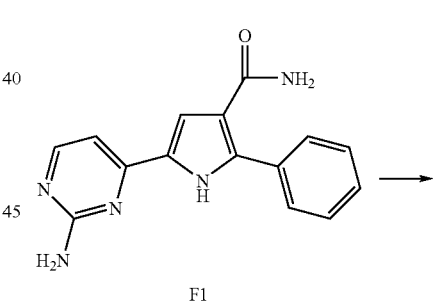

F1

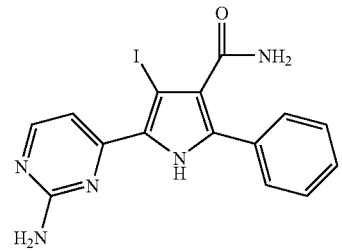

N3

To amide F1 (140 mg, 0.5 mmol) in DMF (1 mL), NIS (110 mg, 0.5 mmol) was added and the mixture was stirred at rt for 4 h. The reaction mixture was poured into stirred water, the precipitate was filtered, washed thoroughly and dried. Obtained the title compound as a greenish solid (145 mg, 72%).

¹H NMR (DMSO-d₆/400 MHz) δ ppm: 6.57 (s, 2H) 7.31-7.37 (m, 2H) 7.39 (s, 1H) 7.40-7.47 (m, 2H) 7.56 (s, 1H) 7.62-7.68 (m, 2H) 8.31 (d, J=5.37 Hz, 1H) 11.74 (s, 1H); ESI (+) MS: m/z 406 (MH⁺).

Example 119

5-(2-Amino-pyrimidin-4-yl)-4-chloro-2-phenyl-1H-pyrrole-3-carboxylic Acid Amide (Z1)

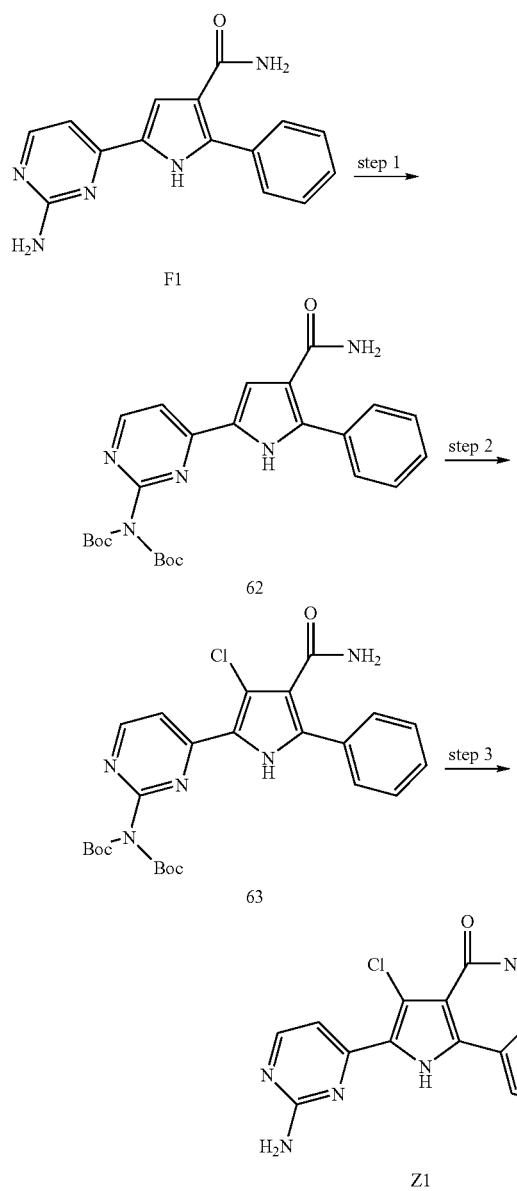

Step 1: Protection of Aminopyrimidine (62)

A solution of amide F1 (850 mg, 3 mmol), (Boc)₂O (1.7 g, 8 mmol) and DMAP (50 mg) in THF (20 mL) and DMF (1 mL) was stirred at room temperature for 48 hours. The mixture as poured into water and the precipitate was filtered. It was dissolved in ethyl acetate, washed with water, dried (Na₂SO₄) and concentrated. The residue, composed by a mixture of mono-, di- and tri-Boc derivatives, was purified by flash chromatography (EtOAc/n-hexane 9:1) affording the di-Boc derivative 62 (14%). ESI (+) MS: m/z 480 (MH⁺).

Step 2: Chlorination of Pyrrole Ring (63)

A solution of amide 62 (165 mg, 0.34 mmol) and N-chlorosuccinimide (46 mg, 0.34 mmol) in DMF (1 mL) was stirred at 100° C. for 2 hours. After cooling the mixture was poured into stirred water, extracted with ethyl acetate, washed with water, dried (Na₂SO₄) and concentrated. The residue was purified by flash chromatography (EtOAc/n-hexane 5:1) affording 63 (80 mg, 45%). ESI (+) MS: m/z 514 (MH⁺).

Step 3: Deprotection of Aminopyrimidine (Z1)

To a solution of 63 (80 mg, 0.156 mmol) in MeOH (1 mL), 4N HCl in dioxane (3 mL) was added and the mixture was stirred at room temperature for 20 hours and then at 50° C. for 1 hour. After concentration diethyl ether was added under stirring and the mixture stirred for 30 minutes. The precipitate was filtered, washed with diethyl ether and dried. Obtained the title compound (45 mg, 82%).

¹H NMR (DMSO-d₆/400 MHz) δ ppm 6.47 (bs, 2H), 7.15 (d, J=5.24 Hz, 1H), 7.35 (t, J=8.50 Hz, 1H), 7.39-7.45 (m, 3H), 7.60 (bs, 1H), 7.64 (d, J=8.54 Hz, 2H), 8.29 (d, J=5.24 Hz, 1H), 11.64 (bs, 1H); ESI (+) MS: m/z 314 (MH⁺).

Example 120

5-(2-Amino-5-bromo-pyrimidin-4-yl)-4-bromo-2-phenyl-1H-pyrrole-3-carboxylic Acid Amide (N4)

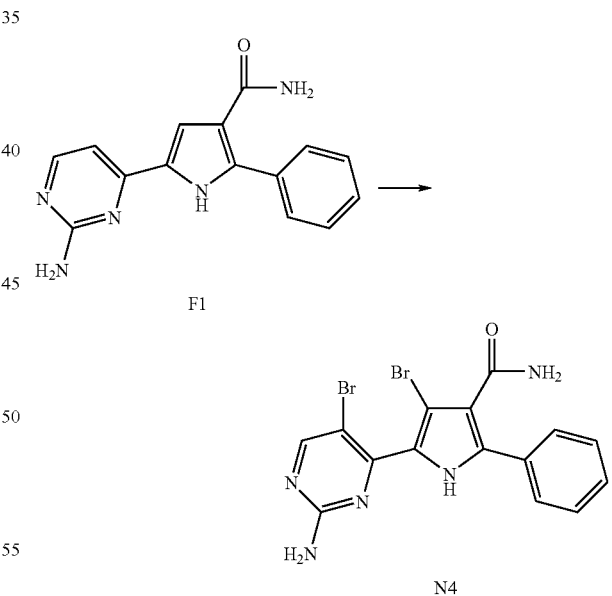

To amide F1 (140 mg, 0.5 mmol) in DMF (1.5 mL), NBS (180 mg, 1 mmol) was added and the mixture was stirred at rt for 15 h. The reaction mixture was poured into stirred water, the precipitate was filtered, washed thoroughly and dried. Obtained the title compound as orange solid (195 mg, 90%).

¹H NMR (DMSO-d₆/400 MHz) δ ppm 6.96 (s, 2H) 7.28-7.34 (m, 1H) 7.35 (s, 1H) 7.38-7.45 (m, 2H) 7.48 (s, 1H) 7.56-7.63 (m, 2H) 8.46 (s, 1H) 12.01 (s, 1H); ESI (+) MS: m/z 438 (MH⁺).

The above procedure was employed to synthesize, from F1, the following compound, using N-iodo succinimide as the halogenating agent.

Example 121

5-(2-Amino-5-iodo-pyrimidin-4-yl)-4-iodo-2-phenyl-1H-pyrrole-3-carboxylic Acid Amide (N5)

$^1$H NMR (DMSO-$d_6$/400 MHz) δ ppm 6.91 (bs, 2H), 7.25-7.33 (m, 1H), 7.35 (bs, 2H), 7.38-7.46 (m, 2H), 7.59 (d, J=8.30 Hz, 2H), 8.57 (s, 1H), 11.96 (s, 1H); ESI (+) MS: m/z 532 (MH$^+$).

Example 122

5-(2-Amino-5-bromo-pyrimidin-4-yl)-4-iodo-2-phenyl-1H-pyrrole-3-carboxylic Acid Amide (N6)

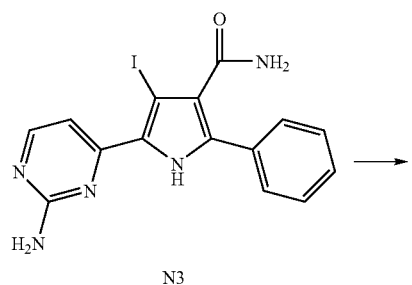

To amide N3 (120 mg, 0.3 mmol) in DMF (1.5 mL), NBS (60 mg, 0.34 mmol) was added and the mixture was stirred at rt for 15 h. The reaction mixture was poured into stirred water, the precipitate was filtered, washed thoroughly and dried. Obtained the title compound as orange solid (83%).

$^1$H NMR (DMSO-$d_6$/400 MHz) δ ppm: 6.95 (s, 2H) 7.24-7.34 (m, 2H) 7.36-7.46 (m, 3H) 7.55-7.61 (m, 2H) 8.45 (s, 1H) 12.01 (s, 1H); ESI (+) MS: m/z 485 (MH$^+$).

Example 123

5-(2-Amino-5-bromo-pyrimidin-4-yl)-4-iodo-2-phenyl-1H-pyrrole-3-carboxylic Acid Amide (N6)

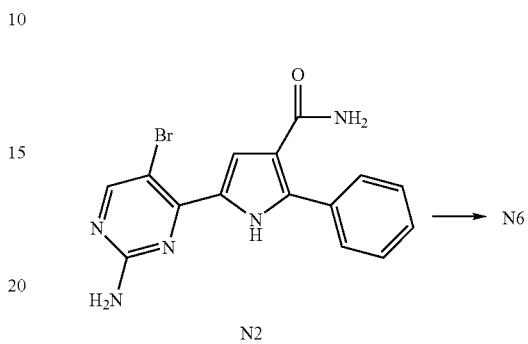

To amide N2 (243 mg, 0.68 mmol) in DMF (1.5 mL), NIS (160 mg, 0.71 mmol) was added and the mixture was stirred at 50° C. for 4 h, then overnight at rt. The reaction mixture was poured into stirred water, the precipitate was filtered, washed thoroughly and dried. The title compound was obtained as orange solid (270 mg, 82%).

Example 124

5-(2-Amino-pyrimidin-4-yl)-2-phenyl-4-vinyl-1H-pyrrole-3-carboxylic Acid Amide (O1)

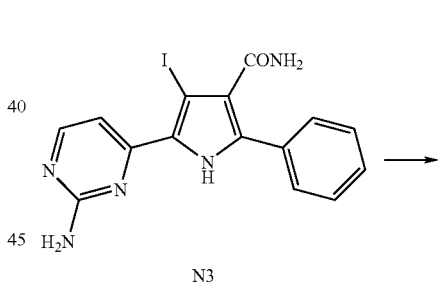

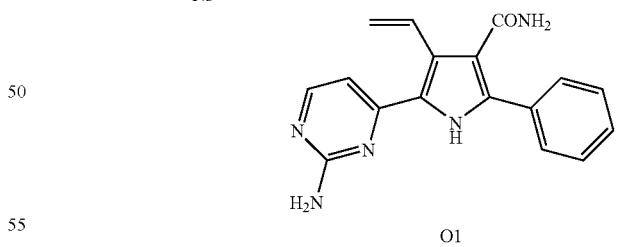

To a stirred solution of N3 (50 mg, 0.125 mmol) in dioxane (5 mL) and DMF (0.5 mL), 2,6-dimethyl-4-ter-butyl phenol (5 mg), palladium tetrakis (5 mg) and tributylvinyl stannane (145 μL) were added. The mixture was warmed at 110° C. for 8 hours, cooled and concentrated. The crude product was purified by flash chromatography (DCM/MeOH 20:1) affording the title compound as a pale yellow solid (24% yield).

$^1$H NMR (DMSO-$d_6$/400 MHz) δ ppm: 5.15 (dd, J=11.58, 2.07 Hz, 1H), 5.64 (dd, J=11.58, 1.95 Hz, 1H), 6.49 (bs, 2H), 6.97 (d, J=5.24 Hz, 1H), 7.28-7.37 (m, 2H), 7.40-7.57 (m, 3H), 7.61-7.71 (m, 3H), 8.23 (d, J=5.24 Hz, 1H), 11.40 (bs, 1H); ESI (+) MS: m/z 306 (MH+).

Example 125

5-(2-Amino-pyridin-4-yl)-2-phenyl-1H-pyrrole-3-carboxylic Acid Amide (U1)

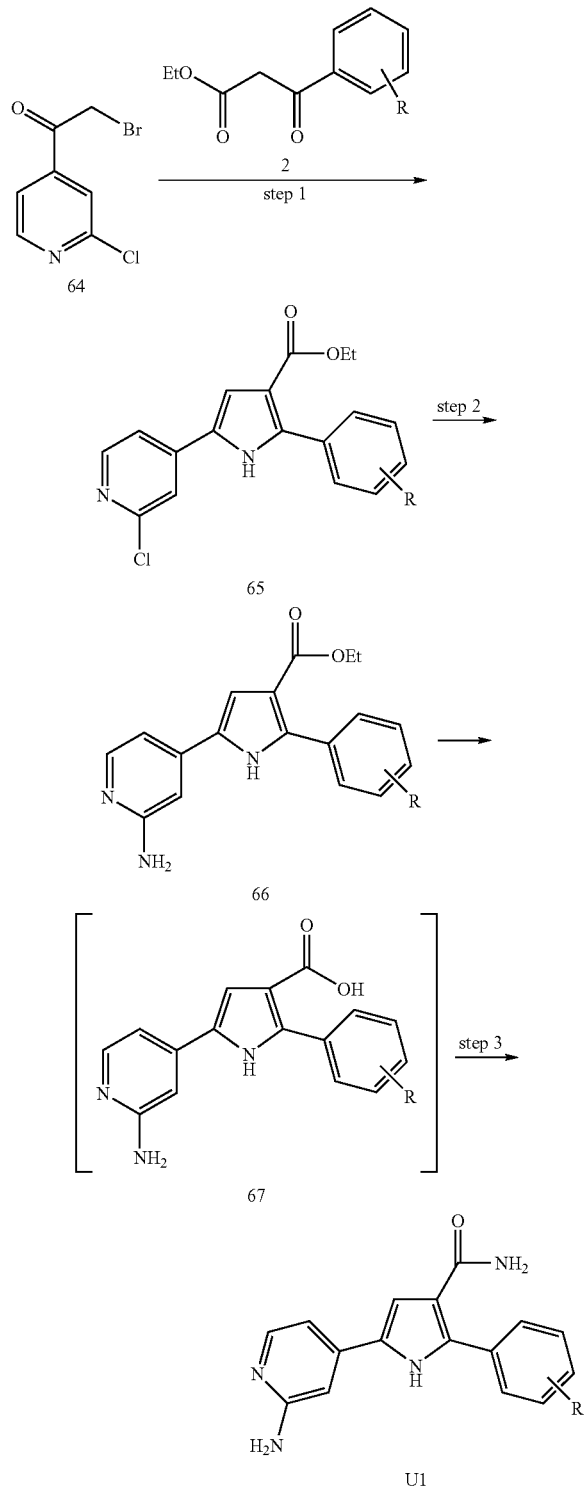

(R = H)

Step 1: Pyrrole Ring Formation (65)

To a solution of ketoester 2 (350 mg, 2 mmol) in THF (45 mL) at 0° C., NaH (180 mg, 4.5 mmol) was added and the mixture was stirred for 20 min at 0° C. Bromoketone hydrochloride 64 (635 mg, 2 mmol) was added and the reaction mixture was stirred at 0° C. for 2 hours, then at room temperature for 2 hours. After solvent removal, absolute ethanol (25 mL) and ammonium acetate (500 mg, 6.5 mmol) were added and the mixture was stirred at room temperature for 20 hours. The solvent was removed and the residue was taken up with ethyl acetate and water. The organic phase was dried and charged for flash chromatography (eluant:DCM/MeOH 95:5). Obtained 5-(2-chloro-pyridin-4-yl)-2-phenyl-1H-pyrrole-3-carboxylic acid ethyl ester (340 mg, 50%).

$^1$H NMR (DMSO-d$_6$/400 MHz) δ ppm: 1.19 (t, J=7.07 Hz, 3H), 4.14 (q, J=7.07 Hz, 2H), 7.38-7.52 (m, 4H), 7.62-7.68 (m, 2H), 7.80 (d, J=5.37, 1H), 7.97 (s, 1H), 8.33 (d, J=5.37 Hz, 1H), 12.37 (bs, 1H); ESI (+) MS: m/z 327 (MH+).

Step 2: Amination of Pyridine Ring (66)

A mixture of ester 65 (120 mg, 0.37 mmol), t-butyl-carbamate (215 mg, 1.84 mmol), Xantphos (16 mg, 0.028 mmol), palladium diacetate (4.1 mg, 0.0183 mmol) and cesium carbonate (240 mg, 0.73 mmol) in dioxane (3 mL) was stirred at 140° C. in a microwave cavity for 20 minutes. The crude material was taken up with methanol, filtered through celite, treated with ethylacetate and water, dried and concentrated. The residue was purified by flash chromatography (eluant:DCM/EtOAc 95:5). Obtained 5-(2-amino-pyridin-4-yl)-2-phenyl-1H-pyrrole-3-carboxylic acid ethyl ester (45 mg, 40%). ESI (+) MS: m/z 308 (MH+).

Step 3: Condensation to Amides (U1)

A solution of ester 66 (42 mg, 0.15 mmol) in ethanol (0.5 mL) and 4N NaOH (0.5 mL) was warmed at reflux for 2 hours. The mixture was acidified with acetic acid and stripped under reduced pressure. The residue, the crude acid 67, was dissolved in DMF (2 mL) and treated with HOBT.NH$_3$ (42 mg, 0.27 mmol), EDCI (52 mg, 0.27 mmol) and DIPEA (0.12 mL) for 3 days at room temperature (two more additions of the same amount of reagents after one and two days). After concentration and aqueous work-up with ethyl acetate, the residue was purified by reverse phase flash chromatography on a Waters FractionLynx System (see General Methods). Obtained the title compound (33 mg, 80%).

$^1$H NMR (DMSO-d$_6$/400 MHz) δ ppm 5.81 (bs, 2H) 6.74 (s, 1H), 6.81 (bs, 1H), 6.88 (d, J=5.78 Hz, 1H), 7.02 (d, J=2.68 Hz, 1H), 7.25 (bs, 1H), 7.31-7.46 (m, 3H), 7.65 (d, J=8.17 Hz, 2H), 7.90 (d, J=5.78 Hz, 1H), 11.64 (bs, 1H); ESI (+) MS: m/z 308 (MH+).

Selected compounds of formula (I), prepared by the methods described in the examples, are listed in Table X. The table shows the characterization data (HRMS calculated and found) and the structures, where the hydrogen atoms on carbons are not shown.

TABLE X

Structures and data for Selected Compounds of Formula I

| Cpd no. | Structure | M + H (calcul.) | M + H (found) |
|---|---|---|---|
| A1 | 5-(pyridin-4-yl)-2-phenyl-1H-pyrrole-3-carboxamide | 264.1131 | 264.1127 |
| A2 | 5-(pyridin-4-yl)-2-(2-fluorophenyl)-1H-pyrrole-3-carboxamide | 282.1037 | 282.1045 |
| A3 | 5-(pyridin-4-yl)-2-(3-fluorophenyl)-1H-pyrrole-3-carboxamide | 282.1037 | 282.1046 |
| A4 | 5-(pyridin-4-yl)-2-(4-fluorophenyl)-1H-pyrrole-3-carboxamide | 282.1037 | 282.1049 |
| A5 | 5-(pyridin-4-yl)-2-(3-bromophenyl)-1H-pyrrole-3-carboxamide | 342.0236 | 342.0233 |
| A6 | 5-(pyridin-4-yl)-2-(4-bromophenyl)-1H-pyrrole-3-carboxamide | 342.0236 | 342.0240 |

TABLE X-continued

Structures and data for Selected Compounds of Formula I

| Cpd no. | Structure | M + H (calcul.) | M + H (found) |
|---|---|---|---|
| A7 | pyridin-4-yl / pyrrole-3-carboxamide / 2-methylphenyl | 278.1288 | 278.1276 |
| A8 | pyridin-4-yl / pyrrole-3-carboxamide / 3-methylphenyl | 278.1288 | 278.1300 |
| A9 | pyridin-4-yl / pyrrole-3-carboxamide / 4-methylphenyl | 278.1288 | 278.1279 |
| A10 | pyridin-4-yl / pyrrole-3-carboxamide / 2-methoxyphenyl | 294.1237 | 294.1223 |
| A11 | pyridin-4-yl / pyrrole-3-carboxamide / 3-methoxyphenyl | 294.1237 | 294.1237 |
| A12 | pyridin-4-yl / pyrrole-3-carboxamide / 4-methoxyphenyl | 294.1237 | 294.1244 |

TABLE X-continued
Structures and data for Selected Compounds of Formula I
| Cpd no. | Structure | M + H (calcul.) | M + H (found) |
|---|---|---|---|
| A13 | 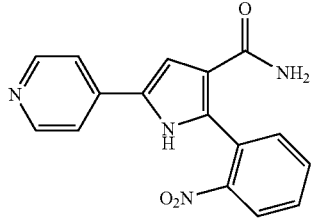 | 309.0982 | 309.0980 |
| A14 | 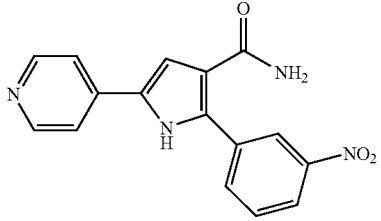 | 309.0982 | 309.0980 |
| A15 | 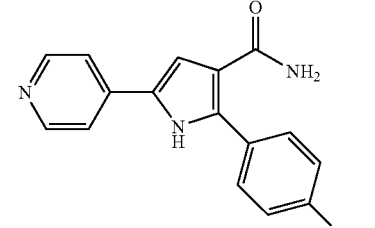 | 309.0982 | 309.0981 |
| A16 | 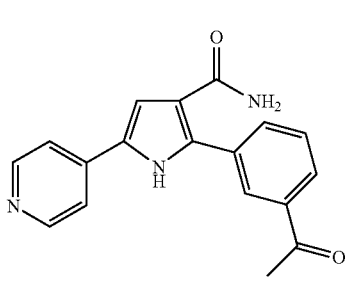 | 306.1237 | 306.1223 |
| A17 | 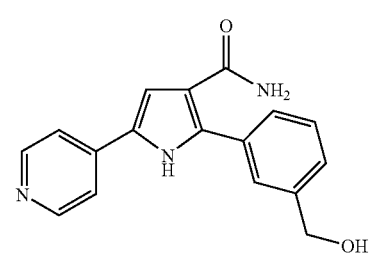 | 294.1237 | 294.1227 |
| A18 | 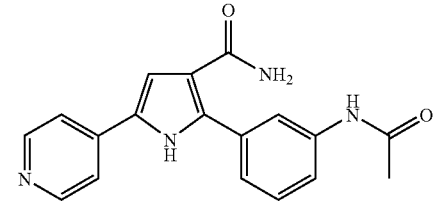 | 321.1346 | 321.1341 |

TABLE X-continued

Structures and data for Selected Compounds of Formula I

| Cpd no. | Structure | M + H (calcul.) | M + H (found) |
|---|---|---|---|
| A19 | 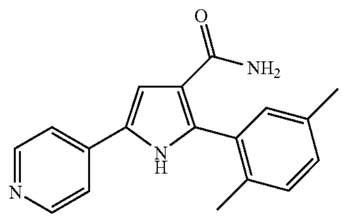 | 292.1444 | 292.1433 |
| A20 | 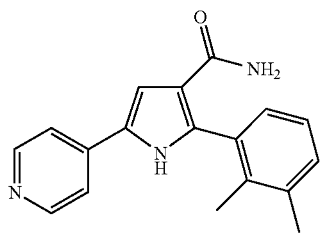 | 292.1444 | 292.1430 |
| A21 | 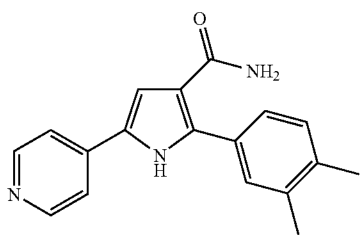 | 292.1444 | 292.1433 |
| A22 | 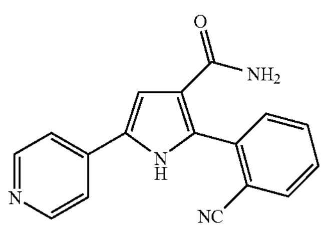 | 289.1084 | 289.1075 |
| A23 | 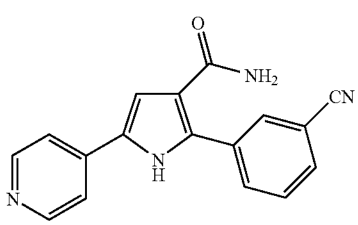 | 289.1084 | 289.1072 |
| A24 | 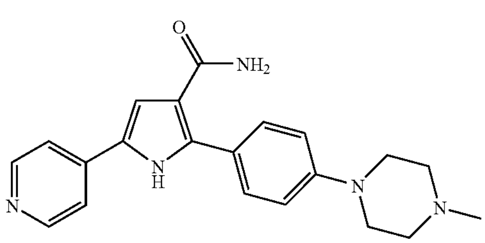 | 362.1975 | 362.1977 |

TABLE X-continued

Structures and data for Selected Compounds of Formula I

| Cpd no. | Structure | M + H (calcul.) | M + H (found) |
|---|---|---|---|
| A25 | 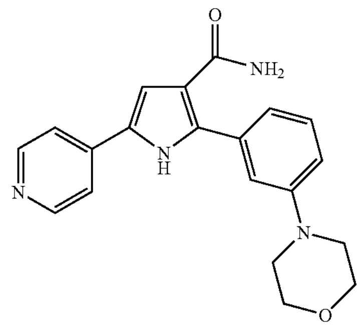 | 349.1659 | 349.1672 |
| A26 | 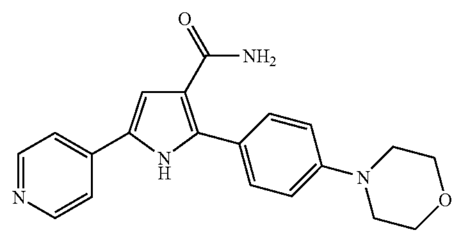 | 349.1659 | 349.1667 |
| A27 | 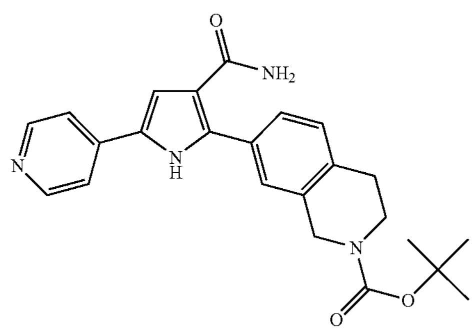 | 419.2078 | 419.2072 |
| A28 | 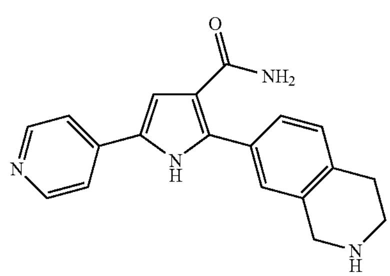 | 319.1553 | 319.1552 |
| A29 | 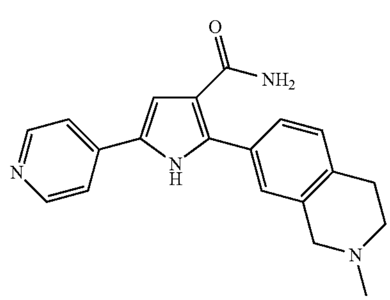 | 333.1710 | 333.1698 |

TABLE X-continued

Structures and data for Selected Compounds of Formula I

| Cpd no. | Structure | M + H (calcul.) | M + H (found) |
|---|---|---|---|
| B1 | [pyrrole with 3-carboxamide, 4-methyl, 2-phenyl, 5-(4-pyridyl)] | 278.1288 | 278.1280 |
| C1 | [pyrrole with 3-carboxamide, 2-(3-thienyl), 5-(4-pyridyl)] | 270.0696 | 270.0698 |
| C2 | [pyrrole with 3-carboxamide, 2-(3-furyl), 5-(4-pyridyl)] | 254.0924 | 254.0912 |
| C3 | [pyrrole with 3-carboxamide, 2,5-bis(4-pyridyl)] | 265.1084 | 65.1078 |
| D1 | [1-ethyl pyrrole with 3-carboxamide, 2-phenyl, 5-(4-pyridyl)] | 292.1444 | 292.1444 |
| E1 | [pyrrole with 3-carboxamide, 2-phenyl, 5-(3-fluoro-4-pyridyl)] | 282.1037 | 282.1039 |

TABLE X-continued

Structures and data for Selected Compounds of Formula I

| Cpd no. | Structure | M + H (calcul.) | M + H (found) |
|---|---|---|---|
| E2 | 5-(3-fluoropyridin-4-yl)-2-(2-methylphenyl)-1H-pyrrole-3-carboxamide | 296.1194 | 296.1191 |
| F1 | 5-(2-aminopyrimidin-4-yl)-2-phenyl-1H-pyrrole-3-carboxamide | 280.1193 | 280.1194 |
| F2 | 5-(2-aminopyrimidin-4-yl)-2-(2-methylphenyl)-1H-pyrrole-3-carboxamide | 294.1349 | 294.1341 |
| F3 | 5-(2-aminopyrimidin-4-yl)-2-(2-ethylphenyl)-1H-pyrrole-3-carboxamide | 308.1506 | 308.1511 |
| F4 | 5-(2-aminopyrimidin-4-yl)-2-(2-fluorophenyl)-1H-pyrrole-3-carboxamide | 298.1099 | 298.1092 |
| F5 | 5-(2-aminopyrimidin-4-yl)-2-(naphthalen-1-yl)-1H-pyrrole-3-carboxamide | 330.1349 | 330.1359 |

TABLE X-continued

Structures and data for Selected Compounds of Formula I

| Cpd no. | Structure | M + H (calcul.) | M + H (found) |
|---|---|---|---|
| F6 | 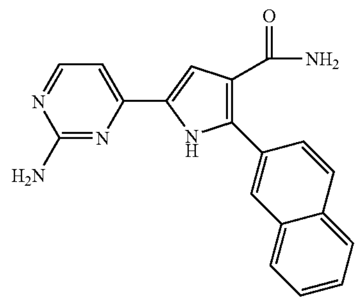 | 330.1349 | 330.1350 |
| F7 | 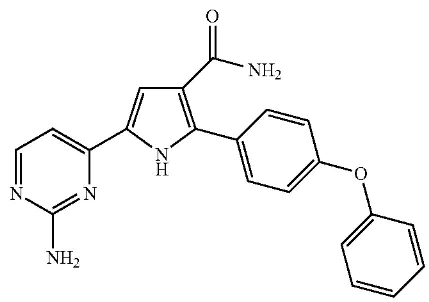 | 372.1455 | 372.1465 |
| F8 | 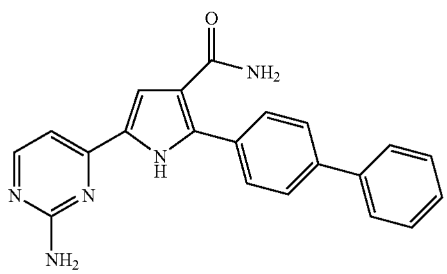 | 356.1506 | 356.1503 |
| F9 | 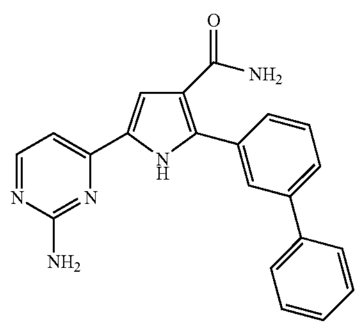 | 356.1506 | 356.1521 |
| F10 | 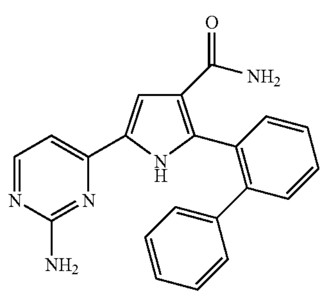 | 356.1506 | 356.1507 |

TABLE X-continued

Structures and data for Selected Compounds of Formula I

| Cpd no. | Structure | M + H (calcul.) | M + H (found) |
|---|---|---|---|
| F11 | 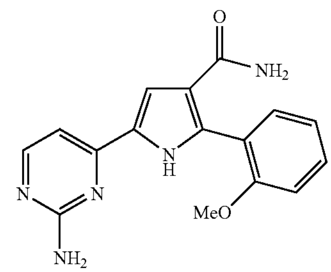 | 310.1298 | 310.1299 |
| F12 | 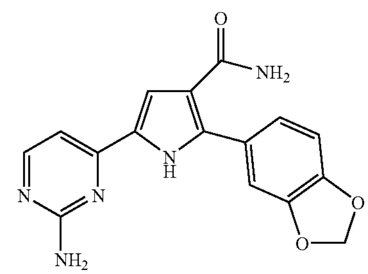 | 324.1091 | 324.1094 |
| F13 | 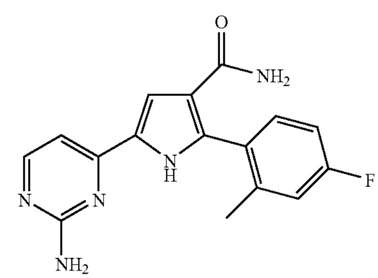 | 312.1255 | 312.1258 |
| F14 | 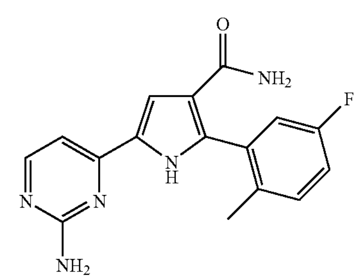 | 312.1255 | 312.1255 |
| F15 | 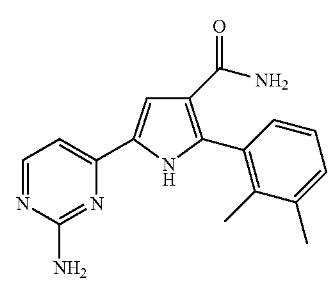 | 308.1506 | 308.1507 |

TABLE X-continued
Structures and data for Selected Compounds of Formula I
| Cpd no. | Structure | M + H (calcul.) | M + H (found) |
|---|---|---|---|
| F16 | 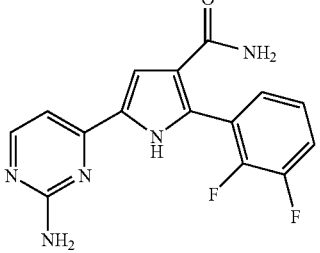 | 316.1004 | 316.1007 |
| F17 | 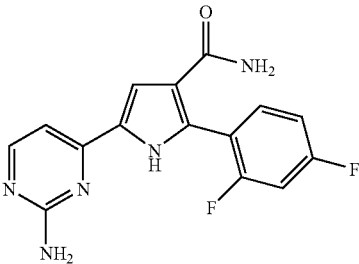 | 316.1005 | 316.1014 |
| F18 | 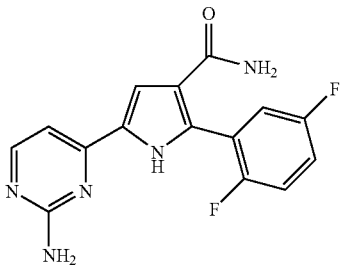 | 316.1005 | 316.1002 |
| F19 | 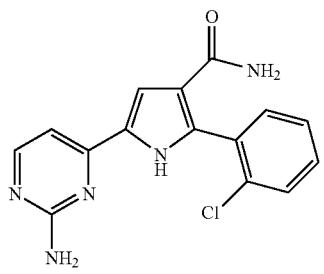 | 314.0803 | 314.0804 |
| F20 | 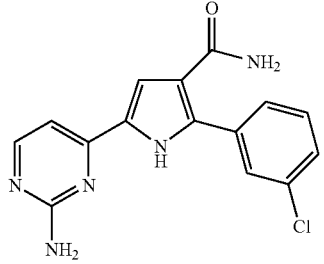 | 314.0803 | 314.0815 |

TABLE X-continued
Structures and data for Selected Compounds of Formula I
| Cpd no. | Structure | M + H (calcul.) | M + H (found) |
|---|---|---|---|
| F21 | 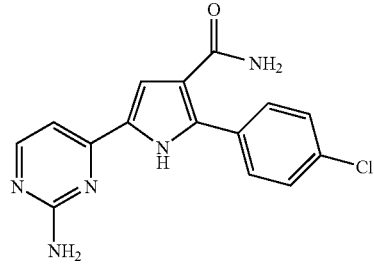 | 314.0803 | 314.0810 |
| F22 | 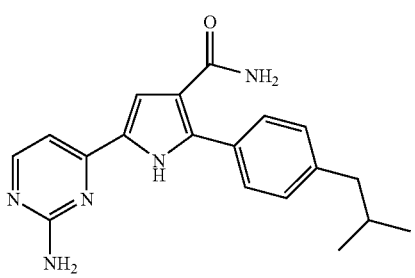 | 336.1819 | 336.1826 |
| F23 | 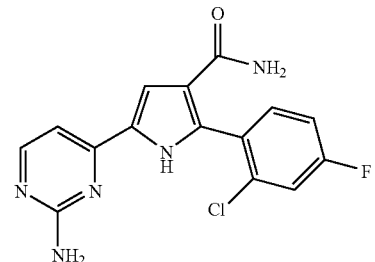 | 332.0709 | 332.0713 |
| F24 | 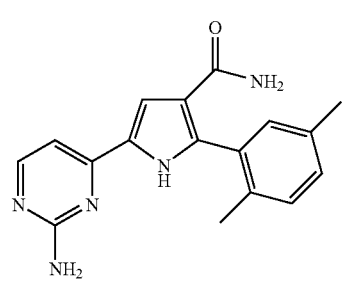 | 308.1506 | 308.1507 |
| F25 | 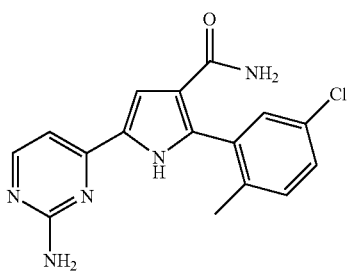 | 328.0960 | 328.0950 |

TABLE X-continued

Structures and data for Selected Compounds of Formula I

| Cpd no. | Structure | M + H (calcul.) | M + H (found) |
|---|---|---|---|
| F26 | 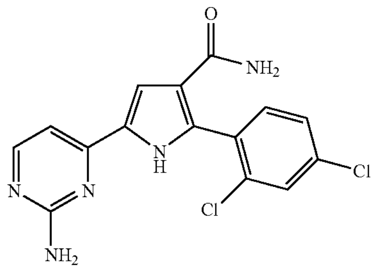 | 348.0414 | 348.0431 |
| F27 | 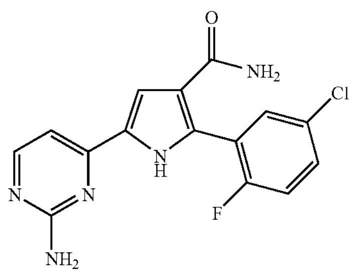 | 332.0709 | 332.0704 |
| F28 | 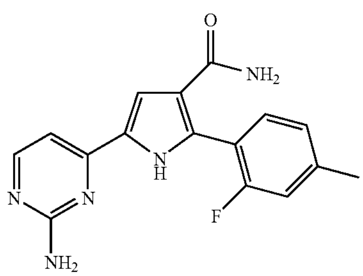 | 312.1255 | 312.1255 |
| F29 | 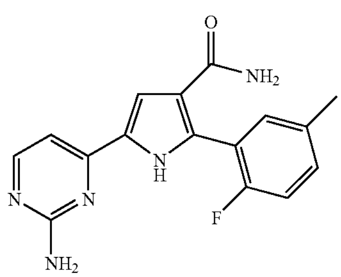 | 312.1255 | 312.1256 |
| F30 | 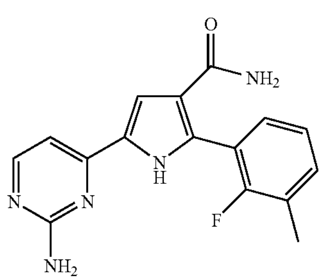 | 312.1255 | 312.1249 |

TABLE X-continued

Structures and data for Selected Compounds of Formula I

| Cpd no. | Structure | M + H (calcul.) | M + H (found) |
|---|---|---|---|
| F31 | 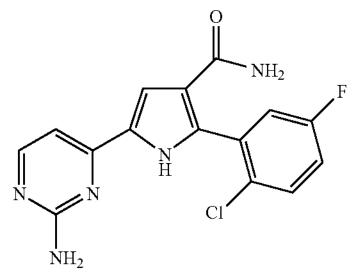 | 332.0709 | 332.0696 |
| F32 | 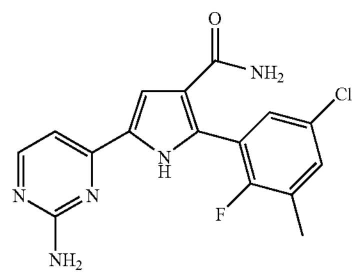 | 346.0866 | 346.0859 |
| F33 | 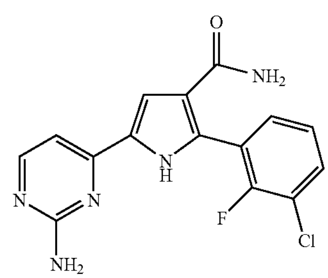 | 332.0709 | 332.0717 |
| F34 | 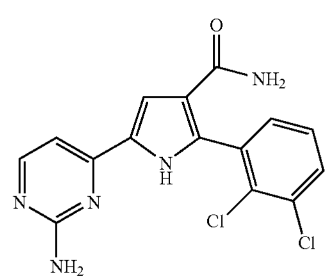 | 348.0414 | 348.0415 |
| F35 | 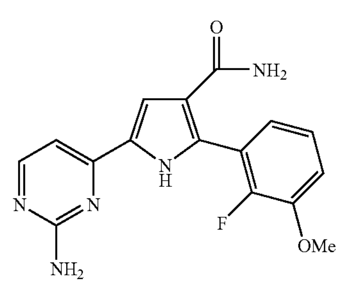 | 328.1205 | 328.1203 |

TABLE X-continued
Structures and data for Selected Compounds of Formula I
| Cpd no. | Structure | M + H (calcul.) | M + H (found) |
| --- | --- | --- | --- |
| F36 | 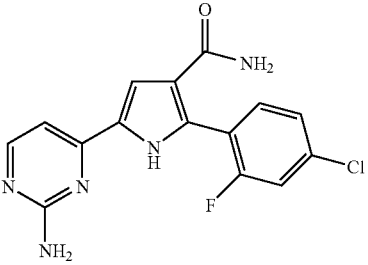 | 332.0709 | 332.0709 |
| F37 | 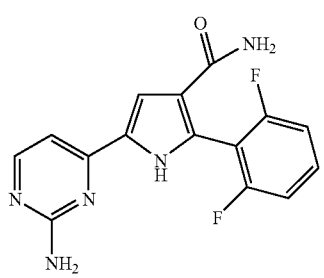 | 316.1005 | 316.1000 |
| G1 | 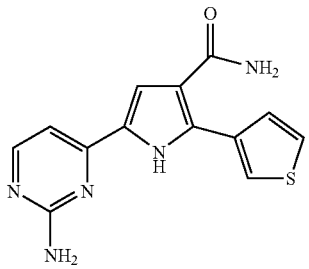 | 286.0757 | 286.0756 |
| G2 | 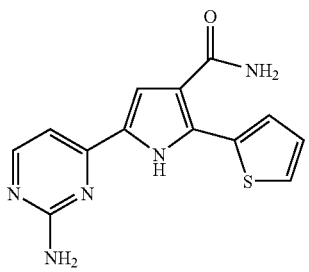 | 286.0757 | 286.0765 |
| G3 | 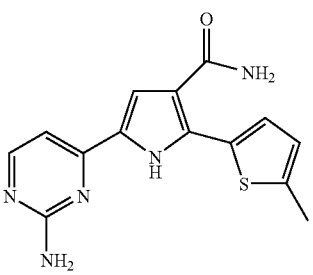 | 300.0914 | 300.0911 |

TABLE X-continued

Structures and data for Selected Compounds of Formula I

| Cpd no. | Structure | M + H (calcul.) | M + H (found) |
|---|---|---|---|
| G4 | 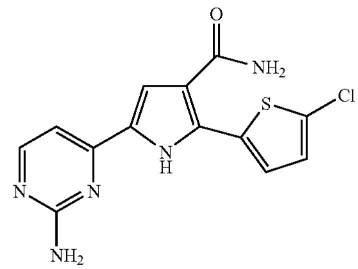 | 320.0367 | 320.0355 |
| G5 | 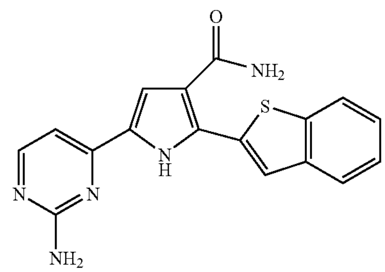 | 336.0914 | 336.0908 |
| G6 | 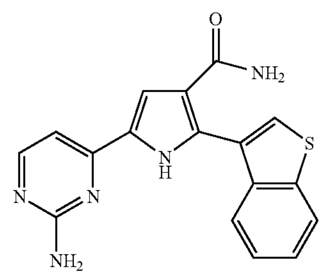 | 336.0914 | 336.0919 |
| G7 | 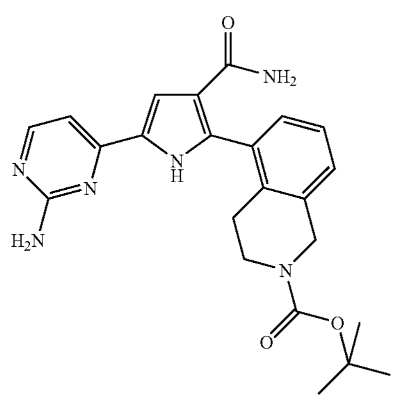 | 435.2139 | 435.2141 |
| G8 | 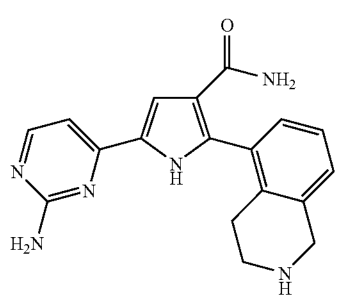 | 335.1615 | 335.1621 |

TABLE X-continued
Structures and data for Selected Compounds of Formula I
| Cpd no. | Structure | M + H (calcul.) | M + H (found) |
|---------|-----------|-----------------|---------------|
| G9 | 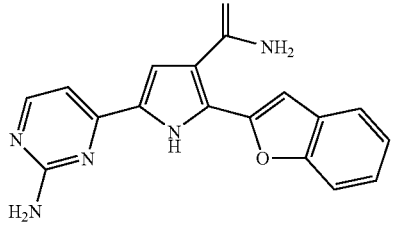 | 320.1142 | 320.1142 |
| G10 | 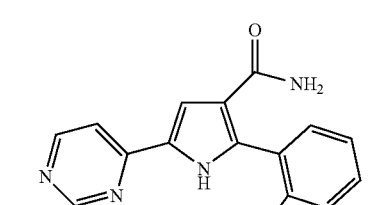 | 370.1298 | 370.1304 |
| G11 | 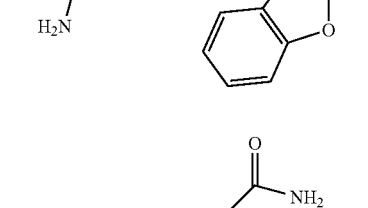 | 281.1145 | 281.1143 |
| G12 | 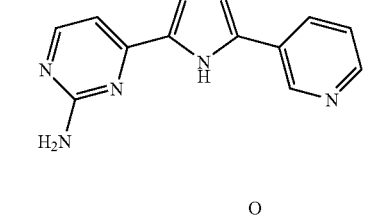 | 281.1145 | 281.1141 |
| G13 | 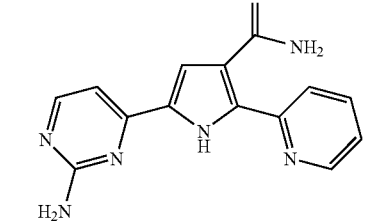 | 333.1458 | 333.1463 |

TABLE X-continued

Structures and data for Selected Compounds of Formula I

| Cpd no. | Structure | M + H (calcul.) | M + H (found) |
|---|---|---|---|
| G14 | 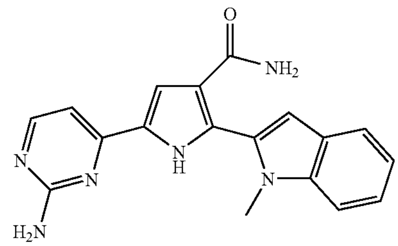 | 333.1458 | 333.1473 |
| G15 | 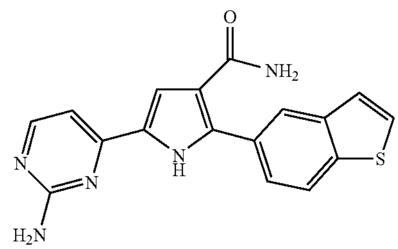 | 336.0914 | 336.0922 |
| H1 | 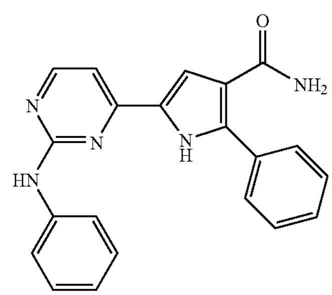 | 356.1506 | 356.1518 |
| L1 | 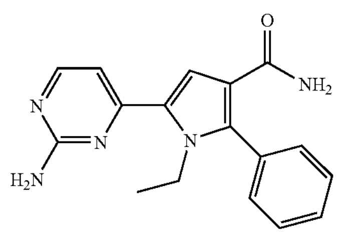 | 308.1506 | 308.1504 |
| M1 | 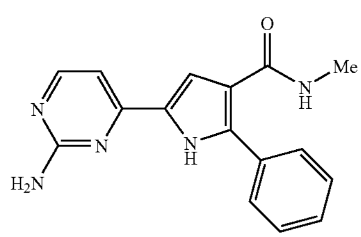 | 294.1349 | 294.1335 |
| M2 | 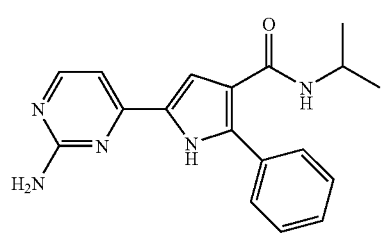 | 322.1662 | 322.1667 |

TABLE X-continued
Structures and data for Selected Compounds of Formula I
| Cpd no. | Structure | M + H (calcul.) | M + H (found) |
|---------|-----------|-----------------|---------------|
| M3 | 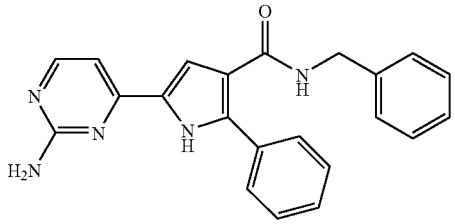 | 370.1662 | 370.1668 |
| M4 | 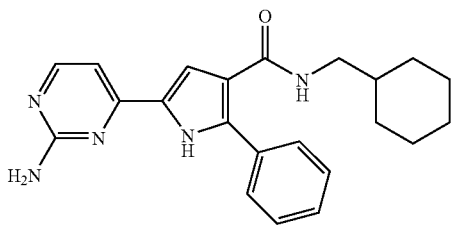 | 376.2132 | 376.2142 |
| M5 | 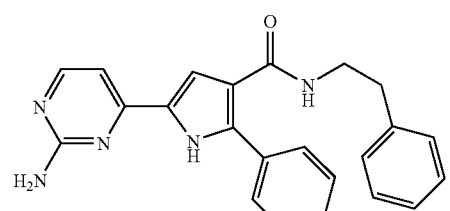 | 384.1819 | 384.1806 |
| N1 | 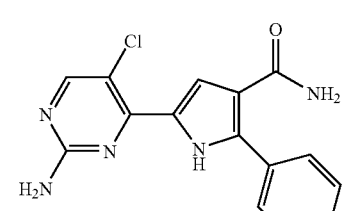 | 314.0803 | 314.0800 |
| N2 | 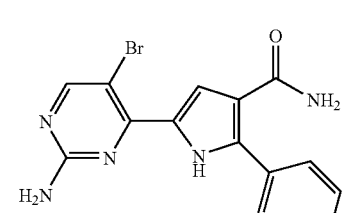 | 358.0298 | 358.0302 |
| N3 | 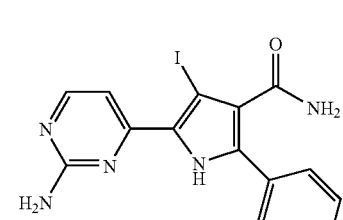 | 406.0159 | 406.0143 |

TABLE X-continued

Structures and data for Selected Compounds of Formula I

| Cpd no. | Structure | M + H (calcul.) | M + H (found) |
|---|---|---|---|
| N4 | 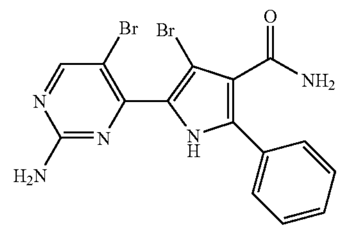 | 435.9403 | 435.9396 |
| N5 | 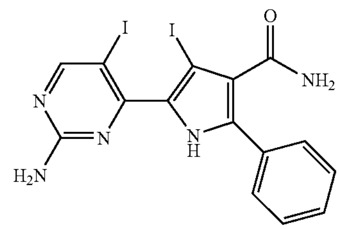 | 531.9126 | 531.9113 |
| N6 | 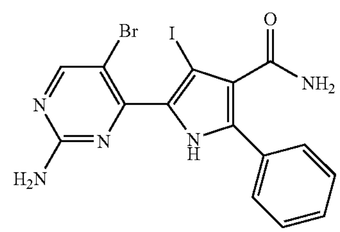 | 483.9264 | 483.9260 |
| N7 | 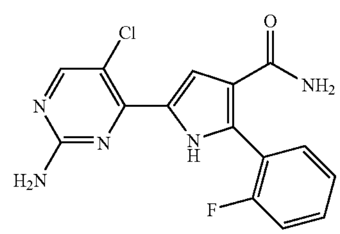 | 332.0709 | 332.0710 |
| N8 | 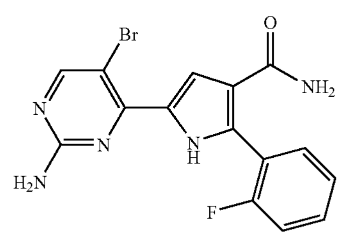 | 376.0204 | 376.0206 |
| O1 | 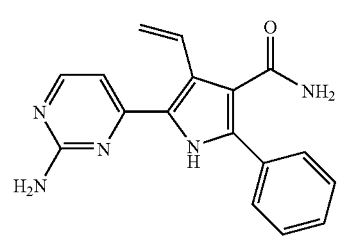 | 306.1349 | 306.1363 |

TABLE X-continued

Structures and data for Selected Compounds of Formula I

| Cpd no. | Structure | M + H (calcul.) | M + H (found) |
| --- | --- | --- | --- |
| P1 | 4-pyridyl-pyrrole-3-carboxamide | 188.0818 | 188.0822 |
| Q1 | 5-(4-pyridyl)-2-cyclohexyl-pyrrole-3-carboxamide | 270.1601 | 270.1602 |
| Q2 | 5-(4-pyridyl)-2-(1-Boc-piperidin-4-yl)-pyrrole-3-carboxamide | 371.2078 | 371.2083 |
| Q3 | 5-(4-pyridyl)-2-(piperidin-4-yl)-pyrrole-3-carboxamide | 271.1553 | 271.1548 |
| R1 | 5-(4-pyridyl)-2-bromo-pyrrole-3-carboxamide | 265.9923 | 265.9935 |
| R2 | 5-(2-amino-4-pyridyl)-2-bromo-pyrrole-3-carboxamide | 281.9985 | 281.9981 |
| R3 | 5-(3-fluoro-4-pyridyl)-2-bromo-pyrrole-3-carboxamide | 283.9829 | 283.9832 |

TABLE X-continued

Structures and data for Selected Compounds of Formula I

| Cpd no. | Structure | M + H (calcul.) | M + H (found) |
|---|---|---|---|
| S1 | 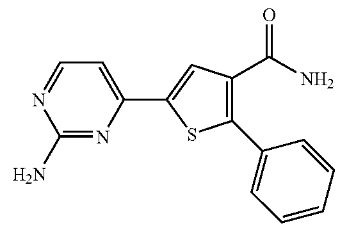 | 297.0805 | 297.0804 |
| T1 | 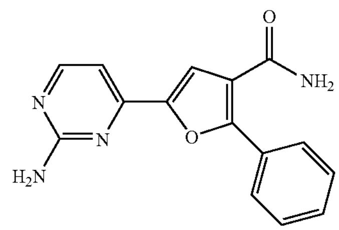 | 281.1033 | 281.1023 |
| U1 | 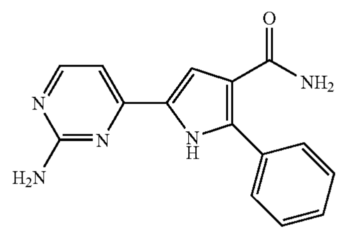 | 279.1240 | 279.1248 |
| V1 | 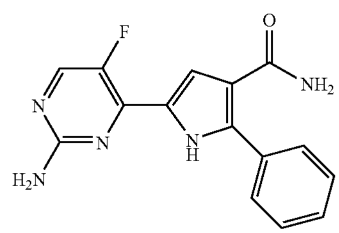 | 298.1099 | 298.1100 |
| Z1 | 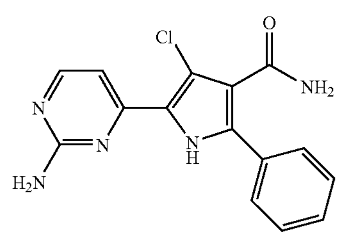 | 314.0803 | 314.0796 |

The invention claimed is:

1. A compound of the formula (I):

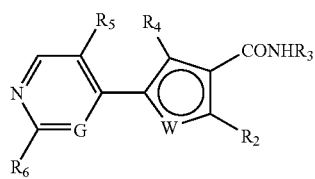

wherein

G is CH or nitrogen atom;
W is an oxygen atom, $NR_1$ or $S(O)n$; n is 0, 1 or 2;
$R_1$ and $R_3$ independently represent hydrogen atom or an optionally substituted group selected from alkyl, cycloalkyl, alkenyl, alkynyl, heterocyclyl, heterocyclylalkyl, aryl, arylalkyl, heterocyclyloxy-alkyl and alkoxycarbonyl group;
$R_2$ is hydrogen or halogen atom, or an optionally substituted group selected from aryl, cycloalkyl and heterocyclyl group;
$R_4$ is hydrogen or halogen atom, or an optionally substituted alkyl or alkenyl group;
$R_5$ is hydrogen or halogen atom;

R<sub>6</sub> is hydrogen atom or NHR<sub>7</sub>;
R<sub>7</sub> is hydrogen atom, an optionally substituted group selected from alkyl, aryl, cycloalkyl and heterocyclyl group or —COR<sub>1</sub> wherein R<sub>1</sub> is as defined above;
or a pharmaceutically acceptable salt thereof, with the proviso that the following compounds are excluded:
2,5-di(pyridin-4-yl)-thiophene-3-carboxylic acid amide,
2,5-di(pyridin-4-yl)-thiophene-3-carboxylic acid methylamide,
2,5-di(pyridin-4-yl)-4-methyl-pyrrole-3-carboxylic acid amide,
5-pyridin-4-yl-furan-3-carboxylic acid [4-methoxy-3-(4-methyl-piperazin-1-yl)-phenyl]-amide,
5-pyridin-4-yl-furan-3-carboxylic acid (1-methyl-1,2,3,4-tetrahydro-quinolin-7-yl)-amide and
N-[2-amino-1-(2,4-dichlorobenzyl)ethyl]-5-[2-(methylamino)pyrimidin-4-yl]thiophene-3-carboxamide.

2. A compound of formula (I) as defined in claim 1 wherein W is NR<sub>1</sub>, R<sub>1</sub> and R<sub>3</sub> independently represent hydrogen atom or an optionally substituted alkyl group, and R<sub>6</sub> is NHR<sub>7</sub> wherein R<sub>7</sub> is hydrogen atom or an optionally substituted aryl group.

3. A compound of formula (I) as defined in claim 1, wherein W is NR<sub>1</sub>; R<sub>1</sub> represent hydrogen atom or an optionally substituted alkyl group; R<sub>3</sub> and R<sub>4</sub> represent hydrogen atoms, R<sub>2</sub> is an optionally substituted aryl or heterocyclyl group; and R<sub>6</sub> is NH<sub>2</sub>.

4. A compound of formula (I) as defined in claim 1, wherein W is NH or R<sup>3</sup> represents hydrogen atom.

5. A compound of formula (I) as defined in claim 1, or a pharmaceutically acceptable salt thereof, which is selected from the group consisting of:
2-phenyl-5-pyridin-4-yl-1H-pyrrole-3-carboxylic acid amide (A1),
2-(2-fluoro-phenyl)-5-pyridin-4-yl-1H-pyrrole-3-carboxylic acid amide (A2),
2-(3-fluoro-phenyl)-5-pyridin-4-yl-1H-pyrrole-3-carboxylic acid amide (A3),
2-(4-fluoro-phenyl)-5-pyridin-4-yl-1H-pyrrole-3-carboxylic acid amide (A4),
5-pyridin-4-yl-2-o-tolyl-1H-pyrrole-3-carboxylic acid amide (A7),
5-pyridin-4-yl-2-m-tolyl-1H-pyrrole-3-carboxylic acid amide (A8),
5-pyridin-4-yl-2-p-tolyl-1H-pyrrole-3-carboxylic acid amide (A9),
2-(3-methoxy-phenyl)-5-pyridin-4-yl-1H-pyrrole-3-carboxylic acid amide (A11),
2-(4-methoxy-phenyl)-5-pyridin-4-yl-1H-pyrrole-3-carboxylic acid amide (A12),
2-(2-nitro-phenyl)-5-pyridin-4-yl-1H-pyrrole-3-carboxylic acid amide (A13),
2-(3-nitro-phenyl)-5-pyridin-4-yl-1H-pyrrole-3-carboxylic acid amide (A14),
2-(2,3-dimethyl-phenyl)-5-pyridin-4-yl-1H-pyrrole-3-carboxylic acid amide (A20),
5-pyridin-4-yl-2-thiophen-3-yl-1H-pyrrole-3-carboxylic acid amide (C1),
2-furan-3-yl-5-pyridin-4-yl-1H-pyrrole-3-carboxylic acid amide (C2),
5-(3-fluoro-pyridin-4-yl)-2-phenyl-1H-pyrrole-3-carboxylic acid amide (E1),
5-(3-fluoro-pyridin-4-yl)-2-o-tolyl-1H-pyrrole-3-carboxylic acid amide (E2),
5-(2-amino-pyrimidin-4-yl)-2-phenyl-1H-pyrrole-3-carboxylic acid amide (F1),
5-(2-amino-pyrimidin-4-yl)-2-o-tolyl-1H-pyrrole-3-carboxylic acid amide (F2),
5-(2-amino-pyrimidin-4-yl)-2-(2-fluoro-phenyl)-1H-pyrrole-3-carboxylic acid amide (F4),
5-(2-amino-pyrimidin-4-yl)-2-(4-fluoro-2-methyl-phenyl)-1H-pyrrole-3-carboxylic acid amide (F13),
5-(2-amino-pyrimidin-4-yl)-2-(5-fluoro-2-methyl-phenyl)-1H-pyrrole-3-carboxylic acid amide (F14),
5-(2-amino-pyrimidin-4-yl)-2-(2,3-dimethyl-phenyl)-1H-pyrrole-3-carboxylic acid amide (F15),
5-(2-amino-pyrimidin-4-yl)-2-(2,3-difluoro-phenyl)-1H-pyrrole-3-carboxylic acid amide (F16),
5-(2-amino-pyrimidin-4-yl)-2-(2,4-difluoro-phenyl)-1H-pyrrole-3-carboxylic acid amide (F17),
5-(2-amino-pyrimidin-4-yl)-2-(2,5-difluoro-phenyl)-1H-pyrrole-3-carboxylic acid amide (F18),
5-(2-amino-pyrimidin-4-yl)-2-(2-chloro-phenyl)-1H-pyrrole-3-carboxylic acid amide (F19),
5-(2-amino-pyrimidin-4-yl)-2-(2-chloro-4-fluoro-phenyl)-1H-pyrrole-3-carboxylic acid amide (F23),
5-(2-amino-pyrimidin-4-yl)-2-(2,4-dichloro-phenyl)-1H-pyrrole-3-carboxylic acid amide (F26),
5-(2-amino-pyrimidin-4-yl)-2-(2-fluoro-4-methyl-phenyl)-1H-pyrrole-3-carboxylic acid amide (F28),
5-(2-amino-pyrimidin-4-yl)-2-(2-fluoro-3-methyl-phenyl)-1H-pyrrole-3-carboxylic acid amide (F30),
5-(2-amino-pyrimidin-4-yl)-2-(2-chloro-5-fluoro-phenyl)-1H-pyrrole-3-carboxylic acid amide (F31),
5-(2-amino-pyrimidin-4-yl)-2-(3-chloro-2-fluoro-phenyl)-1H-pyrrole-3-carboxylic acid amide (F33),
5-(2-amino-pyrimidin-4-yl)-2-(2,3-dichloro-phenyl)-1H-pyrrole-3-carboxylic acid amide (F34),
5-(2-amino-pyrimidin-4-yl)-2-(2-fluoro-3-methoxy-phenyl)-1H-pyrrole-3-carboxylic acid amide (F35),
5-(2-amino-pyrimidin-4-yl)-2-(4-chloro-2-fluoro-phenyl)-1H-pyrrole-3-carboxylic acid amide (F36),
5-(2-amino-pyrimidin-4-yl)-2-(2-bromo-phenyl)-1H-pyrrole-3-carboxylic acid amide (F38),
5-(2-amino-pyrimidin-4-yl)-2-(2-chloro-3-methoxy-phenyl)-1H-pyrrole-3-carboxylic acid amide (F39),
5-(2-amino-pyrimidin-4-yl)-2-(3-methoxy-2-methyl-phenyl)-1H-pyrrole-3-carboxylic acid amide (F40),
5-(2-amino-pyrimidin-4-yl)-2-(2-chloro-3-fluoro-phenyl)-1H-pyrrole-3-carboxylic acid amide (F41),
5-(2-amino-pyrimidin-4-yl)-2-(3-bromo-2-chloro-phenyl)-1H-pyrrole-3-carboxylic acid amide (F42),
5-(2-amino-pyrimidin-4-yl)-2-(2-bromo-3-chloro-phenyl)-1H-pyrrole-3-carboxylic acid amide (F43),
5-(2-amino-pyrimidin-4-yl)-2-(2,3-dibromo-phenyl)-1H-pyrrole-3-carboxylic acid amide (F44),
5-(2-amino-pyrimidin-4-yl)-2-(3-bromo-2-fluoro-phenyl)-1H-pyrrole-3-carboxylic acid amide (F45),
5-(2-amino-pyrimidin-4-yl)-2-(3-bromo-2-methyl-phenyl)-1H-pyrrole-3-carboxylic acid amide (F46),
5-(2-amino-pyrimidin-4-yl)-2-(2-bromo-3-methyl-phenyl)-1H-pyrrole-3-carboxylic acid amide (F47),
5-(2-amino-pyrimidin-4-yl)-2-(4-methoxy-3-methyl-phenyl)-1H-pyrrole-3-carboxylic acid amide (F48),
5-(2-amino-pyrimidin-4-yl)-2-(3,4-dimethoxy-phenyl)-1H-pyrrole-3-carboxylic acid amide (F49),
5-(2-amino-pyrimidin-4-yl)-2-(2-fluoro-4-methoxy-phenyl)-1H-mmole-3-carboxylic acid amide (F50),
5-(2-amino-pyrimidin-4-yl)-2-(2-chloro-4-methoxy-phenyl)-1H-pyrrole-3-carboxylic acid amide (F51),
5-(2-amino-pyrimidin-4-yl)-2-(2-bromo-4-fluoro-phenyl)-1H-pyrrole-3-carboxylic acid amide (F52), 5-(2-amino-pyrimidin-4-yl)-2-(4-methoxy-2-methyl-phenyl)-1H-pyrrole-3-carboxylic acid amide (F53),
5-(2-amino-pyrimidin-4-yl)-2-thiophen-3-yl-1H-pyrrole-3-carboxylic acid amide (G1),
5-(2-amino-pyrimidin-4-yl)-2-thiophen-2-yl-1H-pyrrole-3-carboxylic acid amide (G2),
5-(2-amino-pyrimidin-4-yl)-2-(5-methyl-thiophen-2-yl)-1H-pyrrole-3-carboxylic acid amide (G3),
5-(2-amino-pyrimidin-4-yl)-2-(5-chloro-thiophen-2-yl)-1H-pyrrole-3-carboxylic acid amide (G4),
5-(2-amino-5-chloro-pyrimidin-4-yl)-2-phenyl-1H-pyrrole-3-carboxylic acid amide (N1),
5-(2-amino-5-bromo-pyrimidin-4-yl)-2-phenyl-1H-pyrrole-3-carboxylic acid amide (N2),
5-(2-amino-pyrimidin-4-yl)-4-iodo-2-phenyl-1H-pyrrole-3-carboxylic acid amide (N3),
5-(2-amino-5-chloro-pyrimidin-4-yl)-2-(2-fluoro-phenyl)-1H-pyrrole-3-carboxylic acid amide (N7),
5-(2-amino-5-bromo-pyrimidin-4-yl)-2-(2-fluoro-phenyl)-1H-pyrrole-3-carboxylic acid amide (N8),
5-(2-amino-pyrimidin-4-yl)-2-phenyl-thiophene-3-carboxylic acid amide (S1),
5-(2-amino-5-fluoro-pyrimidin-4-yl)-2-phenyl-1H-pyrrole-3-carboxylic acid amide (V1) and
5-(2-amino-pyrimidin-4-yl)-4-chloro-2-phenyl-1H-pyrrole-3-carboxylic acid amide (Z1).

6. A compound of formula (I) as defined in claim 1, or a pharmaceutically acceptable salt thereof, which is
5-(2-amino-pyrimidin-4-yl)-2-(2,3-dimethyl-phenyl)-1H-pyrrole-3-carboxylic acid amide (F15),
5-(2-amino-pyrimidin-4-yl)-2-(2,4-dichloro-phenyl)-1H-pyrrole-3-carboxylic acid amide (F26) or
5-(2-amino-pyrimidin-4-yl)-2-(4-chloro-2-fluoro-phenyl)-1H-pyrrole-3-carboxylic acid amide (F36).

7. A process for preparing a compound of formula (I) as defined in claim 1, which process comprises:
a) coupling a compound of formula 1E

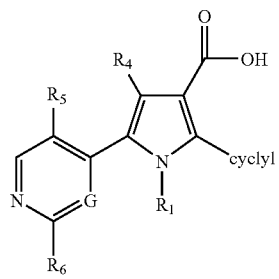

wherein $R_1$, $R_4$, $R_5$, $R_6$ and G are as defined in claim 1 and cyclyl is an optionally substituted group selected form aryl, cycloalkyl and heterocyclyl group,
either with an activated form of ammonia, optionally in the presence of a condensing agent, or with an amine of formula $R_3$—$NH_2$, wherein $R_3$ is as defined in claim 1, thus obtaining a compound of formula (I) as defined in claim 1 wherein W is NR1 wherein $R_1$ is as defined in claim 1, and $R_2$ is an optionally substituted group selected from aryl, cycloalkyl and heterocyclyl group;
b) optionally converting a compound of formula (I) into another different compound of formula (I), and, if desired, converting a compound of formula (I) into a pharmaceutically acceptable salt thereof or converting a salt into the free compound of formula (I).

8. A process for preparing a compound of formula (I) as defined in claim 1, which process comprises:
a) amidating a compound formula 5D:

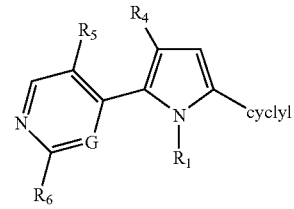

wherein $R_1$, $R_5$, $R_6$, and G are as defined in claim 1 and $R_4$ is as defined in claim 1 but not hydrogen atom, and cyclyl is an optionally substituted group selected form aryl, cycloalkyl and heterocyclyl group, and
b) optionally converting a compound of formula (I) into another different compound of formula (I), and, if desired, converting a compound of formula (I) into a pharmaceutically acceptable salt thereof or converting a salt into the free compound of formula (I).

9. A process for preparing a compound of formula (I) as defined in claim 1, which process comprises:
a') coupling a compound of formula 2D

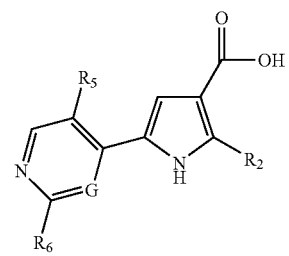

wherein $R_2$ is hydrogen or halogen atom, and $R_5$, $R_6$, and G are as defined in claim 1, either with an activated form of ammonia, optionally in the presence of a condensing agent, or with an amine of formula $R_3$—$NH_2$, wherein $R_3$ is as defined in claim 1, thus obtaining a compound of formula (I) wherein W is N, $R_1$ is hydrogen atom and $R_2$ is hydrogen atom or halogen atom;
a'$_1$) optionally converting the resultant compound of formula (I) wherein $R_2$ is halogen atom into another compound of formula (I) wherein $R_2$ is hydrogen atom or an optionally substituted group selected from aryl, cycloalkyl and heterocyclyl group and/or
a'$_2$) converting the resultant compound of formula (I) wherein $R_1$ is hydrogen atom into another compound of formula (I) wherein $R_1$ is an optionally substituted group selected from alkyl, cycloalkyl, alkenyl, alkynyl, heterocyclyl, aryl, heterocyclyloxy-alkyl and alkoxycarbonyl; and, if desired, converting a compound of formula (I) into a pharmaceutically acceptable salt thereof or converting a salt into the free compound of formula (I).

10. A process for preparing a compound of formula (I) as defined in claim 1, which process comprises:
a') cleaving a compound of formula 3A or 3B

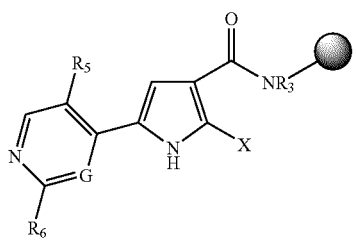

3A

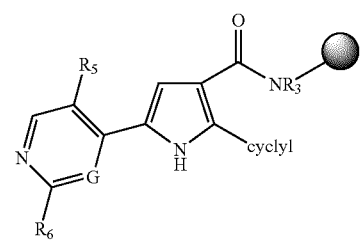

3B wherein $R_3$, $R_5$, $R_6$, and G are as defined in claim 1, and X is bromine or chlorine atom, and cyclyl is an optionally substituted group selected form aryl, cycloalkyl and heterocyclyl group, and the symbol

represents a solid support to which the chemical molecule is linked, and, if desired, converting the resultant compound of formula (I) wherein W is nitrogen atom and $R_2$ is halogen or an optionally substituted group selected from aryl, cycloalkyl and heterocyclyl group, into a pharmaceutically acceptable salt thereof or converting a salt into the free compound of formula (I).

11. A process for preparing a compound of formula (I) as defined in claim 1, which process comprises:
a) coupling a compound of formula 7B

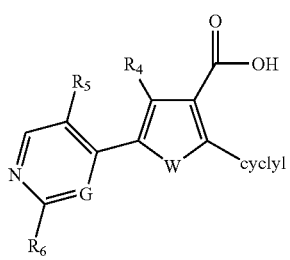

7B wherein W is an oxygen or sulphur atom, $R_4$, $R_5$, $R_6$ and G are as defined in claim 1 and cyclyl is an optionally substituted group selected form aryl, cycloalkyl and heterocyclyl group, either with an activated form of ammonia, optionally in the presence of a condensing agent, or with an amine of formula $R_3$—$NH_2$, wherein $R_3$ is as defined in claim 1, thus obtaining a compound of formula (I) wherein W is an oxygen or sulphur atom, and $R_2$ is an optionally substituted group selected from aryl, cycloalkyl and heterocyclyl group;
b) optionally converting a compound of formula (I) into another different compound of formula (I), and, if desired, converting a compound of formula (I) into a pharmaceutically acceptable salt thereof or converting a salt into the free compound of formula (I).

12. A process for preparing the compound of formula (I) as defined in claim 1, which process comprises:
a) reacting a compound of formula 9

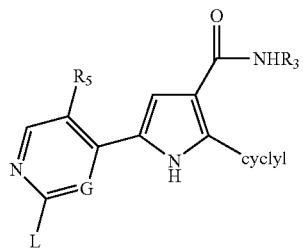

9 wherein L is a leaving group such as halogen, methansulphonyl or methansulfinyl and $R_3$, $R_5$, and G are as defined in claim 1, and cyclyl is an optionally substituted group selected form aryl, cycloalkyl and heterocyclyl group, either with an activated form of ammonia, like lithium bis(trimethylsilyl)amide, optionally in the presence of a condensing agent, or with hydrazine followed by reduction to amine, or with an amine of formula $R_7$—$NH_2$, wherein $R_7$ is as defined above, in a Pd-catalyzed coupling, thus obtaining a compound of formula (I) as defined above wherein W is $NR_1$, $R_1$ is hydrogen atom and $R_6$ is NH—$R_7$; and, if desired, converting a compound of formula (I) into a pharmaceutically acceptable salt thereof or converting a salt into the free compound of formula (I).

13. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

14. A pharmaceutical composition according to claim 13 further comprising one or more chemotherapeutic agents.

15. A product or kit comprising a compound of formula (I) or a pharmeutically acceptable salt thereof, as defined in claim 1, or pharmaceutical compositions thereof as defined in claim 13, and one or more chemotherapeutic agent, as a combined preparation for simultaneous, separate or sequential use in anticancer therapy.

16. An intermediate of the formula 1D or 1E:

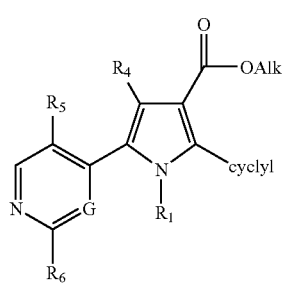

1D

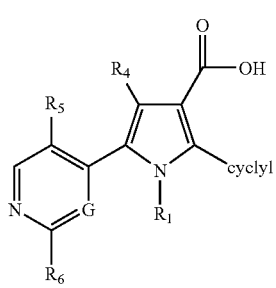

wherein G, $R_1$, $R_4$, $R_5$ and $R_6$ are as defined in claim 1, Alk is a $C_1$-$C_5$ alkyl group, and cyclyl is an optionally substituted group selected form aryl, cycloalkyl and heterocyclyl group, with the proviso that the following compounds are excluded:

1H-Pyrrole-3-carboxylic acid, 1-(methoxymethyl)-4-methyl-2,5-di-4-pyridinyl-, ethyl ester;

1H-pyrrole-3-carboxylic acid, 2,5-di-4-pyridinyl-, methyl ester, 1H-pyrrole-3-carboxylic acid, 4-methyl-2-phenyl-5-(4-pyridinyl)-, methyl ester, 1H-pyrrole-3-carboxylic acid, 4-methyl-2,5-di-4-pyridinyl-, compd. with morpholine (1:1), 1H-pyrrole-3-carboxylic acid, 4-methyl-2,5-di-4-pyridinyl, 1H-pyrrole-3-carboxylic acid, 4-(methoxymethyl)-2,5-di-4-pyridinyl-, methyl ester, 1H-pyrrole-3-carboxylic acid, 4-butyl-2,5-di-4-pyridinyl-, ethyl ester, 1H-pyrrole-3-carboxylic acid, 4-(1-methylethyl)-2,5-di-4-pyridinyl-, ethyl ester, 1H-pyrrole-3-carboxylic acid, 4-propyl-2,5-di-4-pyridinyl-, ethyl ester, 1H-pyrrole-3-carboxylic acid, 4-methyl-2,5-di-4-pyridinyl-, 2-methoxyethyl ester, 1H-pyrrole-3-carboxylic acid, 4-methyl-2,5-di-4-pyridinyl-, butyl ester, 1H-pyrrole-3-carboxylic acid, 4-methyl-2,5-di-4-pyridinyl-, propyl ester, 1H-pyrrole-3-carboxylic acid, 4-methyl-2,5-di-4-pyridinyl-, 1,1-dimethylethyl ester, 1H-pyrrole-3-carboxylic acid, 4-methyl-2,5-di-4-pyridinyl-, 1-methylethyl ester, 1H-pyrrole-3-carboxylic acid, 4-methyl-2,5-di-4-pyridinyl-, 2-propenyl ester, 1H-pyrrole-3-carboxylic acid, 4-methyl-2,5-di-4-pyridinyl-, phenylmethyl ester, 1H-pyrrole-3-carboxylic acid, 4-methyl-2,5-di-4-pyridinyl-, methyl ester, 1H-pyrrole-3-carboxylic acid, 4-methyl-2,5-di-4-pyridinyl-, ethyl ester and 1H-pyrrole-3-carboxylic acid, 4-ethyl-2,5-di-4-pyridinyl-, ethyl ester.

* * * * *